(12) United States Patent
Schiltz et al.

(10) Patent No.: US 11,890,346 B2
(45) Date of Patent: Feb. 6, 2024

(54) PROTEOLYSIS-TARGETING CHIMERIC MOLECULES (PROTACS) THAT INDUCE DEGRADATION OF C-MYC PROTEIN

(71) Applicant: NORTHWESTERN UNIVERSITY, Evanston, IL (US)

(72) Inventors: Gary E. Schiltz, Naperville, IL (US); Atul Jain, Evanston, IL (US); Huiying Han, Chicago, IL (US); Sarki A. Abdulkadir, Lombard, IL (US)

(73) Assignee: Northwestern University, Evanston, IL (US)

( * ) Notice: Subject to any disclaimer, the term of this patent is extended or adjusted under 35 U.S.C. 154(b) by 151 days.

(21) Appl. No.: 16/900,782

(22) Filed: Jun. 12, 2020

(65) Prior Publication Data
US 2020/0390894 A1 Dec. 17, 2020

Related U.S. Application Data

(60) Provisional application No. 62/860,729, filed on Jun. 12, 2019.

(51) Int. Cl.
*C07D 401/14* (2006.01)
*A61K 47/54* (2017.01)
*C07D 417/14* (2006.01)

(52) U.S. Cl.
CPC .......... *A61K 47/545* (2017.08); *C07D 401/14* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 8,168,206 B1 * | 5/2012 | Hunt | A61K 47/32 424/247.1 |
| 9,669,014 B2 | 6/2017 | Siddique | |
| 9,688,637 B2 | 6/2017 | Schiltz | |
| 9,981,968 B2 | 5/2018 | Schiltz | |
| 10,093,668 B2 | 10/2018 | Schiltz | |
| 10,435,375 B2 | 10/2019 | Schiltz | |
| 10,640,502 B2 | 5/2020 | Shilatifard | |
| 10,851,082 B2 | 12/2020 | Schiltz | |
| 2014/0356322 A1 | 12/2014 | Crews | |
| 2016/0002252 A1 | 1/2016 | Schiltz | |
| 2016/0052870 A1 | 2/2016 | Schiltz | |
| 2016/0214969 A1 | 7/2016 | Siddique | |
| 2017/0121326 A1 | 5/2017 | Schiltz | |
| 2017/0253581 A1 | 9/2017 | Schiltz | |
| 2018/0244654 A1 | 8/2018 | Schiltz | |
| 2019/0062281 A1 | 2/2019 | Schiltz | |
| 2019/0276458 A1 | 9/2019 | Schiltz | |

FOREIGN PATENT DOCUMENTS

| | | | |
|---|---|---|---|
| WO | 2016197078 A1 | 12/2016 | |
| WO | 2017117473 A1 | 7/2017 | |
| WO | WO-2019199816 A1 * | 10/2019 | ........... A61K 31/437 |

OTHER PUBLICATIONS

An, S. et al. "Small-molecule PROTACs: An emerging and promising approach for the development of targeted therapy drugs." EBioMedicine 36 (2018): 553-562.

Gu, S. et al., "PROTACs: An Emerging Targeting Technique for Protein Degradation in Drug Discovery," Bioessays. Apr. 2018; 40(4):e1700247.

International Searching Authority. International Search Report and Written Opinion for application PCT/US2020/037608, dated Oct. 1, 2020. 6 pages.

* cited by examiner

*Primary Examiner* — Medhanit W Bahta
(74) *Attorney, Agent, or Firm* — Quarles & Brady LLP

(57) ABSTRACT

Disclosed are proteolysis-targeting chimeric molecules (PROTACs) that induce degradation of c-MYC protein. The disclosed PROTACs typically include a first targeting moiety that binds to c-MYC ($M_{c\text{-}MYC}$) which may be derived from a substituted heterocycle that binds to c-MYC such as a substituted pyrazole. The first targeting moiety typically is linked via a bond or a linker (L) to a second targeting moiety that binds to an E3 ubiquitin ligase ($M_{E3}$). As such, the disclosed PROTACS may be described as having a formula $M_{c\text{-}MYC}\text{-}L\text{-}M_{E3}$ or $M_{E3}\text{-}L\text{-}M_{c\text{-}MYC}$.

4 Claims, 4 Drawing Sheets

Figure 1

Compound Identification

| NO. | Compound_ID | NU ID |
|---|---|---|
| 1 | A5BC2R1 | NUCC-0226200 |
| 2 | A5BC2R2 | NUCC-0226201 |
| 3 | A5BC3R3 | NUCC-0226202 |
| 4 | A5BC2R4 | NUCC-0226203 |
| 5 | A5BCM1R1 | NUCC-0226204 |
| 6 | A5BCM1R4 | NUCC-0226205 |
| 7 | A5BC0R1 | NUCC-0226206 |
| 8 | A5BC1R1 | NUCC-0226207 |
| 9 | A5BC1R4 | NUCC-0226208 |
| 10 | A5BC3R4 | NUCC-0226209 |
| 11 | A5BC3R1 | NUCC-0226210 |

PROTEOLYSIS-TARGETING CHIMERIC MOLECULES (PROTACS) THAT INDUCE DEGRADATION OF C-MYC PROTEIN

CROSS-REFERENCE TO RELATED PATENT APPLICATIONS

The present application claims the benefit of priority under 37 C.F.R. § 119(e) to U.S. Provisional Application No. 62/860,729, filed on Jun. 12, 2019, the content of which is incorporated herein by reference in its entirety.

BACKGROUND

The field of the invention relates to proteolysis-targeting chimeric molecules (PROTACs) that induce degradation of c-MYC protein. In particular, the field of the invention relates to PROTACs that target c-MYC for degradation which may be utilized for the treatment of diseases and disorders associated with c-MYC such as cell proliferation diseases and disorders including cancer The c-MYC oncogene is de-regulated and plays a causal role in a majority of human cancer and c-MYC inhibition profoundly affects tumor growth or survival in multiple models. MYC is the most common oncogene involved in human cancers and is overexpressed in up to half of all cancers. Therefore, developing c-MYC inhibitors is among the most attractive potential anti-cancer strategies. Unfortunately, due to the difficulty in targeting transcription factors with small molecules, c-MYC is currently regarded as "undruggable." We previously disclosed a new approach to targeting c-MYC involving a series of new small molecule inhibitors derived from substituted pyrazoles, pyrimidines, or triazoles. These compounds selectively target c-MYC-driven cell proliferation and interfere with binding of c-MYC to DNA. (See, e.g., U.S. Publication No. 2019/0062281, published on Feb. 28, 2019, the content of which is incorporated herein by reference in its entirety.)

Proteolysis-targeting chimeric molecules (PROTACs) are an emerging technology that may be utilized to target previously "undruggable" targets, such as transcription factors and non-enzymatic proteins. (See, e.g., An et al., "Small-molecule PROTACs: An emerging and promising approach for the development of targeted therapy drugs," EBioMedicine. 2018 October; 36: 553-562; and Gu et al., "PROTACs: An Emerging Targeting Technique for Protein Degradation in Drug Discovery," Bioessays. 2018 April; 40(4): e1700247, the contents of which are incorporated herein by reference in their entireties). PROTACs are chimeric molecules that may be characterized as "hetero-bifunctional" in that PROTACs include a ligand for recruiting an E3 ubiquitin ligase, a linker, and another ligand to bind with the protein targeted for degradation. Designed as such, PROTACs "hijack" the E3 ubiquitin ligase to the protein which is targeted for protein degradation via ubiquitination, even if the targeted protein is not a physiological substrate for degradation via the ubiquitin-proteasome system. Here, we disclose PROTACs that induce degradation of c-MYC protein.

SUMMARY

Disclosed are proteolysis-targeting chimeric molecules (PROTACs) that induce degradation of c-MYC protein. The disclosed PROTACs comprise a moiety that binds to c-MYC covalently attached to a moiety that binds to a ubiquitin ligase. The disclosed PROTACs typically include a first targeting moiety that binds to c-MYC ($M_{c\text{-}MYC}$) which may be derived from a substituted heterocycle that binds to c-MYC such as a substituted pyrazole. The first targeting moiety may be covalently attached via a bond or a linker (L) to a second targeting moiety that binds to a ubiquitin ligase such as an E3 ubiquitin ligase ($M_{E3}$). As such, the disclosed PROTACS may be described as having a formula $M_{c\text{-}MYC}$-L-$M_{E3}$ or $M_{E3}$-L-$M_{c\text{-}MYC}$.

The disclosed PROTACs target the E3 ubiquitin ligase moiety to c-MYC which subsequently is ubiquitinated and targeted for degradation. The disclosed PROTACs may be utilized for the treatment of diseases and disorders associated with c-MYC such as cell proliferation diseases and disorders including cancer.

The disclosed PROTAC typically include a first targeting moiety that binds to c-MYC ($M_{c\text{-}MYC}$) which is derived from a substituted heterocycle that binds to c-MYC. Suitable substituted heterocycles that bind to c-MYC may include, but are not limited to substituted pyrazoles. In some embodiments, the targeting moiety for c-MYC ($M_{c\text{-}MYC}$) may be derived from a substituted pyrazole having a formula which may include, but is not limited to formula I:

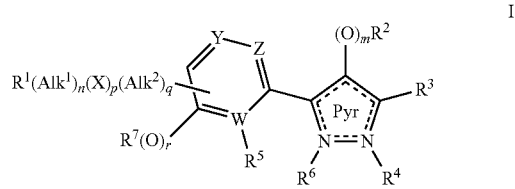

wherein
  $R^1$ is present or absent and when present R is hydrogen, halo, alkyl, alkoxy, hydroxyl, aryl (e.g., phenyl), alkylaryl (e.g., benzyl), heteroaryl (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl, imidazo[1,2-A]pyridine such as imidazo[1,2-A]pyridin-4-yl, imidazo[1,2-A]pyridin-5-yl, imidazo[1,2-A]pyridin-6-yl, imidazo[1,2-A]pyridin-7-yl, imidazo[1,2-A]pyridin-8-yl, or imidazo[1,2-A]pyridin-9-yl), cycloalkyl (e.g., cyclohexyl), or cycloheteroalkyl (e.g., piperidinyl such as N-piperidinyl, piperidin-2-yl, piperidin-3-yl, or piperidin-4-yl; piperazinyl such as N-piperazinyl; morpholinyl such as N-morpholinyl; tetrahydropyranyl such as tetrahydropyran-4-yl), amino, or carboxyamido (or amidocarboxyl), optionally $R^1$ is substituted at one or more positions with one or more of alkyl (e.g., $C_1$-$C_6$ alkyl), alkoxy (e.g., $C_1$-$C_6$ alkoxy), haloalkyl (e.g., trifluoromethyl), haloalkoxy (e.g., trifluoromethoxy), aryl (e.g., phenyl), hydroxyl, halo, cyano, carboxyamido (or amidocarboxyl), hydrazonyl, carbonyl, carboxyl, and alkoxycarbonyl;
  $Alk^1$ is straight-chain or branched alkylenyl (e.g., a diradical of a straight-chain or branched $C_1$-$C_6$ alkyl group);
  n is 0 or 1;
  X is O, NH, $N(R^8)$, $N(R^8)CH(O)$, or $CH(O)N(R^8)$;
  p is 0 or 1;
  $Alk^2$ is straight-chain or branched alkylenyl (e.g., a diradical of a straight-chain or branched $C_1$-$C_6$ alkyl group);
  q is 0 or 1;
  Y is CH, C-halo (e.g., C—F, C—Br, C—Cl, or C—I), C-haloalkyl (e.g., C—$CF_3$), or N;

Z is CH, C-halo (e.g., C—F, C—Br, C—Cl, or C—I), C-haloalkyl (e.g., C—CF$_3$), or N;

m is 0 or 1;

R$^2$ is hydrogen or halo, or R$^2$ is alkyl, aryl (e.g., phenyl), alkylaryl (e.g., benzyl), heteroaryl (e.g., N-pyridinyl, pyridin-2-yl, pyridin-3-yl, pyridin-4-yl, pyrazol-1-yl, pyrazol-3-yl, pyrazol-4-yl, 1,3-benzodioxol-5-yl, 1,3-benzodioxol-6-yl, furan-2-yl, furan-3-yl), cycloalkyl (e.g., cyclohexyl), or cycloheteroalkyl (e.g., piperidinyl, morpholinyl), optionally R$^2$ is substituted at one or more positions with one or more of alkyl (e.g., C$_1$-C$_6$ alkyl), alkoxy (e.g., C$_1$-C$_6$ alkoxy), haloalkyl (e.g., trifluoromethyl), haloalkoxy (e.g., trifluoromethoxy), hydroxyl, halo, cyano, carboxyamido (or amidocarboxyl), hydrazonyl, carbonyl, carboxyl, and alkoxycarbonyl;

R$^3$ is hydrogen, alkyl (e.g., C$_1$-C$_6$ alkyl), alkoxy (e.g., C$_1$-C$_6$ alkoxy), haloalkyl (e.g., trifluoromethyl), haloalkoxy (e.g., trifluoromethoxy), aryl (e.g., phenyl), alkylaryl (e.g., benzyl), hydroxyl, halo, carboxyamido (or amidocarboxyl), hydrazonyl, carbonyl, carboxyl, or alkoxycarbonyl;

R$^4$ is present or absent and when present R$^4$ is hydrogen, amino, alkyl, or R$^4$ is aryl (e.g., phenyl), or alkylaryl (e.g., benzyl); R$^4$ optionally is substituted at one or more positions with one or more of alkyl (e.g., C$_1$-C$_6$ alkyl), alkoxy (e.g., C$_1$-C$_6$ alkoxy), haloalkyl (e.g., trifluoromethyl), haloalkoxy (e.g., trifluoromethoxy), aryl (e.g., phenyl), hydroxyl, halo, cyano, carboxyamido (or amidocarboxyl), hydrazonyl, carbonyl, carboxyl, alkoxycarbonyl, aryloxy (e.g., phenoxy), and alkylaryloxy (e.g., benzyloxy);

W is C or N;

R$^5$ is present or absent and when present R$^5$ is hydrogen, alkyl (e.g., C$_1$-C$_6$ alkyl), alkoxy (e.g., C$_1$-C$_6$ alkoxy), haloalkyl (e.g., trifluoromethyl), haloalkoxy (e.g., trifluoromethoxy), hydroxyl, or halo;

R$^6$ is present or absent and when present R$^6$ is hydrogen, amino, alkyl, or R$^6$ is aryl (e.g., phenyl) or alkylaryl (e.g., benzyl); R$^6$ optionally is substituted at one or more positions with one or more of alkyl (e.g., C$_1$-C$_6$ alkyl), alkoxy (e.g., C$_1$-C$_6$ alkoxy), haloalkyl (e.g., trifluoromethyl), haloalkoxy (e.g., trifluoromethoxy), aryl (e.g., phenyl), hydroxyl, halo, cyano, carboxyamido (or amidocarboxyl), hydrazonyl, carbonyl, carboxyl, alkoxycarbonyl, aryloxy (e.g., phenoxy), and alkylaryloxy (e.g., benzyloxy), or R$^6$ and R$^5$ together form a ring structure having a formula

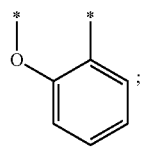

r is 0 or 1;

R$^7$ is hydrogen or halo, or R$^7$ is alkyl, aryl (e.g., phenyl), alkylaryl (e.g., benzyl), heteroaryl (e.g., N-pyridinyl, pyridin-2-yl, pyridin-3-yl, pyridin-4-yl, pyrazol-1-yl, pyrazol-3-yl, pyrazol-4-yl, pyrimidinyl (e.g., pyrimidin-2-yl, pyrimidin-4-yl, pyrimidin-5-yl, or pyrimidin-6-yl), 1,3-benzodioxol-5-yl, 1,3-benzodioxol-6-yl, furan-2-yl, furan-3-yl), cycloalkyl (e.g., cyclohexyl), or cycloheteroalkyl (e.g., piperidinyl, morpholinyl), optionally R$^7$ is substituted at one or more positions with one or more of alkyl (e.g., C$_1$-C$_6$ alkyl), alkoxy (e.g., C$_1$-C$_6$ alkoxy), haloalkyl (e.g., trifluoromethyl), haloalkoxy (e.g., trifluoromethoxy), hydroxyl, halo, cyano, carboxyamido (or amidocarboxyl), hydrazonyl, carbonyl, carboxyl, and alkoxycarbonyl;

R$^8$ is hydrogen, alkyl, aryl, or alkylaryl optionally substituted with halo; and with the proviso that at least one of R$^4$ and R$^6$ is absent;

optionally with the proviso that if R$^5$ is hydrogen, then p is 1 and m is 1;

optionally with the proviso that if R$^1$(Alk$^1$)$_n$(X)$_p$(Alk$^2$)$_q$- is hydrogen, hydroxyl, or alkyl, and R$^5$ is hydroxyl, then m is 1, or at least one of R$^2$ and R$^3$ is not hydrogen; and optionally with the proviso that no more than 2 of W, Y, and Z are N.

In the disclosed formula I, Pyr is a pyrazole ring having two non-adjacent double bonds, for example, where the substituted pyrazoles have a formula I(i) or I(ii):

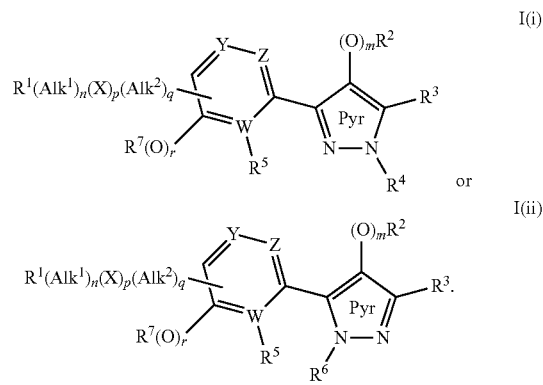

The c-MYC targeting moiety of the disclosed PROTACs (M$_{c\text{-}MYC}$) typically is linked via a bond or a linker (L) to a second targeting moiety that binds to an E3 ubiquitin ligase (M$_{E3}$). The c-MYC targeting moiety may comprise a radical form of a compound of a formula I, I(i), or I(ii), for example wherein the c-MYC moiety is attached to the linker via a radicalized substituent of the moiety R$^1$(Alk$^1$)$_n$(X)$_p$(Alk$^2$)$_q$ (for example, a radicalized R$^1$, Alk$^1$, X, or Alk$^2$ substituent of formula I, I(i), or I(ii).

Suitable linkers for the disclosed PROTACs may include, but are not limited to linkers comprising a polyethylene glycol moiety. Other suitable linkers for the disclose PROTACS may include an alkylalkyne moiety, and/or an aminoalkyl alkyne moiety.

The E3 ubiquitin ligase targeting moiety of the disclosed PROTACs (M$_{E3}$) typically binds and/or targets the PROTACs to an E3 ubiquitin ligase. Suitable E3 ubiquitin ligases may include, but are not limited to, Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

The E3 ubiquitin ligase targeting moiety of the disclosed PROTACs (M$_{E3}$) typically is derived from a compound that binds to an E3 ubiquitin ligase, for example, as a ligand for an E3 ubiquitin ligase. Suitable ligands may include, but are not limited to, ligands derived from thalidomide, pomalidomide, lenalidomide, VHL ligand 1 (VHL-1), VHL ligand 2

(VHL-2), VH032, VL-269, LCL161, hydroxyproline-based ligands, and HIF-1α-derived (R)-hydroxyproline, including radicalized forms.

The disclosed PROTACs may exhibit one or more biological activities. The disclosed PROTACs may inhibit the growth of cells that express c-MYC (preferably by at a concentration of less than about 100 µM, 50 µM, 10 µM, 1 µM, 0.1 µM, 0.05 µM, 0.01 µM, 0.005 µM, 0.001 µM, or less). The disclosed PROTACs may not inhibit the growth of cells that do not express c-MYC (preferably at a concentration of greater than about 0.001 µM, 0.005 µM, 0.01 µM, 0.5 µM, 0.1 µM, 1.0 µM, 10 µM, and 100 µM or higher).

Also disclosed are pharmaceutical compositions comprising the disclosed PROTACs and a suitable pharmaceutical carrier, excipient, or diluent. The disclosed pharmaceutical compositions may comprise an effective amount of the PROTACs for inhibiting the growth of cancer cells when administered to a subject in need thereof.

Also disclosed are methods for treating cell proliferation diseases and disorders such as cancer. The methods may include administering the disclosed PROTACs s or pharmaceutical compositions comprising the disclosed PROTACs to a subject in need thereof, for example, to a subject having cancer. The disclosed PROTACs or pharmaceutical compositions comprising the disclosed PROTACs may be administered with additional therapeutic agents, optionally in combination, in order to treat cell proliferative diseases and disorders. Cell proliferative diseases and disorders treated by the disclosed methods may include, but are not limited to, cancers selected from the group consisting of multiple myeloma, leukemia, non-small cell lung cancer, colon cancer, cancer of the central nervous system, melanoma, ovarian cancer, renal cancer, prostate cancer, and breast cancer.

BRIEF DESCRIPTION OF THE FIGURES

FIG. 1. Compound identification information including correlation between compound identification number and NU ID number (NUCC-0226 ###).

DETAILED DESCRIPTION

Figure 2:
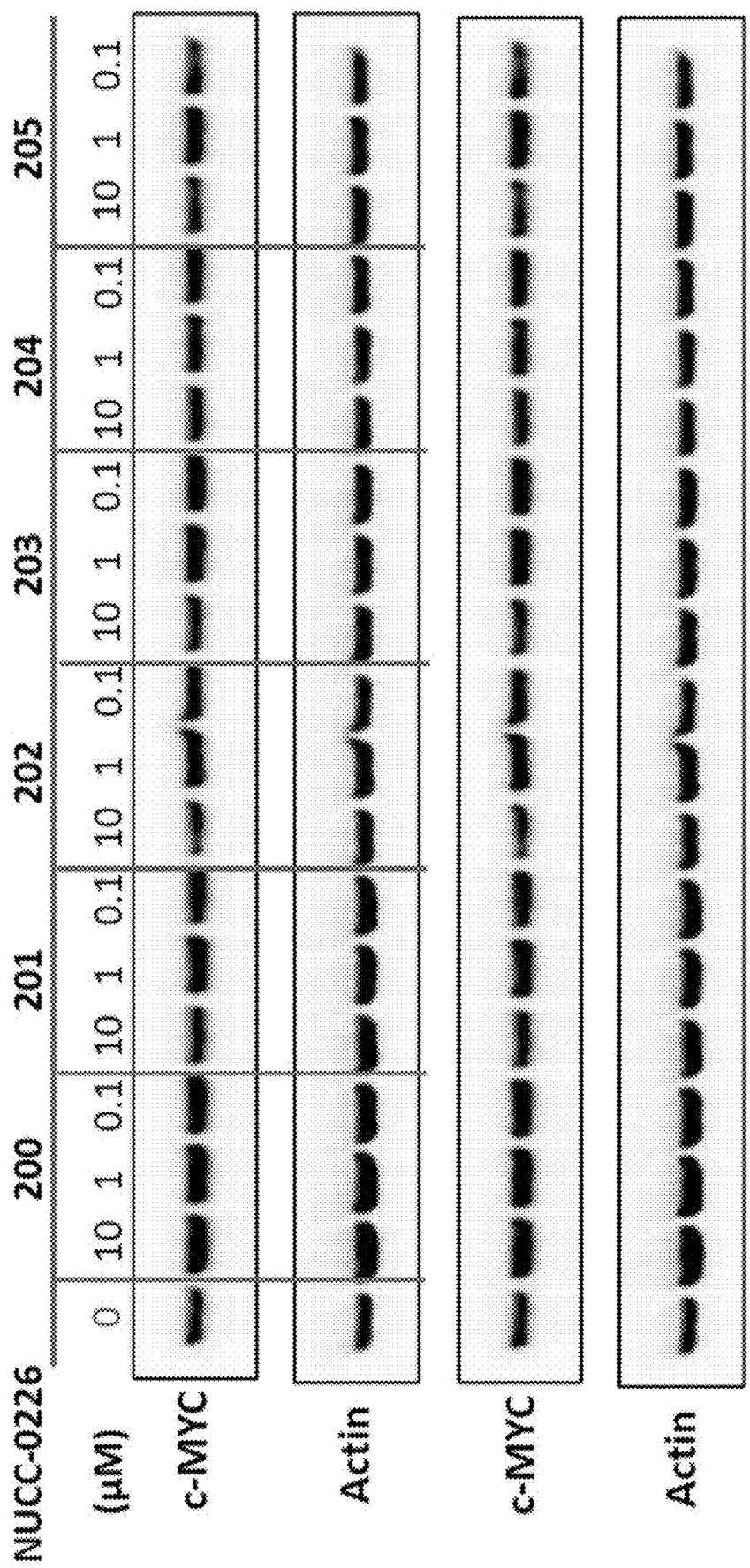
FIG. 2. MYC degradation screen in PC3 cells treated for 24 hours with the listed compounds (200-205) at the listed concentration (10, 1 or 0.1 µM).

The present invention is described herein using several definitions, as set forth below and throughout the application.

Unless otherwise specified or indicated by context, the terms "a", "an", and "the" mean "one or more." For example, "a compound" and "a substituent" and a "moiety" and a "PROTAC" should be interpreted to mean "one or more compounds" and "one or more substituents" and "one or more moieties" and "one or more PROTACs", respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment.

A "subject in need of treatment" may include a subject having a disease, disorder, or condition that is responsive to therapy with a proteolytic-targeted chimeric molecule (PROTAC), which his targeted to c-MYC for degradation of c-MYC. For example, a "subject in need of treatment" may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, and breast cancer). A "subject in need of treatment" may include a subject having a cell proliferative disease, disorder, or condition such as cancer that is associated with c-MYC activity and/or that may be treated by administering an effective amount of an agent that modulates c-MYC activity.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "modulate" means decreasing or inhibiting activity and/or increasing or augmenting activity. For example, modulating c-MYC activity may mean increasing or augmenting c-MYC activity and/or decreasing or inhibiting c-MYC activity. The proteolytic-targeted chimeric molecules (PROTACs) disclosed herein may be administered to modulate c-MYC activity.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched C1-C6 alkyl group). Exemplary alkylene groups include, but are not limited to —$CH_2$—, —$CH_2CH_2$—, —CH$_2$CH$_2$CH$_2$—, —CH(CH$_3$)CH$_2$—, —CH$_2$CH(CH$_3$)CH$_2$—, —CH(CH$_2$CH$_3$)CH$_2$—, and the like.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido (or amidocarboxyl), carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds and molecules (e.g., PROTACs) of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds and molecules may be designated by the symbols "R" or "S," or "+" or "−" depending on the configuration of substituents around the stereogenic carbon atom and or the optical rotation observed. The present invention encompasses various stereo isomers of these compounds and molecules and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds and molecules, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

The formulae of the compounds and molecules disclosed herein should be interpreted as encompassing all possible stereoisomers, enantiomers, or epimers of the compounds and molecules unless the formulae indicates a specific stereoisomer, enantiomer, or epimer. The formulae of the compounds and molecules disclosed herein should be interpreted as encompassing salts, esters, amides, or solvates thereof of the compounds and molecules.

Proteolytic-Targeting Chimeric Molecules (PROTACs) that Induce Degradation of c-MYC Protein Disclosed herein are proteolytic-targeted chimeric molecules (PROTACs) that induce degradation of c-MYC protein. In some embodiments, the disclosed molecules may be described as having a having a formula $M_{c\text{-}MYC}\text{-}L\text{-}M_{E3}$ or alternatively $M_{E3}\text{-}L\text{-}M_{c\text{-}MYC}$, wherein $M_{c\text{-}MYC}$ is a moiety that binds to c-MYC, L is a bond or a linker covalently attaching $M_{MYC}$ and $M_{E3}$, and $M_{E3}$ is a moiety that binds to an E3 ubiquitin ligase. Compounds that bind to c-MYC are disclosed in the prior art and may include, but are not limited to compounds disclosed in U.S. Publication No. 2019/0062281, published on Feb. 28, 2019, the content of which is incorporated herein by reference in its entirety.

In some embodiments of the disclosed PROTACs, $M_{c\text{-}MYC}$ has a formula derived from a compound having formula I (e.g. a radicalized or functionalized form):

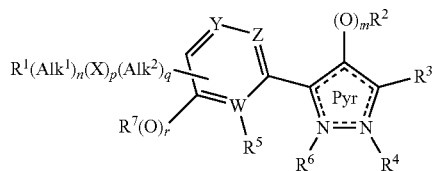

I wherein $R^1$ is present or absent and when present $R^1$ is hydrogen, halo, aryl, alkylaryl, heteroaryl, alkylheteroaryl, cycloalkyl, cycloheteroalkyl, amino, carboxyamido (or amidocarboxy), optionally $R^1$ is substituted at one or more positions with one or more of alkyl, alkoxy, haloalkyl, haloalkoxy, aryl, hydroxyl, halo, cyano, carboxyamido (or amidocarboxyl), hydrazonyl, carbonyl, carboxyl, and alkoxycarbonyl;

$Alk^1$ is straight-chain or branched alkylenyl (e.g., a diradical of a straight-chain or branched $C_1$-$C_6$ alkyl group);

n is 0 or 1;

X is O, NH, N($R^8$), N($R^8$)CH(O), or CH(O)N($R^8$);

p is 0 or 1;

$Alk^2$ is straight-chain or branched alkylenyl (e.g., a diradical of a straight-chain or branched $C_1$-$C_6$ alkyl group);

q is 0 or 1;

Y is CH, C-halo (e.g., C—F, C—Br, C—Cl, or C—I), C-haloalkyl (e.g., C—$CF_3$), or N;

Z is CH, C-halo (e.g., C—F, C—Br, C—Cl, or C—I), C-haloalkyl (e.g., C—$CF_3$), or N;

m is 0 or 1;

$R^2$ is hydrogen, halo, or $R^2$ is alkyl, aryl, alkylaryl, heteroaryl, cycloalkyl, or cycloheteroalkyl, optionally $R^2$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, and alkoxycarbonyl;

$R^3$ is hydrogen, alkyl, alkoxy, haloalkyl, haloalkoxy, alkenyl, aryl, alkylaryl, hydroxyl, halo, carboxyamido (or amidocarboxyl) optionally substituted with alkyl (e.g., N-alkylcarboxyamido or N,N-dialkylcarboxyamido), hydrazonyl, carbonyl, carboxyl, and alkoxycarbonyl;

$R^4$ is present or absent and when present $R^4$ is hydrogen, amino, alkyl, or $R^4$ is aryl or alkylaryl; $R^4$ optionally is substituted at one or more positions with one or more of alkyl, alkoxy, haloalkyl, haloalkoxy, aryl (e.g., phenyl), hydroxyl, halo, cyano, carboxyamido (or amidocarboxyl), hydrazonyl, carbonyl, carboxyl, alkoxycarbonyl, aryloxy, and alkylaryloxy;

W is C or N;

$R^5$ is present or absent and when present $R^5$ is hydrogen, alkyl, alkoxy, haloalkyl, haloalkoxy, hydroxyl, or halo;

$R^6$ is present or absent and when present $R^6$ is hydrogen, amino, alkyl, or $R^6$ is aryl or alkylaryl; $R^6$ optionally is substituted at one or more positions with one or more of alkyl, alkoxy, haloalkyl, haloalkoxy, aryl, hydroxyl, halo, cyano, amido, hydrazonyl, carbonyl, carboxyl, alkoxycarbonyl, aryloxy, and alkylaryloxy, or $R^6$ and $R^5$ together form a ring structure having a formula

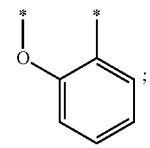

r is 0 or 1;

$R^7$ is hydrogen, halo, or $R^7$ is alkyl, aryl, alkylaryl, heteroaryl, cycloalkyl, or cycloheteroalkyl, optionally $R^7$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, alkoxycarbonyl, oxoaryl, and oxoheteroaryl; and R⁸ is hydrogen, alkyl, aryl, or alkylaryl optionally substituted with halo;
with the proviso that at least one of R⁴ and R⁶ is absent;
optionally with the proviso that if R⁵ is hydrogen, then p is 1 and m is 1;
optionally with the proviso that if R¹(Alk¹)$_n$(X)$_p$(Alk²)$_q$- is hydrogen, hydroxyl, or alkyl, and R⁵ is hydroxyl, then m is 1, or at least one of R² and R³ is not hydrogen; and
optionally with the proviso that no more than two of W, Y, and Z are N.

In other embodiments of the disclosed PROTACS, M$_{c-MYC}$ may have a formula derived from a compound having formula I' (e.g. a functionalized form):

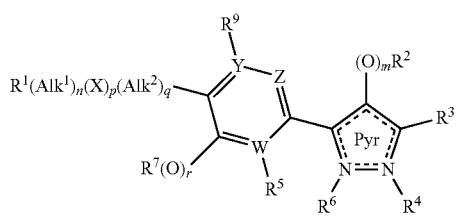

wherein
R¹ is present or absent and when present R is hydrogen, halo, aryl, alkylaryl, heteroaryl, alkylheteroaryl, cycloalkyl, or cycloheteroalkyl, optionally R¹ is substituted at one or more positions with one or more of alkyl, alkoxy, haloalkyl, haloalkoxy, aryl, hydroxyl, halo, cyano, carboxyamido (or amidocarboxyl), hydrazonyl, carbonyl, carboxyl, and alkoxycarbonyl;
Alk¹ is straight-chain or branched alkylenyl (e.g., a diradical of a straight-chain or branched C₁-C₆ alkyl group);
n is 0 or 1;
X is O, NH, N(R⁸), N(R⁸)CH(O), or CH(O)N(R⁸);
p is 0 or 1;
Alk² is straight-chain or branched alkylenyl (e.g., a diradical of a straight-chain or branched C₁-C₆ alkyl group);
q is 0 or 1;
Y is CH, C-halo (e.g., C—F, C—Br, C—Cl, or C—I), C-haloalkyl (e.g., C—CF₃), or N;
Z is CH, C-halo (e.g., C—F, C—Br, C—Cl, or C—I), C-haloalkyl (e.g., C—CF₃), or N;
m is 0 or 1;
R² is hydrogen, halo, or R² is alkyl, aryl, alkylaryl, heteroaryl, cycloalkyl, or cycloheteroalkyl, optionally R² is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, and alkoxycarbonyl;
R³ is hydrogen, alkyl, alkoxy, haloalkyl, haloalkoxy, alkenyl, aryl, alkylaryl, hydroxyl, halo, carboxyamido (or amidocarboxyl) optionally substituted with alkyl (e.g., N-alkylcarboxyamido or N,N-dialkylcarboxyamido), hydrazonyl, carbonyl, carboxyl, and alkoxycarbonyl;
R⁴ is present or absent and when present R⁴ is hydrogen, amino, alkyl, or R⁴ is aryl or alkylaryl; R⁴ optionally is substituted at one or more positions with one or more of alkyl, alkoxy, haloalkyl, haloalkoxy, aryl (e.g., phenyl), hydroxyl, halo, cyano, carboxyamido (or amidocarboxyl), hydrazonyl, carbonyl, carboxyl, alkoxycarbonyl, aryloxy, and alkylaryloxy;
W is C or N;

R⁵ is present or absent and when present R⁵ is hydrogen, alkyl, alkoxy, haloalkyl, haloalkoxy, hydroxyl, or halo;
R⁶ is present or absent and when present R⁶ is hydrogen, amino, alkyl, or R⁶ is aryl or alkylaryl; R⁶ optionally is substituted at one or more positions with one or more of alkyl, alkoxy, haloalkyl, haloalkoxy, aryl, hydroxyl, halo, cyano, amido, hydrazonyl, carbonyl, carboxyl, alkoxycarbonyl, aryloxy, and alkylaryloxy, or R⁶ and R⁵ together form a ring structure having a formula

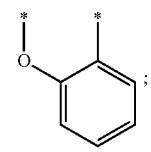

r is 0 or 1;
R⁷ is hydrogen, halo, or R⁷ is alkyl, aryl, alkylaryl, heteroaryl, cycloalkyl, or cycloheteroalkyl, optionally R⁷ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, alkoxycarbonyl, oxoaryl, and oxoheteroaryl; and
R⁸ is hydrogen, alkyl, aryl, or alkylaryl optionally substituted with halo;
R⁹ is hydrogen or halo; and
with the proviso that at least one of R⁴ and R⁶ is absent;
optionally with the proviso that if R⁵ is hydrogen, then p is 1 and m is 1;
optionally with the proviso that if R¹(Alk¹)$_n$(X)$_p$(Alk²)$_q$- is hydrogen, hydroxyl, or alkyl, and R⁵ is hydroxyl, then m is 1, or at least one of R² and R³ is not hydrogen; and
optionally with the proviso that no more than two of W, Y, and Z are N.

In further embodiments of the disclosed PROTACS, M$_{c-MYC}$ may have a formula selected from:

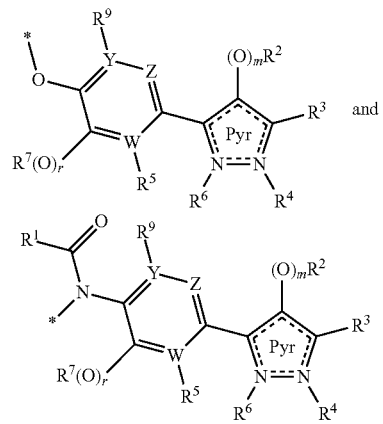

and wherein
R¹ is present or absent and when present R is hydrogen, halo, aryl, alkylaryl, heteroaryl, alkylheteroaryl, cycloalkyl, or cycloheteroalkyl, optionally R¹ is substituted at one or more positions with one or more of alkyl, alkoxy, haloalkyl, haloalkoxy, aryl, hydroxyl, halo, cyano, carboxyamido (or amidocarboxyl), hydrazonyl, carbonyl, carboxyl, and alkoxycarbonyl;

Alk¹ is straight-chain or branched alkylenyl (e.g., a diradical of a straight-chain or branched $C_1$-$C_6$ alkyl group);
n is 0 or 1;
X is O, NH, N($R^8$), N($R^8$)CH(O), or CH(O)N($R^8$);
p is 0 or 1;
Alk² is straight-chain or branched alkylenyl (e.g., a diradical of a straight-chain or branched $C_1$-$C_6$ alkyl group);
q is 0 or 1;
Y is CH, C-halo (e.g., C—F, C—Br, C—Cl, or C—I), C-haloalkyl (e.g., C—$CF_3$), or N;
Z is CH, C-halo (e.g., C—F, C—Br, C—Cl, or C—I), C-haloalkyl (e.g., C—$CF_3$), or N;
m is 0 or 1;
$R^2$ is hydrogen, halo, or $R^2$ is alkyl, aryl, alkylaryl, heteroaryl, cycloalkyl, or cycloheteroalkyl, optionally $R^2$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, and alkoxycarbonyl;
$R^3$ is hydrogen, alkyl, alkoxy, haloalkyl, haloalkoxy, alkenyl, aryl, alkylaryl, hydroxyl, halo, carboxyamido (or amidocarboxyl) optionally substituted with alkyl (e.g., N-alkylcarboxyamido or N,N-dialkylcarboxyamido), hydrazonyl, carbonyl, carboxyl, and alkoxycarbonyl;
$R^4$ is present or absent and when present $R^4$ is hydrogen, amino, alkyl, or $R^4$ is aryl or alkylaryl; $R^4$ optionally is substituted at one or more positions with one or more of alkyl, alkoxy, haloalkyl, haloalkoxy, aryl (e.g., phenyl), hydroxyl, halo, cyano, carboxyamido (or amidocarboxyl), hydrazonyl, carbonyl, carboxyl, alkoxycarbonyl, aryloxy, and alkylaryloxy;
W is C or N;
$R^5$ is present or absent and when present $R^5$ is hydrogen, alkyl, alkoxy, haloalkyl, haloalkoxy, hydroxyl, or halo;
$R^6$ is present or absent and when present $R^6$ is hydrogen, amino, alkyl, or $R^6$ is aryl or alkylaryl; $R^6$ optionally is substituted at one or more positions with one or more of alkyl, alkoxy, haloalkyl, haloalkoxy, aryl, hydroxyl, halo, cyano, amido, hydrazonyl, carbonyl, carboxyl, alkoxycarbonyl, aryloxy, and alkylaryloxy, or $R^6$ and $R^5$ together form a ring structure having a formula

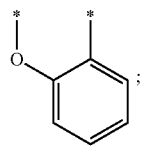

r is 0 or 1;
$R^7$ is hydrogen, halo, or $R^7$ is alkyl, aryl, alkylaryl, heteroaryl, cycloalkyl, or cycloheteroalkyl, optionally $R^7$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, alkoxycarbonyl, oxoaryl, and oxoheteroaryl; and
$R^8$ is hydrogen, alkyl, aryl, or alkylaryl optionally substituted with halo;
$R^9$ is hydrogen or halo; and
with the proviso that at least one of $R^4$ and $R^6$ is absent;
optionally with the proviso that if $R^5$ is hydrogen, then p is 1 and m is 1;
optionally with the proviso that if $R^1(Alk^1)_n(X)_p(Alk^2)_q$- is hydrogen, hydroxyl, or alkyl, and $R^5$ is hydroxyl, then m is 1, or at least one of $R^2$ and $R^3$ is not hydrogen; and
optionally with the proviso that no more than two of W, Y, and Z are N.

In even further embodiments of the disclosed PROTACs, $M_{c-MYC}$ may have a formula selected from:

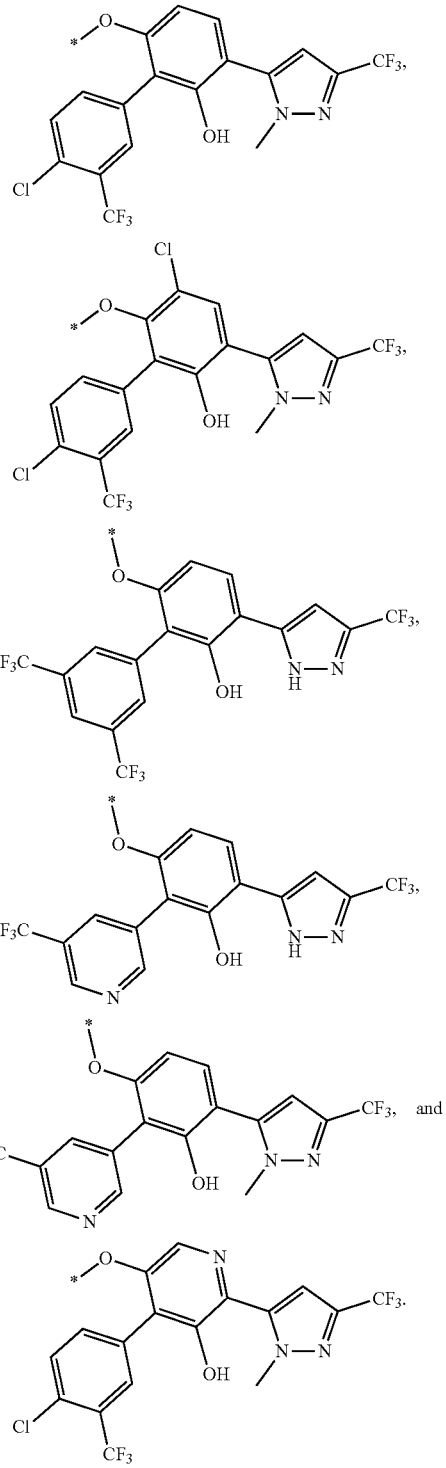

In other embodiments of the disclosed PROTACs, $M_{c-MYC}$ may have a formula:

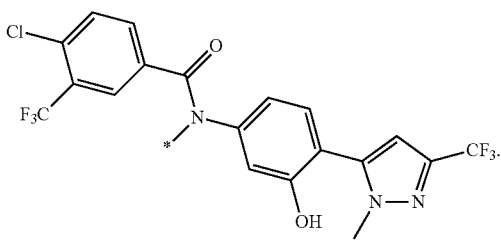 [SMILES: *N(C(=O)c1ccc(Cl)c(C(F)(F)F)c1)c1ccc(-c2cc(C(F)(F)F)nn2C)c(O)c1]

The disclosed PROTACs may include a bond or a linker (L) that conjugates the c-MYC binding moiety ($M_{c-MYC}$) and the E3 ubiquitin ligase binding moiety ($M_{E3}$).

The PROTAC linker connects the functional moieties of a PROTAC, a target protein binder and an E3 ligase recruiter. Linkers used in the development of PROTACs include polyethylene glycol (PEG) linkers, Alkyl-Chain linkers, and Alkyl/ether linkers. Other PROTAC linkers may include those linkers described in one or more of U.S. Publication Nos. 2020/0140456; 2020/0102298; 2020/0085817; 2020/0022966; 2019/0275161; 2019/0263798; 2019/0262502; 2019/0194190; 2019/0151457; 2019/0151295; 2019/0106417; 2019/0076542; 2019/0076541; 2019/0076540; 2019/0076539; 2019/0071415; 2019/0016703; 2018/0327419; 2018/0186785; 2018/0134684; and 2018/0085465; the contents of which are incorporated herein by reference in their entireties.

In some embodiments, the disclosed PROTACs comprise a linker (L) which comprises a polyethylene glycol moiety, an alkylalkyne moiety, and/or an aminoalkyl alkyne moiety that links the c-MYC binding moiety ($M_{c-MYC}$) and the E3 ubiquitin ligase binding moiety ($M_{E3}$).

In some embodiments, the disclosed PROTACs comprise a linker (L) which comprises a formula:

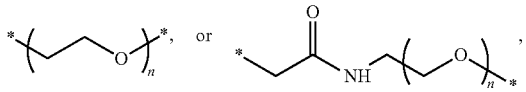

wherein n is ≥2 and optionally less than 20, 18, 16, 14, 12, 10, 8, 6, or 4.

In other embodiments, the disclosed PROTACs comprise a linker (L) which has a formula selected from:

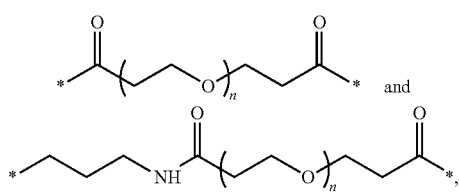

wherein n is ≥2 and optionally less than 20, 18, 16, 14, 12, 10, 8, 6, or 4.

In other embodiments, the disclosed PROTACs comprise a linker (L) which has a formula:

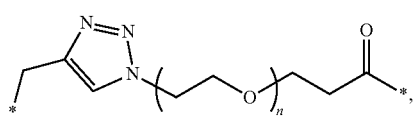

wherein n is ≥2 and optionally less than 20, 18, 16, 14, 12, 10, 8, 6, or 4.

In other embodiments, the disclosed PROTACs comprise a linker (L) which has a formula selected from:

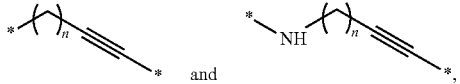

wherein n is ≥2 and optionally less than 20, 18, 16, 14, 12, 10, 8, 6, or 4.

In other embodiments, the disclosed PROTACs comprise a linker (L) which has a formula selected from:

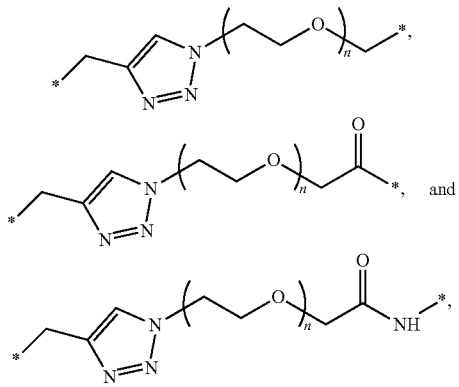

wherein n is ≥2 and optionally less than 20, 18, 16, 14, 12, 10, 8, 6, or 4.

In other embodiments, the disclosed PROTACs comprise a linker (L) which has a formula selected from:

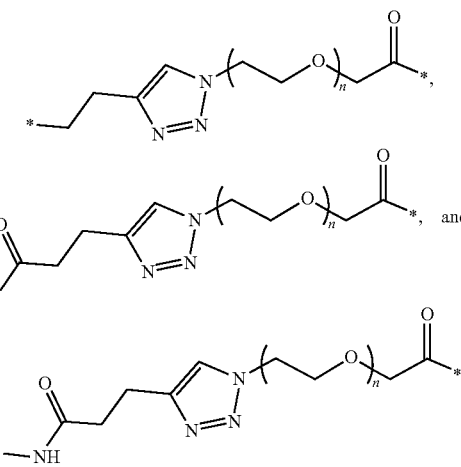

wherein n is ≥2 and optionally less than 20, 18, 16, 14, 12, 10, 8, 6, or 4.

The disclosed PROTACs typically include a moiety that binds to an E3 ubiquitin ligase ($M_{E3}$), for example, as a ligand for the E3 ubiquitin ligase ($M_{E3}$). Ligands for E3 ubiquitin ligases for use in preparing PROTACs are known in the art. (See, e.g., An et al., "Small-molecule PROTACs: An emerging and promising approach for the development of targeted therapy drugs," EBioMedicine. 2018 October;

36: 553-562; and Gu et al., "PROTACs: An Emerging Targeting Technique for Protein Degradation in Drug Discovery," Bioessays. 2018 April; 40(4): e1700247, the contents of which are incorporated herein by reference in their entireties).

In some embodiments of the disclosed PROTACs, $M_{E3}$ is a moiety that binds to an E3 ubiquitin ligase selected from Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

In other embodiments of the disclosed PROTACs, $M_{E3}$ is a moiety derived from thalidomide, pomalidomide, lenalidomide, iberdomide, (S,R,S)-AHPC-Me hydrochloride, (S,R,S)-AHPC-Me dihydrochloride, cereblon modulator 1, thalidomide-propargyl, (S,R,S)-AHPC-propargyl, (S,R,S)-AHPC hydrochloride, CC-885, thalidomide-O—COOH, lenalidomide hemihydrate, thalidomide fluoride, thalidomide-OH, lenalidomide-Br, thalidomide D4, lenalidomide hydrochloride, (S,R,S)-AHPC-Me, cIAP1 ligand 1, TD-106, E3 ligase Ligand 8, E3 ligase Ligand 9, E3 ligase Ligand 10, E3 ligase Ligand 13, E3 ligase Ligand 14, E3 ligase Ligand 18, BC-1215, VHL ligand 1 (VHL-1), VHL ligand 2 (VHL-2), VHL Ligand 8 (VHL-8), VH032, VH032-cyclopropane-F, VH032 thiol, VH-298, VL-269, VL-285, LCL161, hydroxyproline-based ligands, HIF-1α-derived (R)-hydroxyproline, Nutlin carboxylic acid, (4R,5S)-Nutlin carboxylic acid, (S,R,S)-AHPC-Boc, AR antagonist 1, NV03, (S,R,S)-AHPC TFA, (S,R,S)-AHPC, β-Naphthoflavone-CH2-Br, β-Naphthoflavone-CH2-OH, Bestatin-amido-Me, MV-1-NH-Me, (S,S,S)-AHPC hydrochloride, and cIAP1 ligand 2.

In further embodiments of the disclosed PROTACs, $M_{E3}$ has a formula selected from:

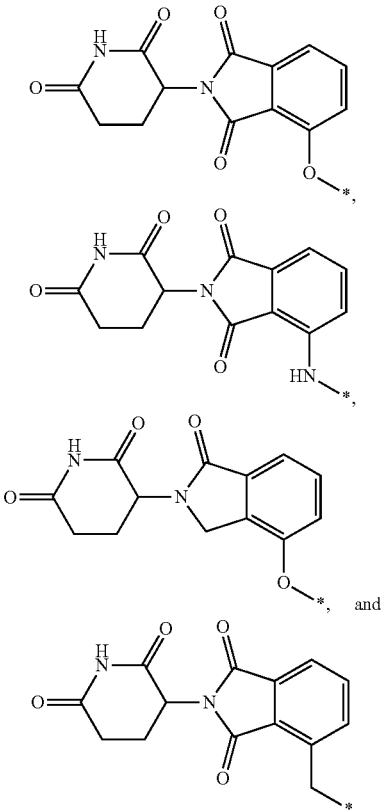

In alternative embodiments of the disclosed PROTACs, $M_{E3}$ has a formula selected from:

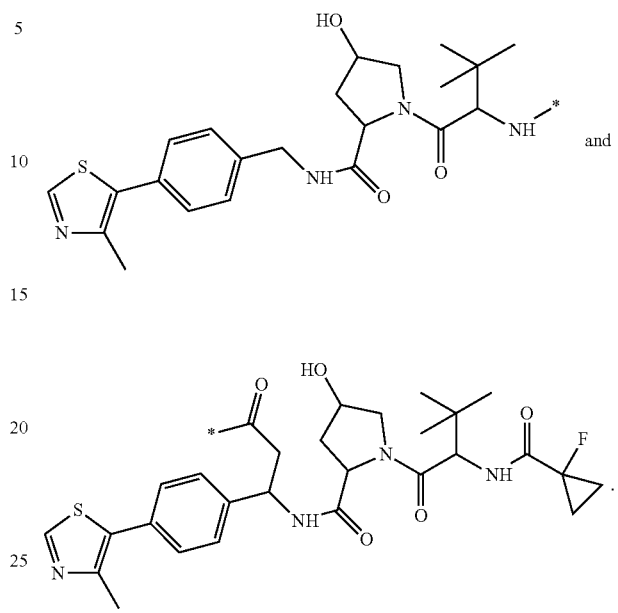

In some embodiments, the disclosed molecules may have formula:

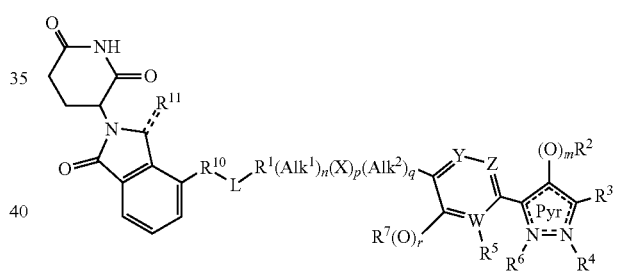

wherein $R^{10}$ is O or NH and $R^{11}$ is absent or present and when present $R^{11}$ is O.

In further embodiments, the disclosed molecules may have a formula.

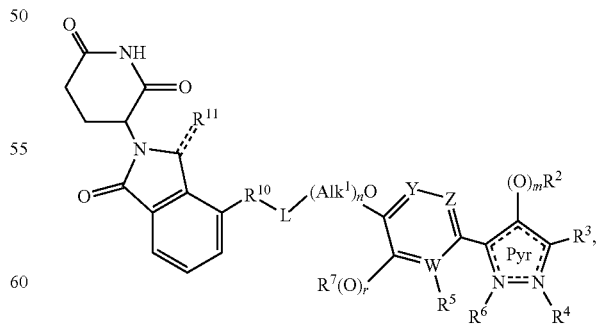

wherein $R^{10}$ is O or NH and $R^{11}$ is absent or present and when present $R^{11}$ is O.

In even further embodiments, the disclosed molecules may have a formula:

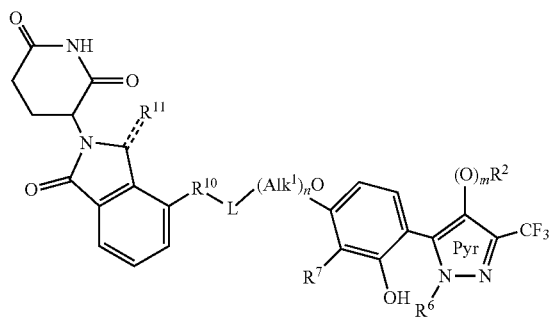

wherein:
  optionally $R^6$ is hydrogen or alkyl;
  optionally $R^7$ is substituted or unsubstituted phenyl or pyridinyl;
  $R^{10}$ is O or NH; and
  $R^{11}$ is absent or present and when present $R^{11}$ is O.

In even further embodiments, the disclosed molecules may have a formula:

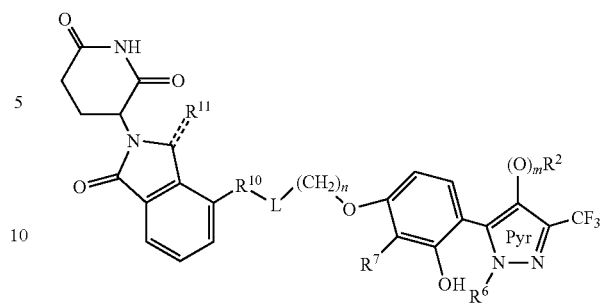

wherein:
  optionally $R^6$ is hydrogen or alkyl;
  optionally $R^7$ is substituted or unsubstituted phenyl or pyridinyl;
  $R^{10}$ is O or NH; and
  $R^{11}$ is absent or present and when present $R^{11}$ is O.

In some embodiments, the disclosed molecules may have a formula:

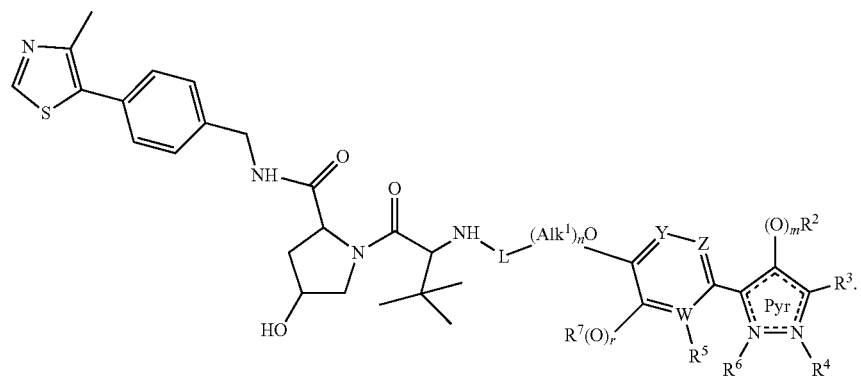

In further embodiments, the disclosed molecules may have a formula:

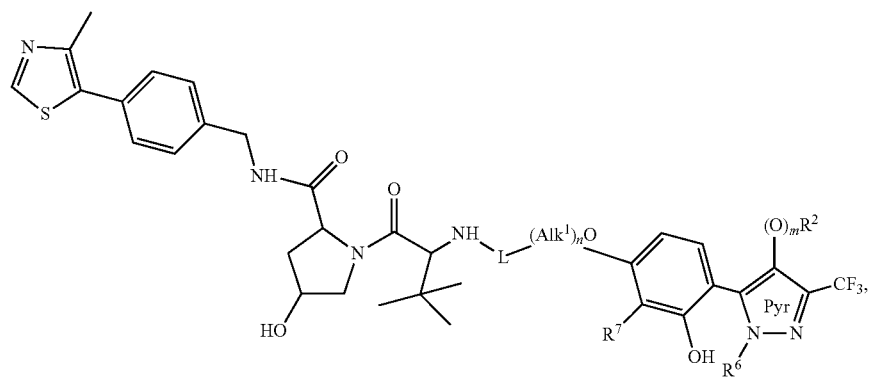

wherein:
optionally $R^6$ is hydrogen or alkyl; and
optionally $R^7$ is substituted or unsubstituted phenyl or pyridinyl.

In even further embodiments, the disclosed molecules may have a formula:

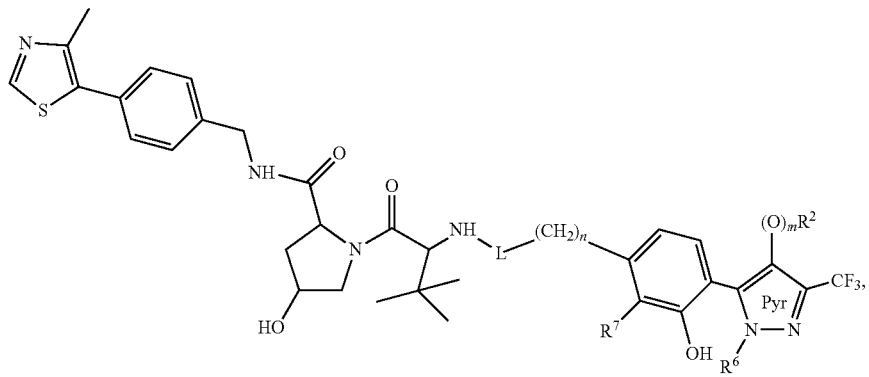

wherein:
optionally $R^6$ is hydrogen or alkyl; and
optionally $R^7$ is substituted or unsubstituted phenyl or pyridinyl.

The disclosed PROTACs may be formulated as pharmaceutical compositions. In some embodiments, pharmaceutical compositions as contemplated herein include a PROTAC as disclosed herein, for example, in an effective amount for treating a disease or disorder associated with c-MYC, and a suitable pharmaceutical carrier, excipient, or diluent.

The disclosed PROTACs and/or pharmaceutical compositions comprising the disclosed PROTACs may be administered to subjects in need thereof, for example, to treat and/or prevent a disease or disorder associated with expression of c-MYC. Suitable diseases or disorders associated with expression of c-MYC may include cell proliferative diseases or disorders such as cancer. Suitable cancers treated and/or prevented in the disclosed methods may include, but are not limited to, multiple myeloma, leukemia, non-small cell lung cancer, colon cancer, cancer of the central nervous system, melanoma, ovarian cancer, renal cancer, prostate cancer, and breast cancer.

Use of the Disclosed Proteolytic-Targeted Chimeric Molecules (PROTACs) for Inhibiting C-MYC Activity The disclosed proteolytic-targeted chimeric molecules (PROTACs) may exhibit one or more biological activities. The disclosed PROTACs may inhibit the growth of cells that express c-MYC (preferably by at least 50%, 60%, 70%, 80%, 90%, 95%, 96%, 97%, 98%, or 99% at a concentration of less than about 100 µM, 50 µM, 10 µM, 1 µM, 0.1 µM, 0.05 µM, 0.01 µM, 0.005 µM, 0.001 µM, or less). The disclosed PROTACs may not inhibit the growth of cells that do not express c-MYC (preferably by not more than 50%, 40%, 30%, 20%, 10%, 5%, 4%, 3%, 2% or less at a concentration of greater than about 0.001 µM, 0.005 µM, 0.01 µM, 0.5 µM, 0.1 µM, 1.0 µM, 10 µM, and 100 µM or higher). Concentration ranges also are contemplated herein, for example, a concentration range bounded by end-point concentrations selected from 0.001 µM, 0.005 µM, 0.01 µM, 0.5 µM, 0.1 µM, 1.0 µM, 10 µM, and 100 µM. Preferably, the disclosed PROTACs may not produce significant DNA damage (e.g., in an rH2AX staining assay at a concentration greater than about 0.001 µM, 0.005 µM, 0.01 µM, 0.1 µM, 1.0 µM, 10 µM, 100 µM, or higher).

The disclosed PROTACs may be effective in inhibiting cell proliferation of cancer cells, including cancer cells that express c-MYC and whose proliferation is inhibiting by inhibiting the biological activity of c-MYC. The disclosed PROTACs may be effective in inhibiting cell proliferation of one or more types of cancer cells including: multiple myeloma cells, such as MM.1S cells; leukemia cells, such as CCRF-CEM, HL-60(TB), MOLT-4, RPMI-8226 and SR; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS: SF-268, SF-295, SF-539, SNB-19, SNB-75 and U251; melanoma cancer cells, such as LOX IMVI, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as DU-145 and PC-3; and breast cancer cells, such as MCF7, MDA-MB-231/ATCC, MDA-MB-468, HS 578T, BT-549 and T-47D.

Cell proliferation and inhibition thereof by the presently disclosed PROTACs may be assessed by cell viability methods disclosed in the art including colorimetric assays that utilize dyes such as MTT, XTT, and MTS to assess cell viability. Preferably, the disclosed PROTACs have an $IC_{50}$ of less than about 10 µM, 5 µM, 1 µM, 0.5 µM, 0.01 µM, 0.005 µM, 0.001 µM or lower in the selected assay.

The disclosed compounds and molecules (e.g., PROTACs) may be formulated as anti-cancer therapeutics, including hematologic malignancies, breast, lung, pancreas and prostate malignancies. The disclosed compounds and molecules also may be formulated as anti-inflammation therapeutics.

The compounds and molecules (e.g., PROTACs) utilized in the methods disclosed herein may be formulated as pharmaceutical compositions that include: (a) a therapeutically effective amount of one or more compounds and molecules as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

The disclosed compounds and molecules and pharmaceutical compositions comprising the disclosed compounds and molecules may be administered in methods of treating a subject in need thereof. For example, in the methods of treatment a subject in need thereof may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, and breast cancer).

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds and molecules may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds and molecules for achieving therapy in the disclosed methods of treatment may include dose levels falling within ranges having as end-points any of these disclosed dose levels (e.g., 500-2000 ng/kg body weight of the subject).

The compounds and molecules utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds and molecules utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds and molecules utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds and molecules such as phenol, or quaternary compounds and molecules such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds and molecules utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds and molecules are formulated as a composition for administration orally (e.g., in a solvent such as 5% DMSO in oil such as vegetable oil).

The compounds and molecules utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds and molecules may be adapted for administration by any appropriate route, for example by the oral (including buccal or sublingual), rectal, nasal, topical (including buccal, sublingual or parenteral), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Combination Therapies and Pharmaceutical Compositions

The disclosed compounds and molecules or pharmaceutical compositions comprising the disclosed compounds and molecules may be administered in methods of treatment. For example, the disclosed compounds and molecules or pharmaceutical compositions comprising the disclosed compounds and molecules may be administered in methods of treating cell proliferative diseases and disorders. Cell proliferative diseases and disorders treated by the disclosed methods may include, but are not limited to, cancers selected from the group consisting of multiple myeloma, leukemia, non-small cell lung cancer, colon cancer, cancer of the central nervous system, melanoma, ovarian cancer, renal cancer, prostate cancer, and breast cancer.

Optionally, the disclosed compounds and molecules or pharmaceutical compositions comprising the disclosed compounds and molecules may be administered with additional therapeutic agents, optionally in combination, in order to treat cell proliferative diseases and disorders. In some embodiments of the disclosed methods, one or more additional therapeutic agents are administered with the disclosed compounds and molecules or with pharmaceutical compositions comprising the disclosed compounds and molecules, where the additional therapeutic agent is administered prior to, concurrently with, or after administering the disclosed compounds and molecules or the pharmaceutical compositions comprising the disclosed compounds and molecules. In some embodiments, the disclosed pharmaceutical composition are formulated to comprise the disclosed compounds and molecules and further to comprise one or more additional therapeutic agents, for example, one or more additional therapeutic agents for treating cell proliferative diseases and disorders.

In some embodiments, additional therapeutic agents may include, but are not limited to, therapeutic agents for treating leukemias and lymphomas, such as acute myeloid leukemia (AML), acute lymphocytic leukemia (ALL), chronic myelogenous leukemia (CML), and non-Hodgkin's lymphoma.

In some embodiments, additional therapeutic agents may include, but are not limited to, antimetabolite antineoplastic agents that inhibit the synthesis of DNA. Suitable antimetabolite antineoplastic agents that inhibit the synthesis of DNA may include, but are not limited to, nucleoside and/or nucleotide derivatives. Suitable nucleoside and/or nucleotide derivatives may include, but are not limited to cytosine arabinoside (ara-C), otherwise called cytarabine.

ILLUSTRATIVE EMBODIMENTS

The following embodiments are illustrative and should not be interpreted to limit the scope of the claims.

Embodiment 1. A molecule having a formula: $M_{c\text{-}MYC}$-L-$M_{E3}$, wherein $M_{c\text{-}MYC}$ is a moiety that binds to c-MYC, L is a bond or a linker covalently attaching $M_{c\text{-}MYC}$ and $M_{E3}$, and $M_{E3}$ is a moiety that binds to an E3 ubiquitin ligase.

Embodiment 2. The molecule of embodiment 1, wherein $M_{c\text{-}MYC}$ has a formula derived from a compound having formula I:

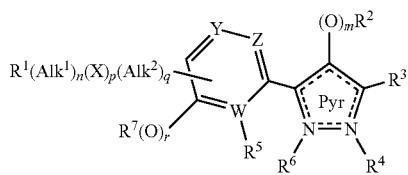

I wherein
Pyr is a pyrazole ring having two non-adjacent double bonds;
$R^1$ is present or absent and when present $R^1$ is hydrogen, aryl, alkylaryl, heteroaryl, alkylheteroaryl, cycloalkyl, cycloheteroalkyl, amino, or carboxyamido (or amidocarboxyl), optionally $R^1$ is substituted at one or more positions with one or more of alkyl, alkoxy, haloalkyl, haloalkoxy, aryl, hydroxyl, halo, cyano, carboxyamido (or amidocarboxyl), hydrazonyl, carbonyl, carboxyl, and alkoxycarbonyl;
$Alk^1$ is straight-chain or branched alkylenyl (e.g., a diradical of a straight-chain or branched $C_1$-$C_6$ alkyl group);
n is 0 or 1;
X is O, NH, $N(R^8)$, $N(R^8)CH(O)$, or $CH(O)N(R^8)$;
p is 0 or 1;
$Alk^2$ is straight-chain or branched alkylenyl (e.g., a diradical of a straight-chain or branched $C_1$-$C_6$ alkyl group);
q is 0 or 1;
Y is CH, C-halo (e.g., C—F, C—Br, C—Cl, or C—I), C-haloalkyl (e.g., C—CF$_3$), or N;
Z is CH, C-halo (e.g., C—F, C—Br, C—Cl, or C—I), C-haloalkyl (e.g., C—CF$_3$), or N;

m is 0 or 1;
$R^2$ is hydrogen, halo, or $R^2$ is alkyl, aryl, alkylaryl, heteroaryl, cycloalkyl, or cycloheteroalkyl, optionally $R^2$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, and alkoxycarbonyl;
$R^3$ is hydrogen, alkyl, alkoxy, haloalkyl, haloalkoxy, alkenyl, aryl, alkylaryl, hydroxyl, halo, carboxyamido (or amidocarboxyl) optionally substituted with alkyl (e.g., N-alkylcarboxyamido or N,N-dialkylcarboxyamido), hydrazonyl, carbonyl, carboxyl, and alkoxycarbonyl;
$R^4$ is present or absent and when present $R^4$ is hydrogen, amino, alkyl, or $R^4$ is aryl or alkylaryl; $R^4$ optionally is substituted at one or more positions with one or more of alkyl, alkoxy, haloalkyl, haloalkoxy, aryl (e.g., phenyl), hydroxyl, halo, cyano, carboxyamido (or amidocarboxyl), hydrazonyl, carbonyl, carboxyl, alkoxycarbonyl, aryloxy, and alkylaryloxy;
W is C or N;
$R^5$ is present or absent and when present $R^5$ is hydrogen, alkyl, alkoxy, haloalkyl, haloalkoxy, hydroxyl, or halo;
$R^6$ is present or absent and when present $R^6$ is hydrogen, amino, alkyl, or $R^6$ is aryl or alkylaryl; $R^6$ optionally is substituted at one or more positions with one or more of alkyl, alkoxy, haloalkyl, haloalkoxy, aryl, hydroxyl, halo, cyano, amido, hydrazonyl, carbonyl, carboxyl, alkoxycarbonyl, aryloxy, and alkylaryloxy, or $R^6$ and $R^5$ together form a ring structure having a formula

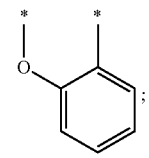

r is 0 or 1;
$R^7$ is hydrogen, halo, or $R^7$ is alkyl, aryl, alkylaryl, heteroaryl, cycloalkyl, or cycloheteroalkyl, optionally $R^7$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, alkoxycarbonyl, oxoaryl, and oxoheteroaryl; and
$R^8$ is hydrogen, alkyl, aryl, or alkylaryl optionally substituted with halo;
with the proviso that at least one of $R^4$ and $R^6$ is absent;
optionally with the proviso that if $R^5$ is hydrogen, then p is 1 and m is 1;
optionally with the proviso that if $R^1(Alk^1)_n(X)_p(Alk^2)_q$- is hydrogen, hydroxyl, or alkyl, and $R^5$ is hydroxyl, then m is 1, or at least one of $R^2$ and $R^3$ is not hydrogen; and
optionally with the proviso that no more than two of W, Y, and Z are N.

Embodiment 3. The molecule of embodiment 1 or 2, wherein $M_{c\text{-}MYC}$ has a formula derived from a compound having formula I':

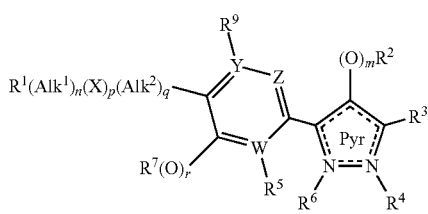

wherein
- $R^1$ is present or absent and present $R^1$ is hydrogen, aryl, alkylaryl, heteroaryl, alkylheteroaryl, cycloalkyl, or cycloheteroalkyl, optionally $R^1$ is substituted at one or more positions with one or more of alkyl, alkoxy, haloalkyl, haloalkoxy, aryl, hydroxyl, halo, cyano, carboxyamido (or amidocarboxyl), hydrazonyl, carbonyl, carboxyl, and alkoxycarbonyl;
- $Alk^1$ is straight-chain or branched alkylenyl (e.g., a diradical of a straight-chain or branched $C_1$-$C_6$ alkyl group);
- n is 0 or 1;
- X is O, NH, $N(R^8)$, $N(R^8)CH(O)$, or $CH(O)N(R^8)$;
- p is 0 or 1;
- $Alk^2$ is straight-chain or branched alkylenyl (e.g., a diradical of a straight-chain or branched $C_1$-$C_6$ alkyl group);
- q is 0 or 1;
- Y is CH, C-halo (e.g., C—F, C—Br, C—Cl, or C—I), C-haloalkyl (e.g., C—$CF_3$), or N;
- Z is CH, C-halo (e.g., C—F, C—Br, C—Cl, or C—I), C-haloalkyl (e.g., C—$CF_3$), or N;
- m is 0 or 1;
- $R^2$ is hydrogen, halo, or $R^2$ is alkyl, aryl, alkylaryl, heteroaryl, cycloalkyl, or cycloheteroalkyl, optionally $R^2$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, and alkoxycarbonyl;
- $R^3$ is hydrogen, alkyl, alkoxy, haloalkyl, haloalkoxy, alkenyl, aryl, alkylaryl, hydroxyl, halo, carboxyamido (or amidocarboxyl) optionally substituted with alkyl (e.g., N-alkylcarboxyamido or N,N-dialkylcarboxyamido), hydrazonyl, carbonyl, carboxyl, and alkoxycarbonyl;
- $R^4$ is present or absent and when present $R^4$ is hydrogen, amino, alkyl, or $R^4$ is aryl or alkylaryl; $R^4$ optionally is substituted at one or more positions with one or more of alkyl, alkoxy, haloalkyl, haloalkoxy, aryl (e.g., phenyl), hydroxyl, halo, cyano, carboxyamido (or amidocarboxyl), hydrazonyl, carbonyl, carboxyl, alkoxycarbonyl, aryloxy, and alkylaryloxy;
- W is C or N;
- $R^5$ is present or absent and when present $R^5$ is hydrogen, alkyl, alkoxy, haloalkyl, haloalkoxy, hydroxyl, or halo;
- $R^6$ is present or absent and when present $R^6$ is hydrogen, amino, alkyl, or $R^6$ is aryl or alkylaryl; $R^6$ optionally is substituted at one or more positions with one or more of alkyl, alkoxy, haloalkyl, haloalkoxy, aryl, hydroxyl, halo, cyano, amido, hydrazonyl, carbonyl, carboxyl, alkoxycarbonyl, aryloxy, and alkylaryloxy, or $R^6$ and $R^5$ together form a ring structure having a formula

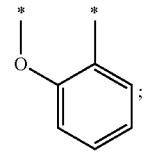

- r is 0 or 1;
- $R^7$ is hydrogen, halo, or $R^7$ is alkyl, aryl, alkylaryl, heteroaryl, cycloalkyl, or cycloheteroalkyl, optionally $R^7$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, alkoxycarbonyl, oxoaryl, and oxoheteroaryl; and
- $R^8$ is hydrogen, alkyl, aryl, or alkylaryl optionally substituted with halo;
- $R^9$ is hydrogen or halo; and
- with the proviso that at least one of $R^4$ and $R^6$ is absent;
- optionally with the proviso that if $R^5$ is hydrogen, then p is 1 and m is 1;
- optionally with the proviso that if $R^1(Alk^1)_n(X)_p(Alk^2)_q$- is hydrogen, hydroxyl, or alkyl, and $R^5$ is hydroxyl, then m is 1, or at least one of $R^2$ and $R^3$ is not hydrogen; and
- optionally with the proviso that no more than two of W, Y, and Z are N.

Embodiment 4. The molecule of any of the foregoing embodiments, wherein $M_{c\text{-}MYC}$ has a formula selected from:

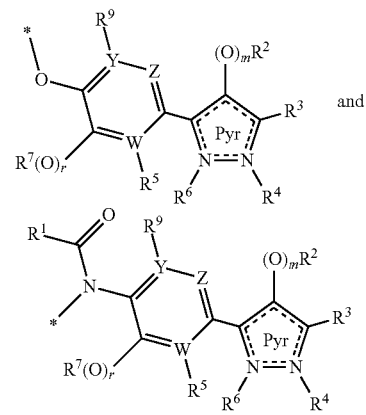

wherein
- $R^1$ is present or absent and when present $R^1$ is hydrogen, aryl, alkylaryl, heteroaryl, alkylheteroaryl, cycloalkyl, or cycloheteroalkyl, optionally $R^1$ is substituted at one or more positions with one or more of alkyl, alkoxy, haloalkyl, haloalkoxy, aryl, hydroxyl, halo, cyano, carboxyamido (or amidocarboxyl), carboxyl, and alkoxycarbonyl;
- $Alk^1$ is straight-chain or branched alkylenyl (e.g., a diradical of a straight-chain or branched $C_1$-$C_6$ alkyl group);
- n is 0 or 1;
- X is O, NH, $N(R^8)$, $N(R^8)CH(O)$, or $CH(O)N(R^8)$;
- p is 0 or 1;
- $Alk^2$ is straight-chain or branched alkylenyl (e.g., a diradical of a straight-chain or branched $C_1$-$C_6$ alkyl group);
- q is 0 or 1;

Y is CH, C-halo (e.g., C—F, C—Br, C—Cl, or C—I), C-haloalkyl (e.g., C—CF$_3$), or N;

Z is CH, C-halo (e.g., C—F, C—Br, C—Cl, or C—I), C-haloalkyl (e.g., C—CF$_3$), or N;

m is 0 or 1;

$R^2$ is hydrogen, halo, or $R^2$ is alkyl, aryl, alkylaryl, heteroaryl, cycloalkyl, or cycloheteroalkyl, optionally $R^2$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, and alkoxycarbonyl;

$R^3$ is hydrogen, alkyl, alkoxy, haloalkyl, haloalkoxy, alkenyl, aryl, alkylaryl, hydroxyl, halo, carboxyamido (or amidocarboxyl) optionally substituted with alkyl (e.g., N-alkylcarboxyamido or N,N-dialkylcarboxyamido), hydrazonyl, carbonyl, carboxyl, and alkoxycarbonyl;

$R^4$ is present or absent and when present $R^4$ is hydrogen, amino, alkyl, or $R^4$ is aryl or alkylaryl; $R^4$ optionally is substituted at one or more positions with one or more of alkyl, alkoxy, haloalkyl, haloalkoxy, aryl (e.g., phenyl), hydroxyl, halo, cyano, carboxyamido (or amidocarboxyl), hydrazonyl, carbonyl, carboxyl, alkoxycarbonyl, aryloxy, and alkylaryloxy;

W is C or N;

$R^5$ is present or absent and when present $R^5$ is hydrogen, alkyl, alkoxy, haloalkyl, haloalkoxy, hydroxyl, or halo;

$R^6$ is present or absent and when present $R^6$ is hydrogen, amino, alkyl, or $R^6$ is aryl or alkylaryl; $R^6$ optionally, substituted at one or more positions with one or more of alkyl, alkoxy, haloalkyl, haloalkoxy, aryl, hydroxyl, halo, cyano, amido, hydrazonyl, carbonyl, carboxyl, alkoxycarbonyl, aryloxy, and alkylaryloxy, or $R^6$ and $R^5$ together form a ring structure having a formula

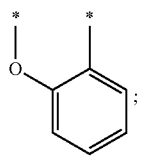

r is 0 or 1;

$R^7$ is hydrogen, halo, or $R^7$ is alkyl, aryl, alkylaryl, heteroaryl, cycloalkyl, or cycloheteroalkyl, optionally $R^7$ is substituted at one or more positions with one or more of alkyl, alkoxy, haloalkyl, haloalkoxy, hydroxyl, halo, cyano, carboxyamido (or amidocarboxyl), hydrazonyl, carbonyl, carboxyl, alkoxycarbonyl, oxoaryl, and oxoheteroaryl; and $R^8$ is hydrogen, alkyl, aryl, or alkylaryl optionally substituted with halo;

$R^9$ is hydrogen or halo; and with the proviso that at least one of $R^4$ and $R^6$ is absent;

optionally with the proviso that if $R^5$ is hydrogen, then p is 1 and m is 1;

optionally with the proviso that if $R^1(Alk^1)_n(X)_p(Alk^2)_q$- is hydrogen, hydroxyl, or alkyl, and $R^5$ is hydroxyl, then m is 1, or at least one of $R^2$ and $R^3$ is not hydrogen; and optionally with the proviso that no more than two of W, Y, and Z are N.

Embodiment 5. The molecule of any of the foregoing embodiments, wherein M$_{c-MYC}$ has a formula selected from:

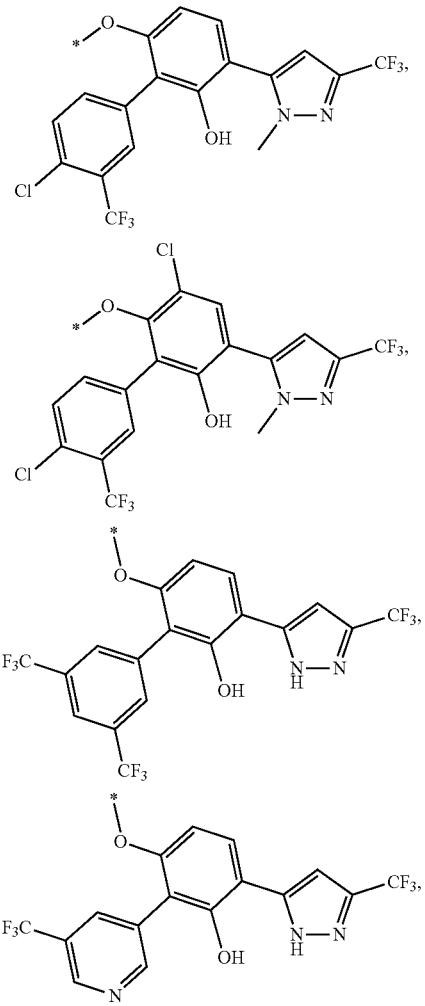

Embodiment 6. The molecule of any of the foregoing embodiments, wherein M$_{c-MYC}$ has a formula:

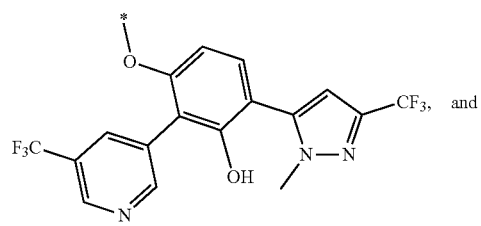

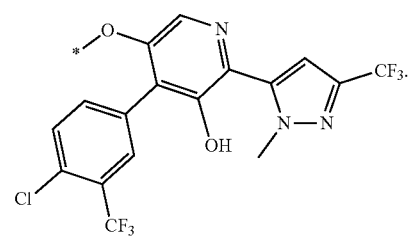

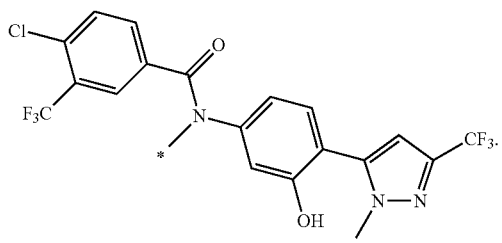 [SMILES: CN(C(=O)c1ccc(Cl)c(C(F)(F)F)c1)c1ccc(-c2cc(C(F)(F)F)nn2C)c(O)c1]

Embodiment 7. The molecule of any of the foregoing embodiments, wherein L comprises a polyethylene glycol moiety, an alkylalkyne moiety, and/or an aminoalkyl alkyne moiety.

Embodiment 8. The molecule of any of the foregoing embodiments, wherein L comprises:

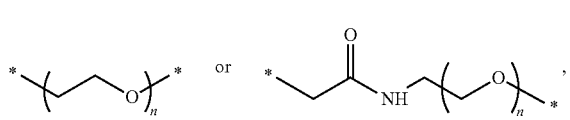

wherein n is ≥2 and optionally less than 20, 18, 16, 14, 12, 10, 8, 6, or 4.

Embodiment 9. The molecule of any of the foregoing embodiments, wherein L has a formula selected from:

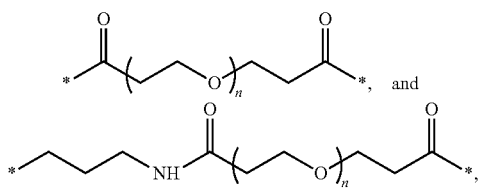

wherein n is ≥2 and optionally less than 20, 18, 16, 14, 12, 10, 8, 6, or 4.

Embodiment 10. The molecule of any of the foregoing embodiments, wherein L has a formula:

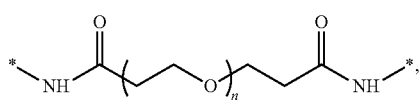

wherein n is ≥2 and optionally less than 20, 18, 16, 14, 12, 10, 8, 6, or 4.

Embodiment 11. The molecule of any of the foregoing embodiments, wherein L has a formula:

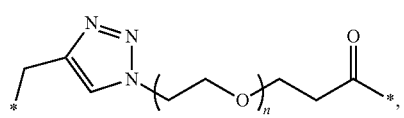

wherein n is ≥2 and optionally less than 20, 18, 16, 14, 12, 10, 8, 6, or 4.

Embodiment 12. The molecule of any of the foregoing embodiments, wherein L has a formula selected from:

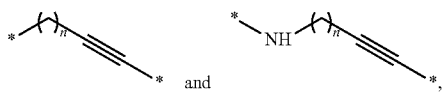

wherein n is ≥2 and optionally less than 20, 18, 16, 14, 12, 10, 8, 6, or 4.

Embodiment 13. The molecule of any of the foregoing embodiments, wherein L has a formula selected from:

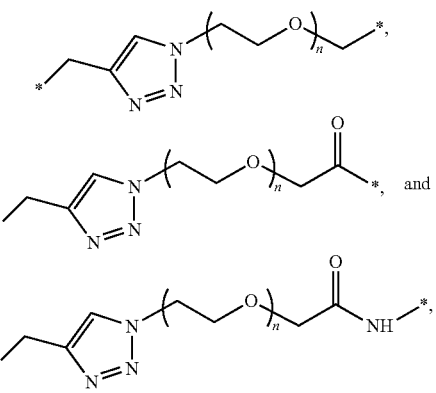

wherein n is ≥2 and optionally less than 20, 18, 16, 14, 12, 10, 8, 6, or 4.

Embodiment 14. The molecule of any of the foregoing embodiments, wherein L has a formula selected from:

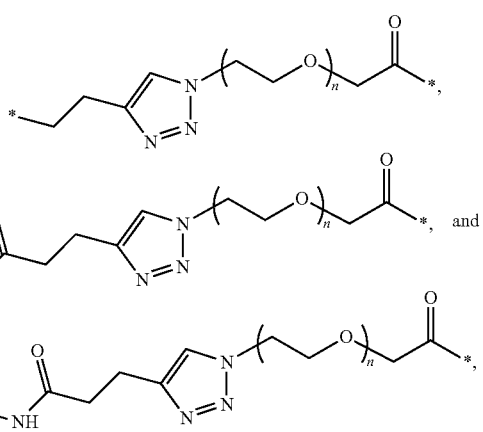

wherein n is ≥2 and optionally less than 20, 18, 16, 14, 12, 10, 8, 6, or 4.

Embodiment 15. The molecule of any of the foregoing embodiments, wherein $M_{E3}$ is a moiety that binds to an E3 ubiquitin ligase selected from Von Hippel-Lindau (VHL) E3 ubiquitin ligase, cereblon (CRBN) E3 ubiquitin ligase, inhibitor of apoptosis protein (IAP) E3 ubiquitin ligase, and mouse double minute 2 homolog (MDM2) E3 ubiquitin ligase.

Embodiment 16. The molecule of any of the foregoing embodiments, wherein $M_{E3}$ is a moiety derived from thalidomide, pomalidomide, lenalidomide, VHL ligand 1 (VHL-1), VHL ligand 2 (VHL-2), VH032, VL-269, LCL161, hydroxyproline-based ligands, or HIF-1α-derived (R)-hydroxyproline.

Embodiment 17. The molecule of any of the foregoing embodiments, wherein $M_{E3}$ has a formula selected from:

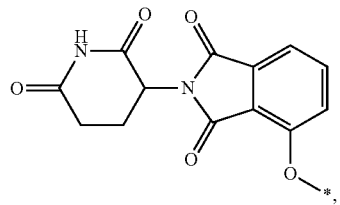

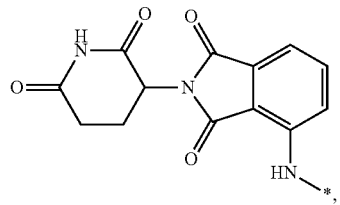

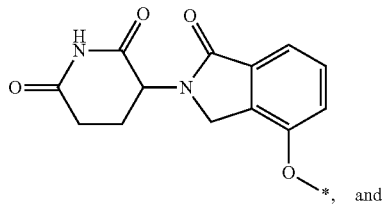

, and

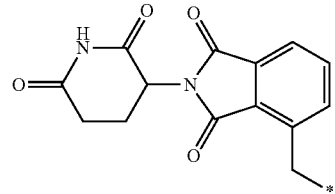

Embodiment 18. The molecule of any of the foregoing embodiments, wherein $M_{E3}$ has a formula selected from:

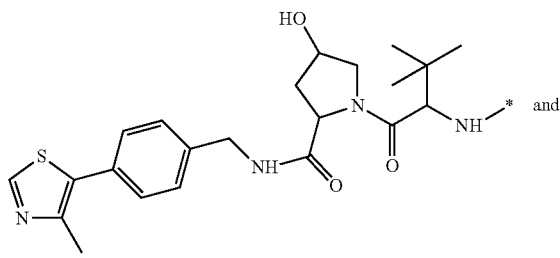 and

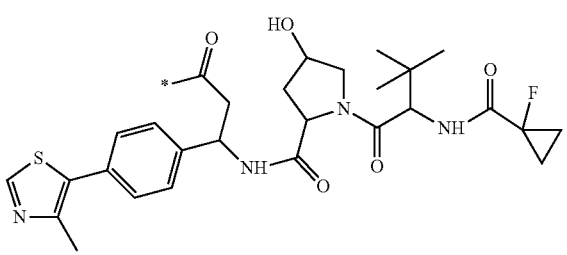

Embodiment 19. The molecule of any of the foregoing embodiments having a formula:

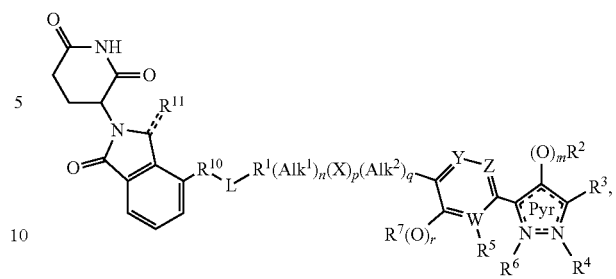

wherein $R^{10}$ is O or NH and $R^{11}$ is absent or present and when present $R^{11}$ is O.

Embodiment 20. The molecule of any of the foregoing embodiments, wherein the compound has a formula:

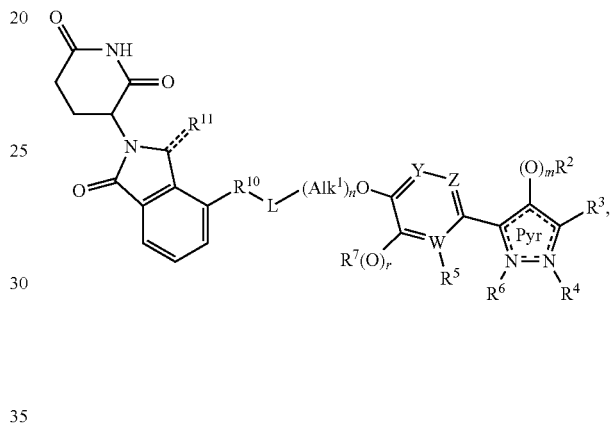

wherein $R^{10}$ is O or NH and $R^{11}$ is absent or present and when present $R^{11}$ is O.

Embodiment 21. The molecule of any of the foregoing embodiments, wherein the compound has a formula:

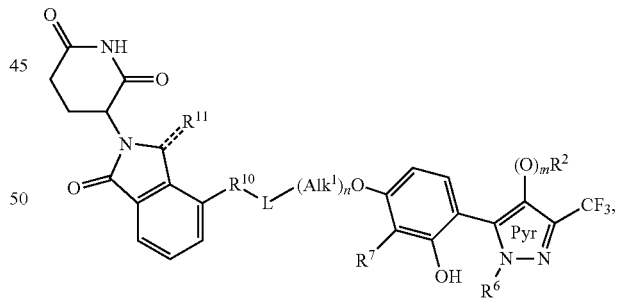

wherein:
optionally $R^6$ is hydrogen or alkyl;
optionally $R^7$ is substituted or unsubstituted phenyl or pyridinyl;
$R^{10}$ is O or NH; and
$R^{11}$ is absent or present and when present $R^{11}$ is O.

Embodiment 22. The molecule of any of the foregoing embodiments, wherein the compound has a formula:

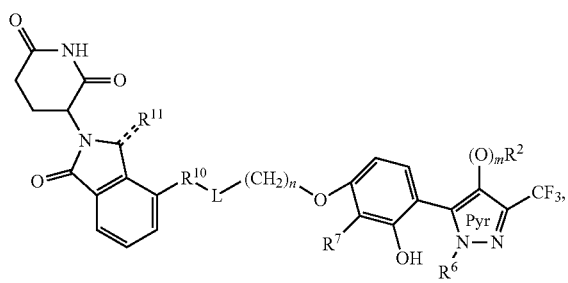

wherein:
optionally $R^6$ is hydrogen or alkyl;
optionally $R^7$ is substituted or unsubstituted phenyl or pyridinyl;
$R^{10}$ is O or NH; and
$R^{11}$ is absent or present and when present $R^{11}$ is O.

Embodiment 23. A pharmaceutical composition comprising a molecule of any of the foregoing claims and a suitable pharmaceutical carrier, excipient, or diluent.

Embodiment 24. A method of treating a disease or disorder associated with expression of c-MYC, the method comprising administering the composition of claim 23 to the subject having a disease or disorder associated with expression of c-MYC.

Embodiment 25. The method of claim 24, wherein the disease or disorder is a cell proliferative disease or disorder.

Embodiment 26. The method of claim 24, wherein the disease or disorder is cancer.

Embodiment 27. The method of claim 26, wherein the cancer is selected from multiple myeloma, leukemia, non-small cell lung cancer, colon cancer, cancer of the central nervous system, melanoma, ovarian cancer, renal cancer, prostate cancer, and breast cancer.

EXAMPLES

The following examples are illustrative and should not be interpreted to limit the scope of the claimed subject matter.

Example 1—Compounds that Induce Degradation of c-MYC Protein

Introduction

The c-Myc oncogene is de-regulated and plays a causal role in a majority of human cancer and c-Myc inhibition profoundly affects tumor growth or survival in multiple models. MYC is the most common oncogene in human cancers and is overexpressed in 30% of all cancers. Therefore, developing c-Myc inhibitors is among the most attractive potential anti-cancer strategies. Unfortunately, due to the difficulty in targeting transcription factors with small molecules, c-Myc is currently regarded as "undruggable".

We have developed a new approach to targeting c-MYC and previously developed a series of new small molecule inhibitors that bind to c-MYC. (See U.S. Publication No. Reference is made to U.S. Publication No. 2019/0062281, published on Feb. 28, 2019, the content of which is incorporated herein by reference in its entirety). Using these compounds as c-MYC binding moieties, we created proteolytic-targeted chimeric molecules (PROTACs) that also include a ligand that binds to an E3 ubiquitin ligase protein, and thereby cause degradation of c-MYC protein.

Synthesis
Step 1

Over a suspension of 1-(2,4-dihydroxyphenyl)ethan-1-one (5.00 g, 32.89 mmol, 1 equiv.) in trifluoroacetic anhydride (18.50 mL, 131.56 mmol, 4 equiv.) placed in a high-pressure tube, sodium 2,2,2-trifluoroacetate (9.84 g, 72.36 mmol, 2.2 equiv.) was added and the system was capped and stirred at 110° C. for 24 h. The reaction was allowed to cool down to approximately 70° C. and then was diluted with 200 mL of EtOAc. The mixture was neutralized by adding saturated aqueous $K_2CO_3$ solution until no more bubbling was observed. Layers were separated and the aqueous phase was extracted with more EtOAc (3×150 mL). The combined organic layers were washed with brine and dried over anhydrous $Na_2SO_4$. The solution was then concentrated to 100-150 mL of EtOAc. Then the flask was capped and kept at room temperature for 1-2 days, obtaining a solid which was filtrated and dried under vacuum to obtain 4.09 g of pure 1 as a white solid in 54% yield.

Then, over a solution of the solid obtained (4 g, 17.31 mmol, 1 equiv.) and iodine (17.57 g, 69.24 mmol, 4 equiv.) in 110 mL of $CHCl_3$, pyridine (5.59 mL, 69.24 mmol, 4 equiv.) were added. The resulting solution was stirred at room temperature for 16 h. Then, 120 mL of saturated aqueous $Na_2S_2O_3$ were added and the resulting mixture stirred for one hour. The organic layer was separated and the aqueous phase was extracted with $CH_2Cl_2$ (3×100 mL). The combined organic layers were washed with brine and dried over anhydrous $Na_2SO_4$. Solvent was then removed under reduced pressure and the residue was triturated with diethyl ether several times to obtain a pale white solid in 90% yield (5.55 g, 15.60 mmol): mp 205-206° C. $^1H$ NMR (500 MHz, $CDCl_3$) δ 8.11 (dd, J=8.9, 1.0 Hz, 1H), 7.15 (dd, J=8.9, 1.0 Hz, 1H), 6.77-6.69 (m, 1H), 6.36 (s, 1H) ppm. $^{13}C$ NMR (126 MHz, $CDCl_3$) δ 175.8, 161.5, 156.0, 152.5 (q, $^2J$=39.1 Hz), 128.1, 119.0, 118.6 (q, $^1J$=272.2 Hz), 117.5, 114.7, 110.9 ppm. LRMS (EI): mass calc for $C_{10}H_5F_3IO_3^+$ $[M+H]^+$ =356.9, found=357.1.

Step 2

A suspension of 7-hydroxy-3-iodo-2-(trifluoromethyl)-4H-chromen-4-one, (1 g, 2.8 mmol, 1 equiv.), the haloalkane (3.4 mmol, 1.2 equiv.) and $K_2CO_3$ (0.77 g, 5.6 mmol, 2 equiv.) in 5 mL of acetone was heated at 60° C. for 16 h. The reaction was filtered through a funnel and the solvent removed under reduced pressure. The crude residue was triturated with water and dried under reduced pressure until dryness.

Step 3

A suspension of the previous alkylated chromenone (0.34 mmol, 1 equiv.), with the corresponding boronic acid (0.37 mmol, 1.1 equiv.), $Na_2CO_3$ (0.68 mmol, 2 equiv.) and $Pd(dppf)Cl_2$ (0.026 mmol, 0.08 equiv.) in 3.5 mL of a mixture 1:2:6 of EtOH:water:toluene was bubbled with nitrogen gas for 10 minutes. Then, the flask was capped, and the mixture was heated at 90° C. for 2 h. The dark solution was cool down to room temperature and diluted with EtOAc. The organic layer was separated and the aqueous phase was extracted with EtOAc (3×3 mL). The combined organic layers were washed with brine and dried over anhydrous $Na_2SO_4$. Solvent was then removed under reduced pressure and the residue was purified by silica gel chromatography.

Step 4

A solution of the previous chromenone (0.2 mmol, 1 equiv.) with the desired hydrazine (0.6 mmol, 3 equiv.) in 2 mL of EtOH was heated at 70° C. for 45 minutes. The solution was cooled down to room temperature and concentrated. The solid residue was directly purified by silica gel chromatography (n-hexanes/ethyl acetate=5:1 to 1:1) providing the desired pyrazole.

Step 5

In an appropriate sized vial, the azido-PEG carboxylic acid (1 equiv.) was stirred with thionyl chloride (39 equiv.) at room temp for 3 h. On completion, (LCMS shows the methyl ester in indicating reaction completion) the excess thionyl chloride was evaporated to yield the crude acid chloride. A solution of product from step 4 (1 equiv.) was added in anh. THF was added to the acid chloride and TEA (5 equiv.) and the reaction mixture was stirred at 60° C. for 3 h. On completion the mixture was filtered through a cotton plug and purified by prep HPLC (50×30, C18, 50 mL/min, Rt. 3.3-3.6 min) which was taken up for the coupling step without further purification (assuming quantitative yield).

Step 6

In an appropriate sized vial, product from step 5 (1 equiv.), CuSO₄ (5 equiv.), sodium ascorbate (5 equiv.), propargyl-CRBN (1 equiv.) in THF:H₂O (1:1) was stirred at room temp overnight. On completion, the reaction mixture was diluted with ACN (1 mL) and purified by prep HPLC. Synthetic Method I (PROTAC)

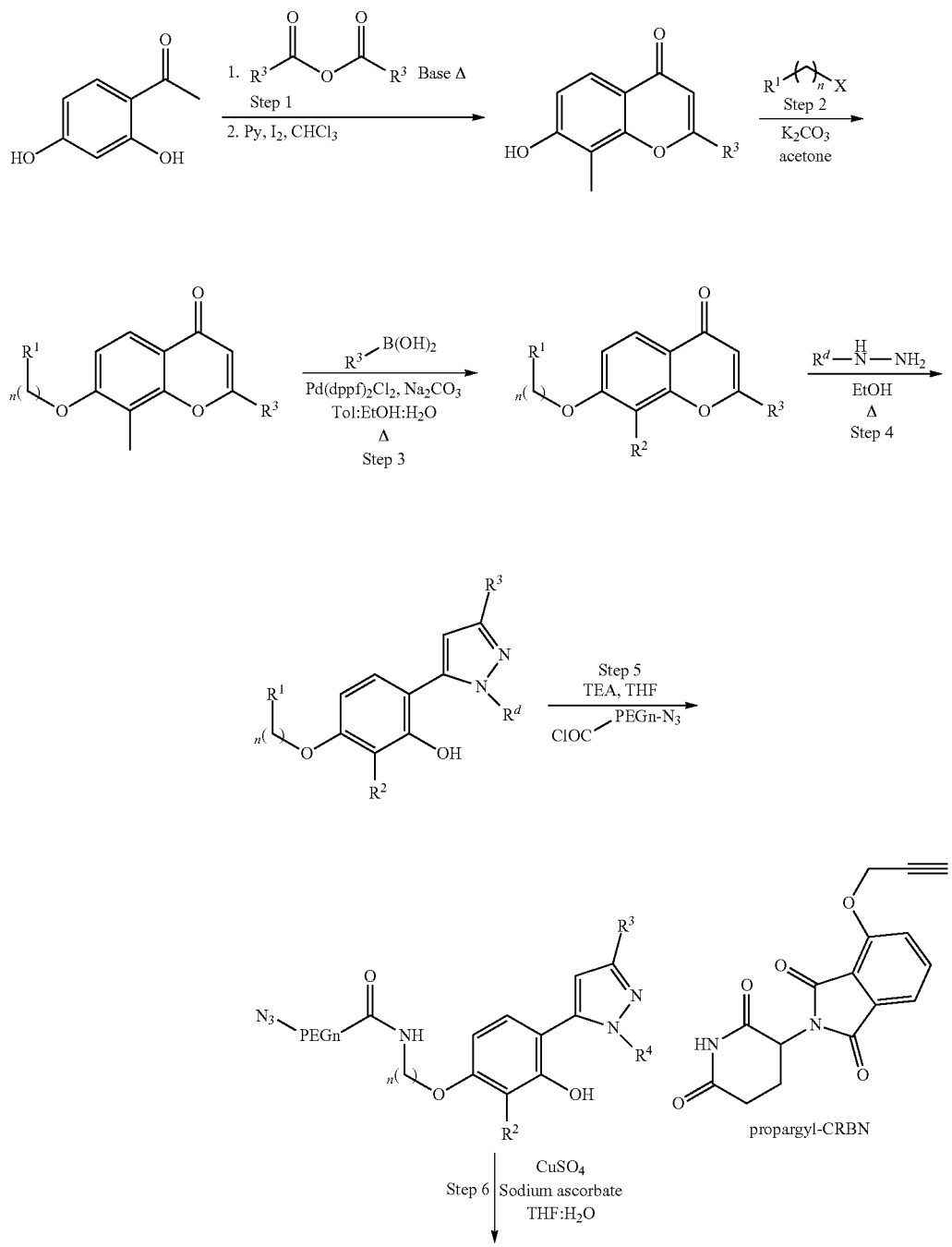

-continued
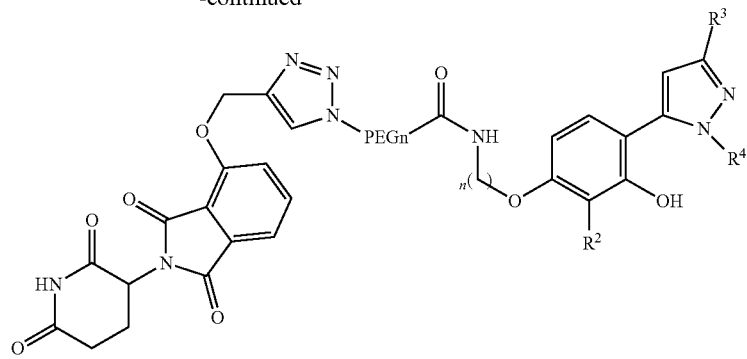
The following molecules were synthesized utilizing Synthetic method I (PROTAC).
NUCC-201202
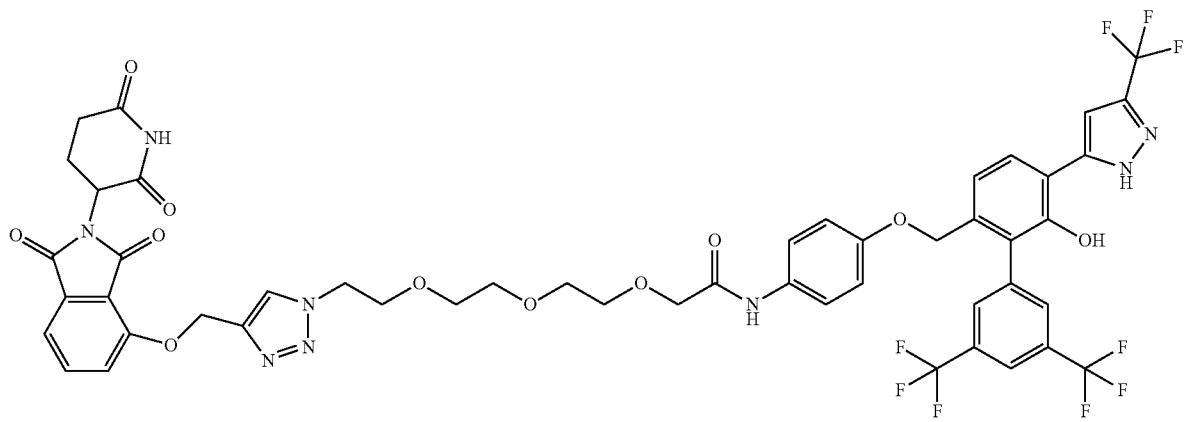
NUCC-201202
NUCC-0201202: Prep HPLC (45-95% 50×30, C18, 50 mL/min, Rt=3.2-3.7 min). UVmax=222 nm. $^1$H NMR (500 MHz, CDCl$_3$) δ 8.80 (s, 1H), 8.26 (s, 1H), 7.90 (s, 2H), 7.79 (s, 1H), 7.71 (s, 1H), 7.65-7.43 (m, 5H), 7.37 (t, J=7.9 Hz, 2H), 7.13 (d, J=8.1 Hz, 2H), 6.86 (s, 1H), 6.68 (d, J=8.7 Hz, 1H), 5.26 (s, 2H), 5.04-4.79 (m, 3H), 4.32 (s, 2H), 4.08 (s, 2H), 3.84-3.45 (m, 13H), 3.04-2.51 (m, 5H), 2.23-1.95 (m, 4H), 1.57 (s, 4H) ppm.
NUCC-201203
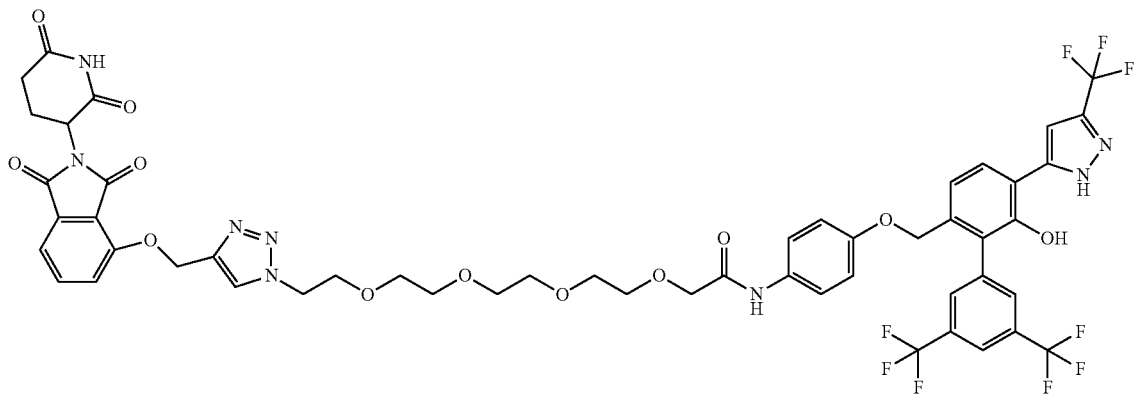
NUCC-201203

NUCC-0201203: Prep HPLC (45-95% 50×30, C18, 50 mL/min, Rt=3.25-4 min). UVmax=222 nm. $^1$H NMR (500 MHz, CDCl$_3$) δ 8.80 (s, 1H), 8.29 (s, 1H), 7.91 (s, 3H), 7.78 (d, J=11.5 Hz, 3H), 7.61 (t, J=7.9 Hz, 2H), 7.52 (d, J=8.3 Hz, 4H), 7.42 (dd, J=14.9, 7.9 Hz, 3H), 7.14 (d, J=8.1 Hz, 2H), 6.87 (s, 1H), 6.68 (d, J=8.7 Hz, 1H), 5.31 (s, 2H), 5.07-4.79 (m, 4H), 4.37 (t, J=5.1 Hz, 2H), 4.07 (s, 3H), 3.85-3.32 (m, 20H), 3.01-2.53 (m, 5H), 2.26-1.93 (m, 4H), 1.58 (s, 4H) ppm.

NUCC-201660

NUCC-201660

NUCC-0201660: Prep HPLC (45-95% 50×30, C18, 50 mL/min, Rt=4.25 min). UVmax=222 nm.

NUCC-201702

NUCC-201702

NUCC-0201702: $^1$H NMR (500 MHz, CDCl$_3$) δ 8.35 (s, 1H), 7.86 (s, 1H), 7.75 (d, J=2.0 Hz, 1H), 7.67 (dd, J=8.5, 7.3 Hz, 1H), 7.61-7.37 (m, 4H), 7.17 (d, J=8.6 Hz, 1H), 6.96 (t, J=6.2 Hz, 1H), 6.64 (d, J=8.6 Hz, 1H), 6.53 (s, 1H), 5.39 (d, J=2.8 Hz, 3H), 4.89 (dd, J=12.3, 5.4 Hz, 1H), 4.60-4.40 (m, 2H), 4.08-3.90 (m, 3H), 3.81 (d, J=5.3 Hz, 4H), 3.69-3.48 (m, 7H), 3.27 (q, J=6.8 Hz, 2H), 2.26-2.03 (m, 4H), 1.85 (q, J=6.4 Hz, 2H), 1.23 (d, J=2.2 Hz, 3H) ppm.

NUCC-201703
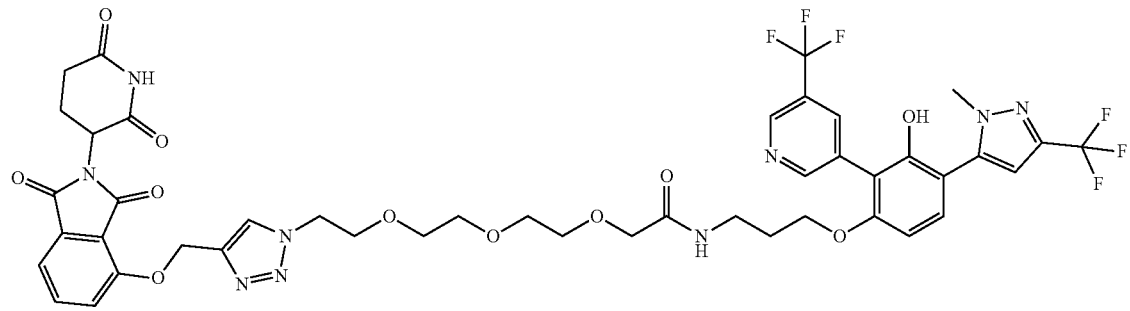
NUCC-201703
NUCC-0201703: Prep HPLC (20-80% 50×30, C18, 50 mL/min, Rt=4.15 min). Uvmax=222 nm.
NUCC-201704
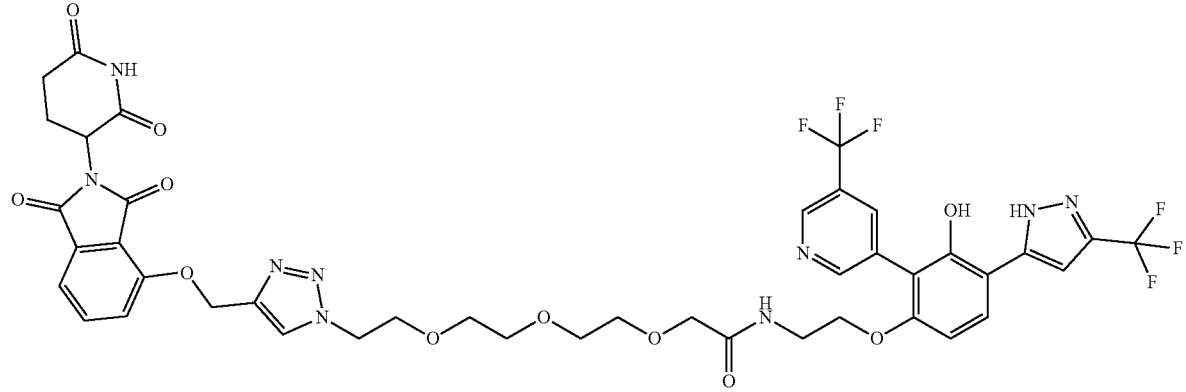
NUCC-201704
NUCC-0201704: Prep HPLC (20-80% 50×30, C18, 50 mL/min, Rt=4 min). Uvmax=222 nm. $^{1}$H NMR (500 MHz, CDCl$_3$) δ 8.82 (d, J=33.9 Hz, 2H), 8.07 (s, 1H), 7.97 (s, 1H), 7.77 (s, 1H), 7.63 (t, J=7.9 Hz, 1H), 7.53 (d, J=8.8 Hz, 1H), 7.48-7.37 (m, 1H), 7.02 (d, J=4.2 Hz, 1H), 6.88 (s, 1H), 6.61 (d, J=8.8 Hz, 1H), 5.28 (d, J=3.0 Hz, 1H), 4.92 (dd, J=11.9, 5.5 Hz, 1H), 4.40 (t, J=5.1 Hz, 1H), 4.07 (t, J=5.1 Hz, 1H), 3.94 (s, 1H), 3.75 (t, J=5.1 Hz, 1H), 3.68-3.41 (m, 4H), 3.02-2.64 (m, 2H), 2.15 (s, 1H), 1.24 (s, 2H), 0.84 (d, J=22.7 Hz, 1H) ppm.
Example 2—Synthesis of Core A6
Core A6 was synthesized using the following Synthetic Scheme.
Synthetic Scheme: Core A6
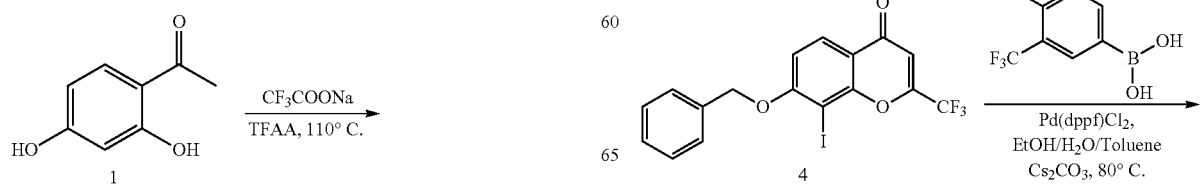
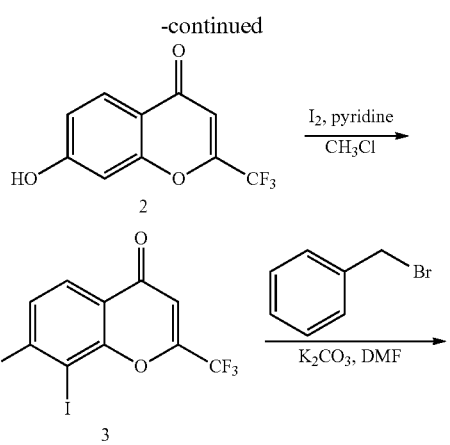

47

-continued

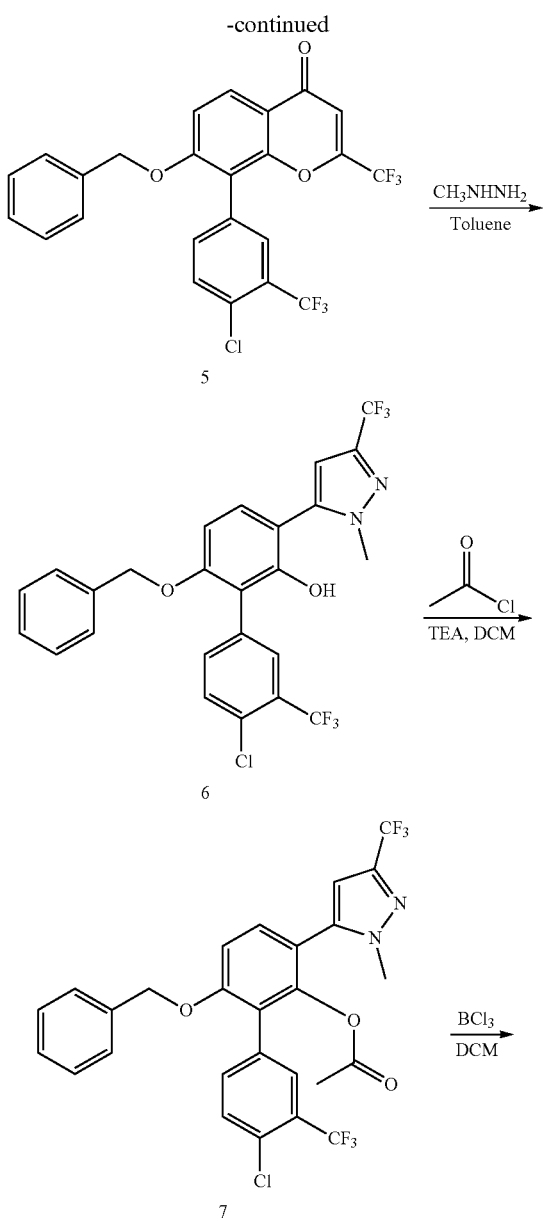

48

Experimental for Largest Scale Run:
General Procedure for Preparation of Compound 2

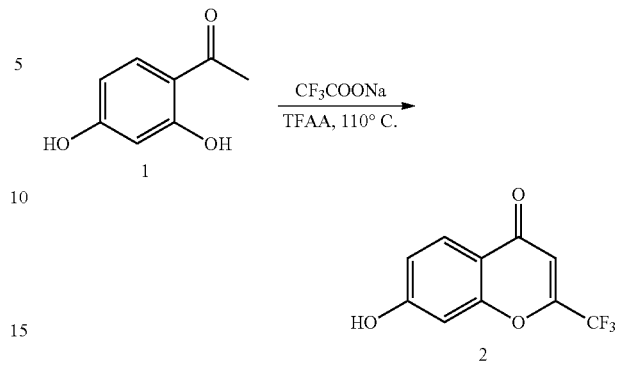

To a suspension of Compound 1 (10 g, 65.73 mmol, 8.47 mL, 1 eq) in TFAA (37 mL) was placed in a high pressure tube (100 mL). Sodium trifluoroacetate (19.67 g, 144.60 mmol, 2.2 eq) was added and the system was capped and stirred at 130° C. for 24 h. Totally 30 batches were set as parallel reaction. LCMS showed all starting materials consumed. The reaction was allowed to cool to 25° C. and combined and then was diluted with EtOAc (1 L). The mixture was neutralized by saturated aqueous $K_2CO_3$ solution until no more bubbling was observed. The organic layer was separated and the aqueous portion was extracted with EtOAc (3×500 mL). The organic layer was washed by brine, dried over anhydrous $Na_2SO_4$, concentrated to ⅓ volume of EtOAc and the flask was allowed to stand at 25° C. for 8 hrs. Compound 2 (180 g, 793.0 mmol, 40.0% yield) was collected as white solid.

Reaction LCMS:
LCMS Method:
LCMS (ESI+): m/z=231.1 (M+H)+, RT: 0.806 min.
5_95AB_2 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization. MS range was 100-1000.
$^1$H NMR (400 MHz, METHANOL-d$_4$) δ ppm 6.75 (s, 1H) 6.93 (d, J=2.20 Hz, 1H) 7.01 (dd, J=8.86, 2.26 Hz, 1H) 8.02 (d, J=8.80 Hz, 1H).

General Procedure for Preparation of Compound 3

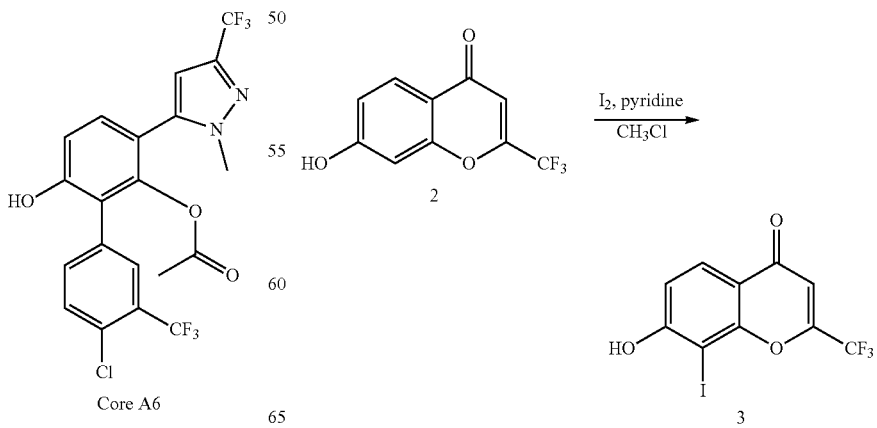

A solution of Compound 2 (180 g, 782.13 mmol, 1 eq), iodine (794.05 g, 3.13 mol, 630.20 mL, 4 eq), pyridine (247.47 g, 3.13 mol, 252.52 mL, 4 eq) in chloroform (1 L) was stirred at 25° C. for 8 h. LCMS showed the reaction completed. The mixture was poured into water (500 mL) and triturated with petroleum ether:ethyl acetate (10:1, 800 mL) to give Compound 3 (210 g, 589.83 mmol, 75.41% yield) as yellowish solid.

Reaction LCMS:

LCMS Method:

LCMS (ESI+): m/z=356.9 (M+H)+, RT: 0.890 min.

5_95AB_2 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5um particles). Detection methods are diode array (DAD) and evaporative light scattering (ELSD) detection as well as positive electrospray ionization. MS range was 100-1000.

$^1$H NMR (400 MHz, METHANOL-$d_4$) δ ppm 6.79 (s, 1H) 7.02 (d, J=8.82 Hz, 1H) 7.95-7.99 (m, 1H).

General Procedure for Preparation of Compound 4

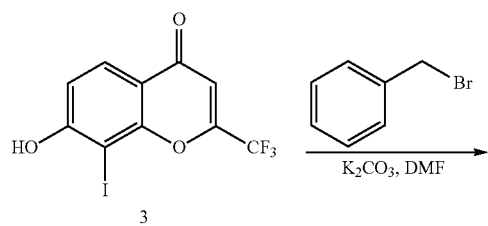

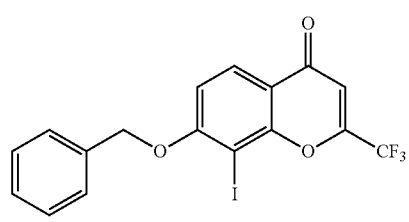

A solution of Cpd 3 (130 g, 365.13 mmol, 1 eq), bromomethylbenzene (74.94 g, 438.16 mmol, 52.04 mL, 1.2 eq), bromomethylbenzene (74.94 g, 438.16 mmol, 52.04 mL, 1.2 eq) in acetone (1 L) was added potassium carbonate (100.93 g, 730.26 mmol, 2 eq). The mixture was stirred at 80° C. for 8 h. TLC showed the reaction completed. The mixture was poured into water (500 mL) and extracted with ethyl acetate (3×500 mL). The organic layer was dried over Na$_2$SO$_4$ and concentrated to give crude product, which was purified by chromatography on silica, eluted with petroleum ether:ethyl acetate=10:1 to 5:1 to give desired product Cpd 4 (120 g, 268.96 mmol, 73.66% yield) as yellowish solid.

$^1$H NMR (400 MHz, CHLOROFORM-d) δ ppm 5.27 (s, 2H) 6.63 (s, 1H) 6.96 (d, J=8.93 Hz, 1H) 7.10-7.39 (m, 8H) 7.40-7.46 (m, 2H) 8.08 (d, J=8.93 Hz, 1H)

General Procedure for Preparation of Compound 5

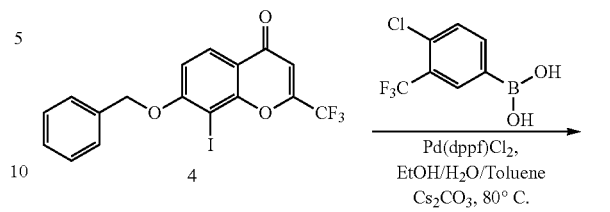

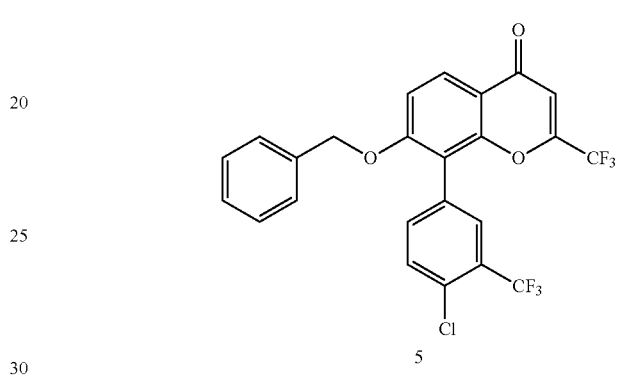

A solution of Cpd 4 (100 g, 22.41 mmol, 1 eq), [4-chloro-3-(trifluoromethyl)phenyl]boronic acid (5.03 g, 22.41 mmol, 1 eq), cesium carbonate (14.61 g, 44.83 mmol, 2 eq) in toluene (2 L) and ethanol (400 mL) and water (80 mL) was added Pd(dppf)Cl$_2$ (1.64 g, 2.24 mmol, 0.1 eq) under N$_2$ atmosphere. The mixture was stirred at 80° C. for 8 h. TLC showed the reaction completed. The mixture was poured into water (500 mL) and extracted with ethyl acetate (3×500 mL). The organic layer was dried over Na$_2$SO$_4$ and concentrated to give crude product which was triturated with ethyl acetate:petroleum ether (1:10, 500 mL) to give desired product Cpd 5 (93 g, 18.64 mmol, 83.18% yield) as yellowish solid.

$^1$H NMR (400 MHz, CHLOROFORM-d) δ ppm 5.26 (s, 2H) 6.71 (s, 1H) 7.27 (d, J=2.93 Hz, 2H) 7.34-7.41 (m, 3H) 7.55-7.66 (m, 2H) 7.85 (s, 1H) 8.26 (d, J=8.93 Hz, 1H).

General Procedure for Preparation of Compound 6

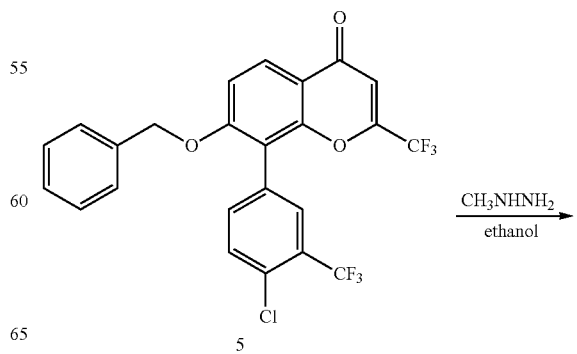

-continued

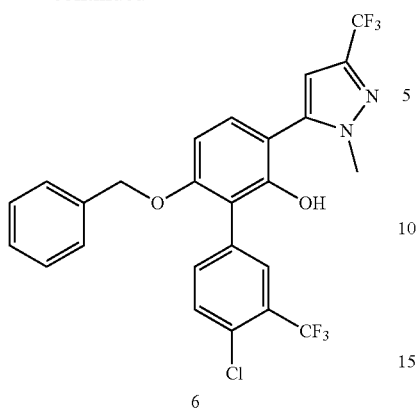

6

A suspension of Cpd 5 (100 g, 200.48 mmol, 1 eq), methylhydrazine (27.71 g, 601.44 mmol, 31.67 mL, 3 eq) in ethanol (500 mL) was bubbled with $N_2$ gas for 10 minutes. The vial was then heated at 80° C. for 16 h. LCMS showed all starting materials consumed. The resulting mixture was concentrated to give crude residue which was triturated by toluene to obtain Cpd 6 (75 g, 142.35 mmol, 71.01% yield) as brown solid.

LCMS (ESI+): m/z=527.2 (M+H)+, RT: 1.203 min.

5_95AB_2 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (Sum particles). Detection methods are diode array (DAD) and evaporative light scattering (ELSD) detection as well as positive electrospray ionization. MS range was 100-1000.

General Procedure for Preparation of Compound 7

-continued

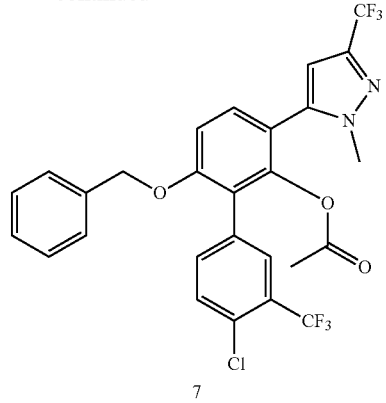

7

A solution of Cpd 6 (42 g, 79.72 mmol, 1 eq) in DCM (500 mL) was added acetyl chloride (7.51 g, 95.66 mmol, 6.83 mL, 1.2 eq) and TEA (9.68 g, 95.66 mmol, 13.31 mL, 1.2 eq). The mixture was stirred at 25° C. for 8 hrs. TLC showed all starting materials consumed. Once completion, the mixture was poured into water and extracted with DCM (2×100 mL). The organic layer was dried over $Na_2SO_4$, concentrated to give Cpd 7 (45 g, 79.10 mmol, 99.23% yield) as white solid which was used directly in next step.

$^1$H NMR (400 MHz, CHLOROFORM-d) δ 1.72-1.81 (m, 3H), 3.75-3.84 (m, 3H), 5.10-5.16 (m, 2H), 6.45-6.52 (m, 1H), 7.07 (d, J=8.60 Hz, 1H), 7.21-7.27 (m, 3H), 7.38 (s, 2H), 7.44-7.49 (m, 1H), 7.51-7.57 (m, 1H), 7.72-7.76 (m, 1H).

General Procedure for Preparation of Compound Core A6

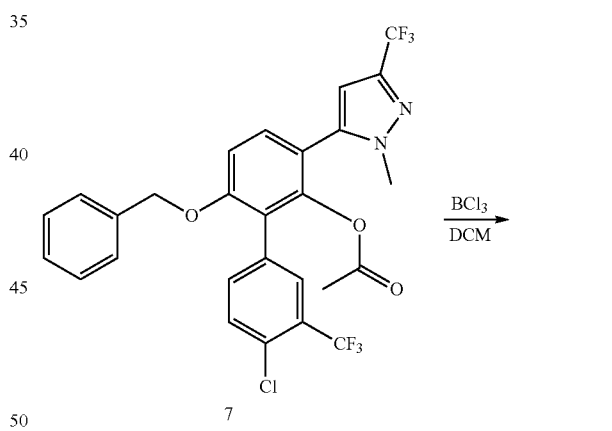

7

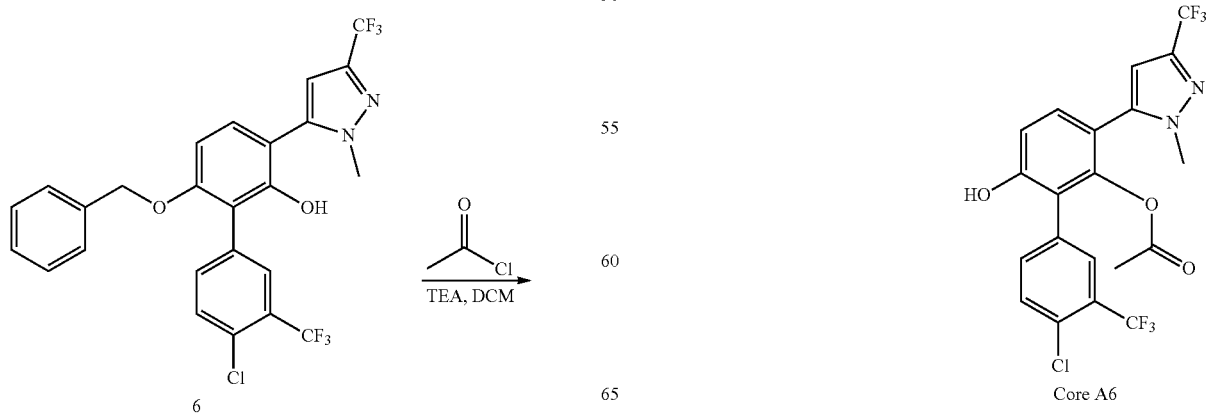

6    Core A6

A solution of Cpd 7 (50 g, 87.89 mmol, 1 eq) in DCM (200 mL) was cooled to 0° C. BCl₃ (1 M, 175.78 mL, 2 eq) was added to the mixture dropwise and maintain the temperature below 0° C. The mixture was stirred at 0° C. for 4 hs. TLC showed all starting materials consumed.

On completion, the mixture was added ice (100 mL) and separate the organic layer. The aqueous was extracted with EtOAc (3×100 mL). The organic layer was dried over Mg₂SO₄ and concentrated to give product which was purified by chromatography on silica, eluted with PE:EA=10:1 to 1:1 give Cpd A6 (25 g, 52.22 mmol, 59.41% yield) as white solid.

¹H NMR (400 MHz, CHLOROFORM-d) δ 1.78 (s, 3H), 3.76-3.84 (m, 3H), 5.95 (s, 1H), 6.48-6.53 (m, 1H), 6.96-7.02 (m, 1H), 7.23-7.28 (m, 1H), 7.48-7.53 (m, 1H), 7.62 (d, J=8.16 Hz, 1H), 7.70-7.74 (m, 1H).

Example 3—Synthesis of NUCC-0226202 (A5BC2R3)

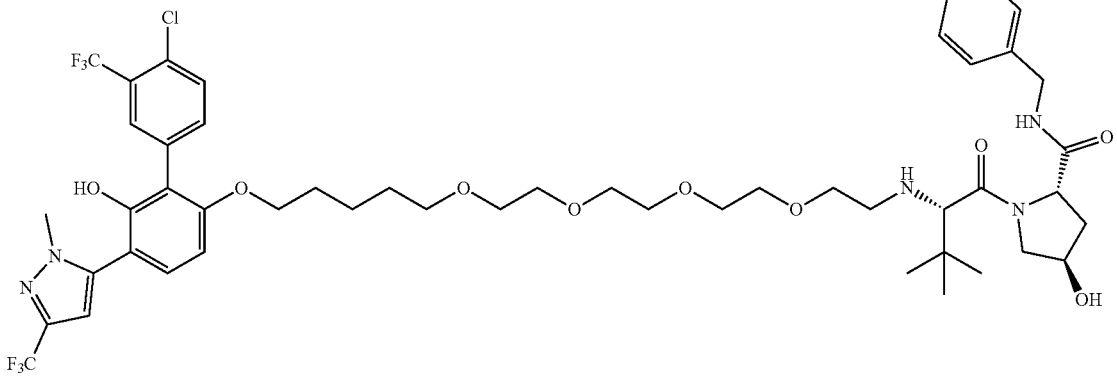

A5BC3R3

Synthetic Scheme: NUCC-0226202 (A5BC3R3)

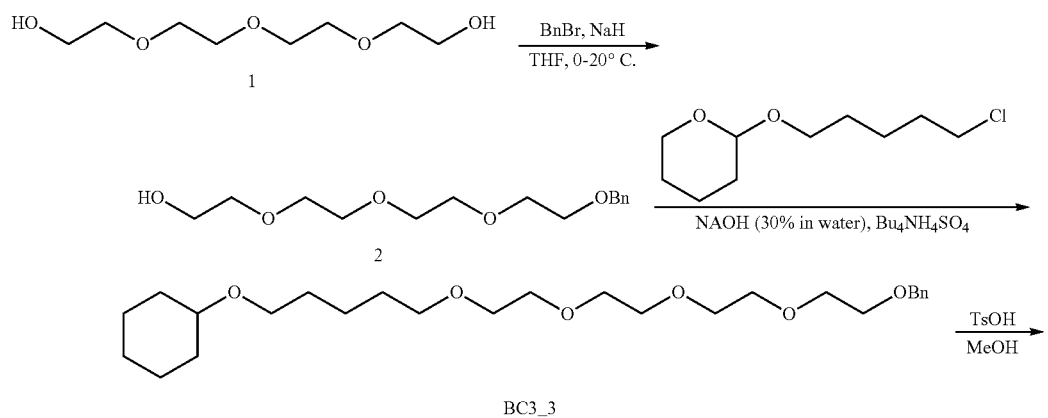

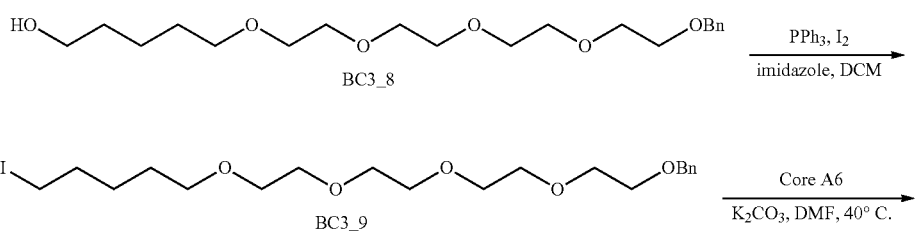

-continued
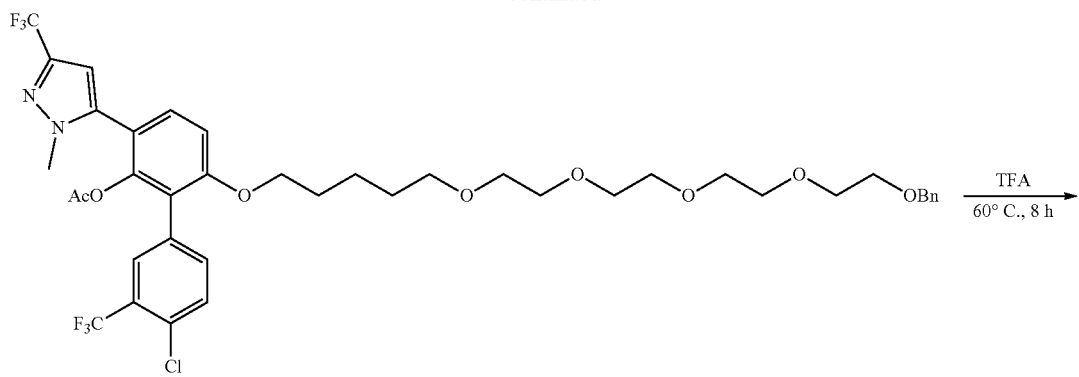
A5BC3_3
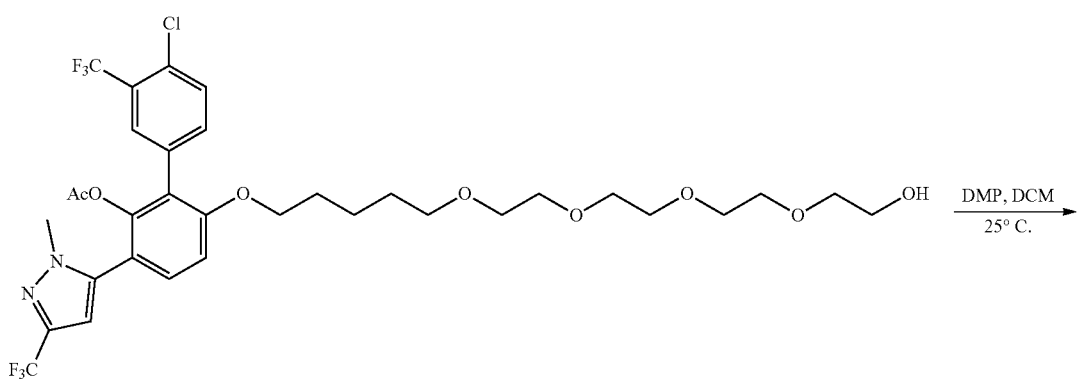
A5BC3_4
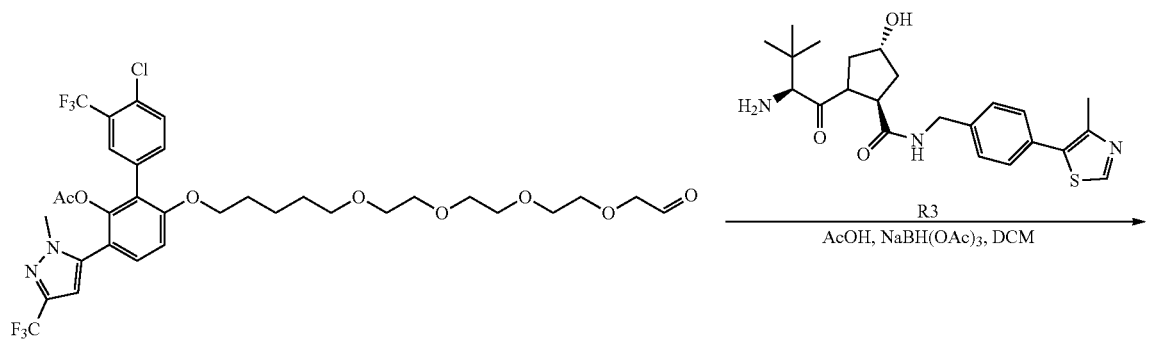
A5BC3_CHO
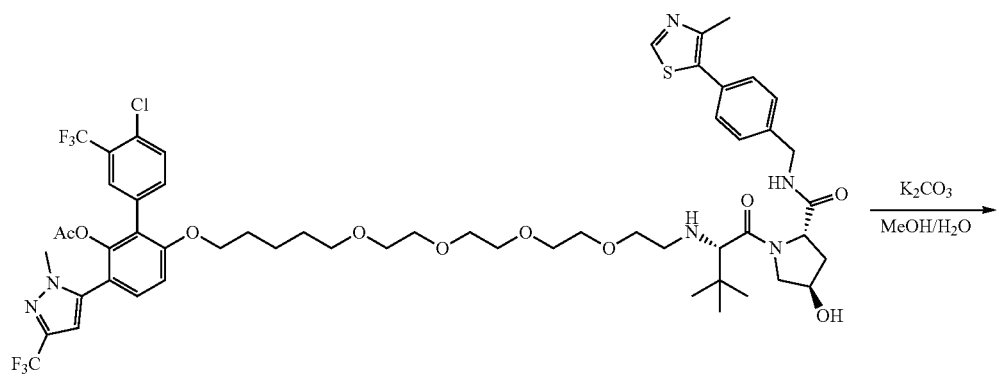
A5BC3R3_1

57 -continued

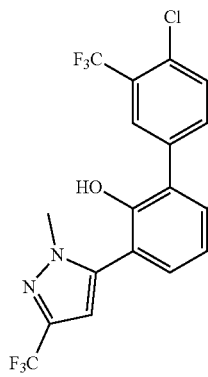 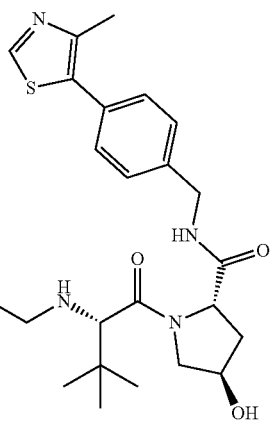

A5BC3R3

Experimental for Largest Scale Run:
General Procedure for Preparation of Compound 2.

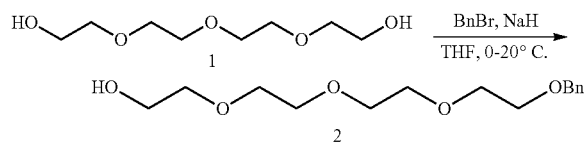

To a solution of Compound 1 (9 g, 46.34 mmol) in tetrahydrofuran (400 mL) was added NaH (926.76 mg, 23.17 mmol, 60% purity) at 0° C. Then the reaction was stirred at 0° C. for 30 min. Then bromomethylbenzene (3.96 g, 23.17 mmol) was added to the reaction at 0° C. and the reaction was stirred at 20° C. for 12 h. After the reaction was completed, the reaction was diluted with water (500 mL) and extracted with ethyl acetate (5×400 mL). The combined organic layer was dried over $Na_2SO_4$ and filtered, the filtrate was concentrated to give a residue which was purified by column chromatography on silica gel (eluted with PE:EA=20:1 to 1:100) to give Compound 2 (5 g, yield 38%) as light yellow oil.

$^1$H NMR: ET32240-1072-P1A (400 MHz, $CDCl_3$-d)
δ 3.61-3.75 (m, 17H), 4.59 (s, 2H), 7.27-7.38 (m, 5H)

General Procedure for Preparation of Compound BC3_3

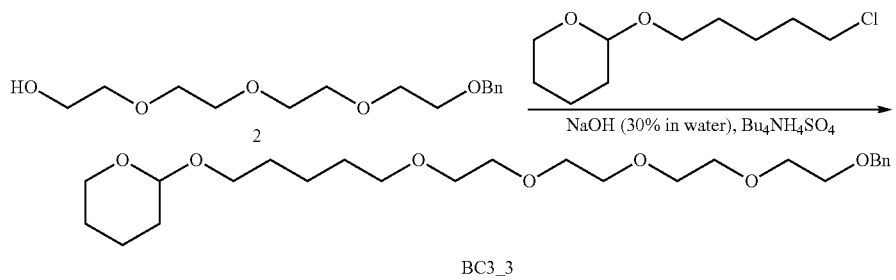

BC3_3

A solution of NaOH (38.7 g, 290.26 mmol, 30% purity) in water (100 mL) was added to a mixture of Compound 2 (4.13 g, 14.5 mmol), 2-(5-chloropentoxy)tetrahydropyran (3 g, 14.51 mmol) and tetrabutylammonium; sulfate (843.20 mg, 1.45 mmol) at 20° C. The mixture was stirred at 85° C. for 12 h. After the reaction was completed, the reaction was diluted with water (100 mL) and extracted with ethyl acetate (5×300 mL). The combined organic layer was dried over $Na_2SO_4$ and filtered, the filtrate was concentrated to give a residue which was purified by column chromatography on silica gel (eluted with PE:EA=20:1 to 1:100) to give BC3_3 (3.7 g, yield 56%) as light yellow oil.

$^1$H NMR: ET32240-1080-P1A (400 MHz, $CDCl_3$-d)
δ 1.38-1.45 (m, 2H), 1.52-1.65 (m, 10H), 1.66-1.89 (m, 3H), 3.38-3.49 (m, 4H), 3.55-3.58 (m, 2H), 3.64-3.66 (m, 11H), 3.71-3.76 (m, 1H), 3.86 (ddd, J=11.08, 7.55, 3.64 Hz, 1H), 4.57 (s, 3H), 7.34 (d, J=4.63 Hz, 5H)

General Procedure for Preparation of Compound BC3_8

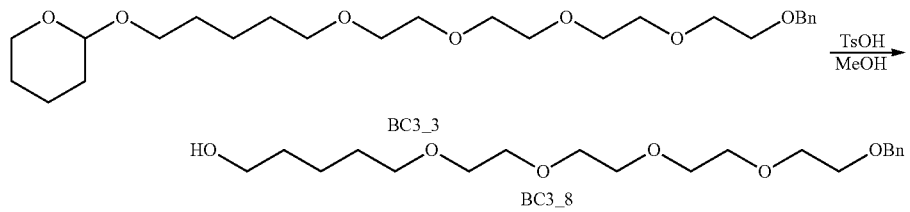

To a solution of BC3_3 (3.7 g, 8.14 mmol) in methanol (60 mL) was added TsOH·H₂O (1.55 g, 8.14 mmol) at 20° C. The reaction was stirred at 25° C. for 2 h. TLC showed all starting material consumed and desired product was detected. The reaction was quenched with K₂CO₃ solution (100 mL) and extracted with ethyl acetate (3×100 mL). The organic layer was concentrated to give crude product which was purified by chromatography on silica gel (eluted with PE:EA=100:1 to 1:100) to give BC3_8 (2 g, yield 66%) as colorless oil.

General Procedure for Preparation of Compound BC3_9

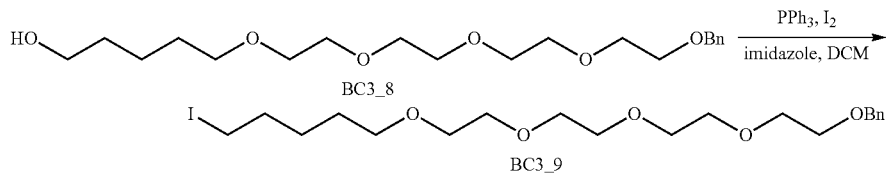

A solution of imidazole (1.10 g, 16.20 mmol) and PPh₃ (1.70 g, 6.48 mmol) in dichloromethane (50 mL) was added 2 (1.64 g, 6.48 mmol, 1.30 mL). The mixture was stirred for 10 min at 25° C. then solution of BC3_8 (2 g, 5.40 mmol) in dichloromethane (50 mL) was added dropwise. The mixture was stirred at 25° C. for 8 h. TLC showed all starting material consumed and desired product. The reaction was quenched with water (100 mL) and extracted with ethyl acetate (3×100 mL). The organic layer was concentrated to give crude product which was purified by chromatography on silica gel (eluted with PE:EA=50:1 to 10:1) to give BC3_9 (1.5 g, yield 53%) as colorless oil.

¹H NMR: ET32240-1098-P1A (400 MHz, CDCl₃-d)
δ 1.41-1.49 (m, 2H), 1.55-1.65 (m, 2H), 1.84 (quin, J=7.28 Hz, 2H), 3.18 (t, J=6.95 Hz, 2H), 3.45 (t, J=6.50 Hz, 2H), 3.55-3.69 (m, 16H), 4.57 (s, 2H), 7.25-7.37 (m, 5H)

General Procedure for Preparation of Compound A5BC3_3

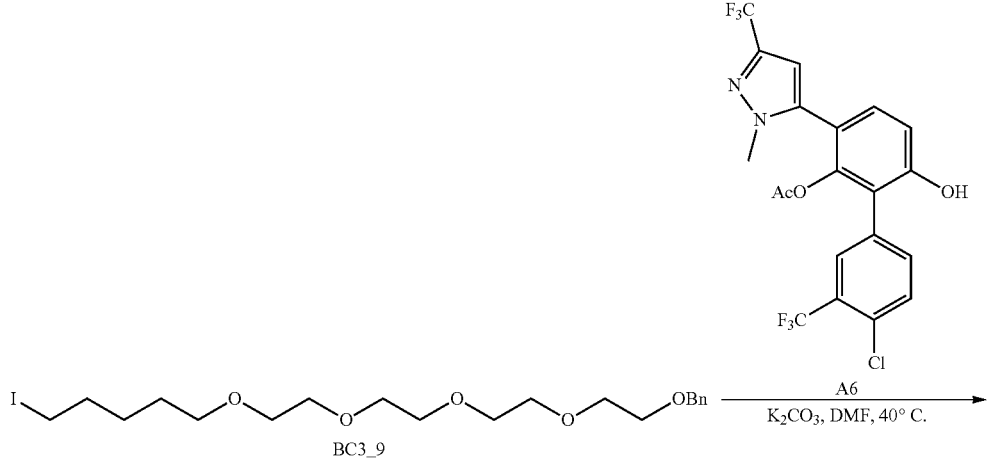

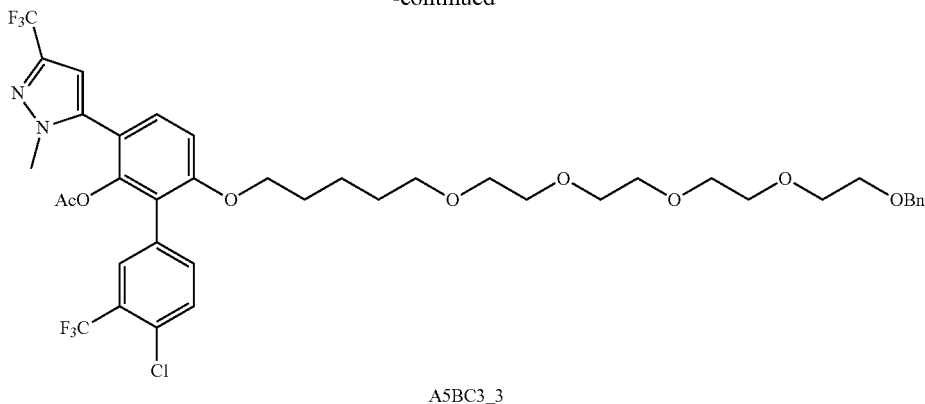

A5BC3_3

To a solution of Core A6 (1 g, 2.03 mmol, 1 eq) in N,N-dimethylethanamine (10 mL) was added Cpd BC3_9 (1.17 g, 2.44 mmol, 1.2 eq) and potassium carbonate (336.55 mg, 2.44 mmol, 1.2 eq). The reaction was stirred at 40° C. for 8 hr. The reaction was quenched with water (10 mL) and extracted with ethyl acetate (3×20 mL). The organic layer was concentrated to give crude product which was purified by column chromatography on silica (SiO2, petroleum ether/ethyl acetate=100/1 to 10/1) to give Cpd A5BC3_3 (0.5 g, 35% yield) as colorless oil.

General Procedure for Preparation of Compound A5BC3_4

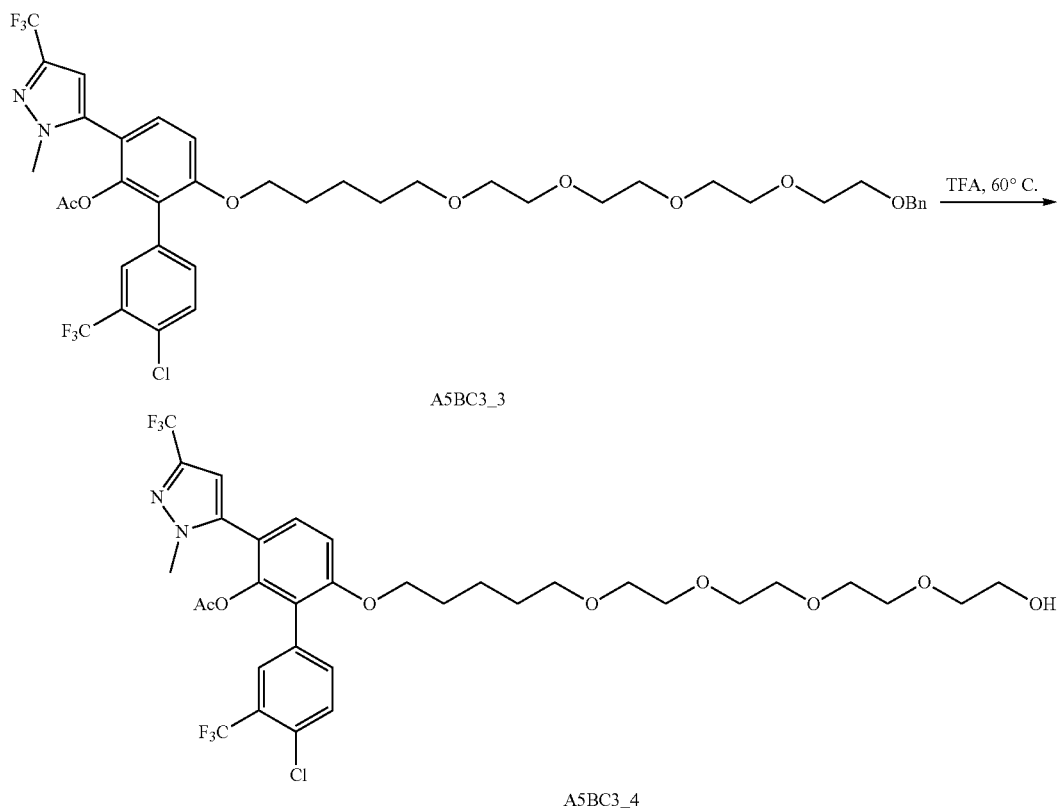

To a solution of Cpd A5BC3_3 (0.5 g, 601.51 umol, 1 eq) in trifluoroacetic acid (3 mL) was stirred at 60° C. for 8 hr. The reaction was added water (10 mL) and basified to pH=7 with NaHCO₃ and then extracted with ethyl acetate (10 mL). The organic layer was dried over Na₂SO₄ and concentrated to give Cpd A5BC3_4 (300 mg, 67% yield) as yellow oil which was used directly without further purification.

General Procedure for Preparation of Compound A5BC3_CHO

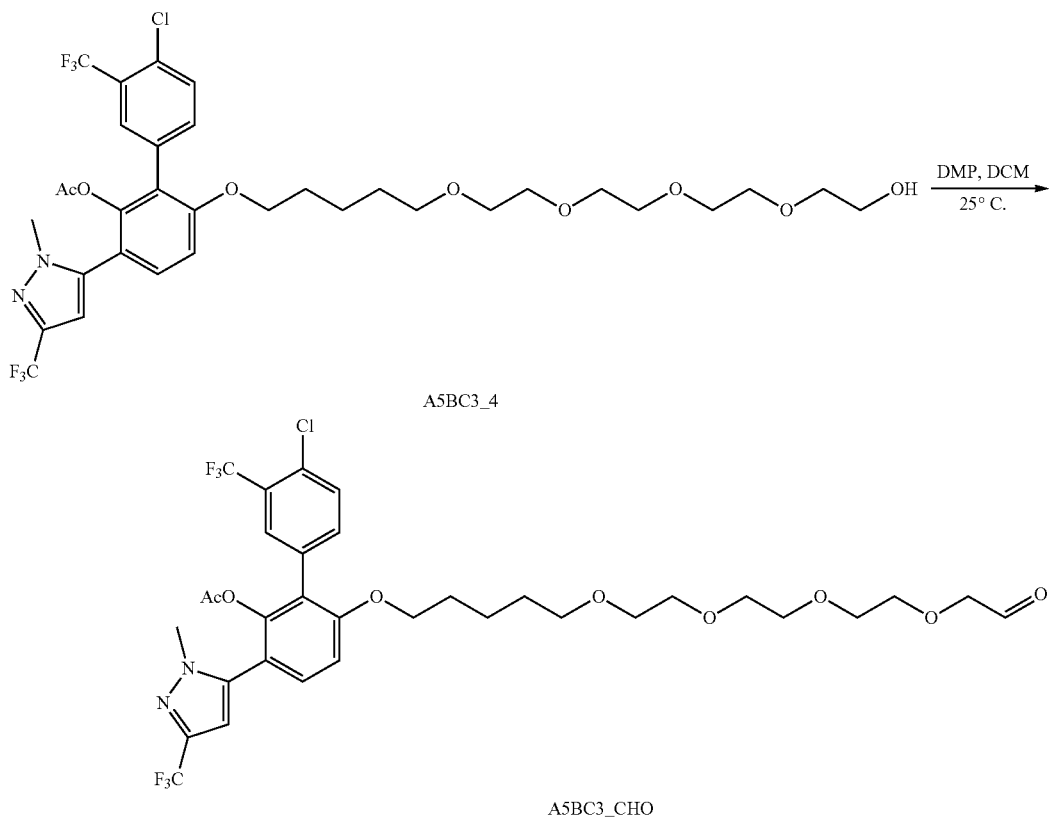

To a solution of A5BC3_4 (50 mg, 71.73 umol, 1 eq) in DCM (1 mL) was added DMP (45.64 mg, 107.59 umol, 33.31 uL, 1.5 eq). The mixture was stirred at 20° C. for 12 h. LCMS showed all starting materials remained and desired product. The reaction was quenched with water (5 mL) and extracted with ethyl acetate (3×5 mL). The organic layer was concentrated to give crude product. The crude product was purified by Prep-TLC to give A5BC3_CHO (40 mg, 54.20 umol) as colorless oil.

LCMS Method:
LCMS (ESI+): m/z=739.3 (+H)+, RT: 0.887 min.
5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (Sum particles). Detection methods are diode array (DAD) and evaporative light scattering (ELSD) detection as well as positive electrospray ionization. MS range was 100-1000.

General Procedure for Preparation of Compound A5BC3R3_1

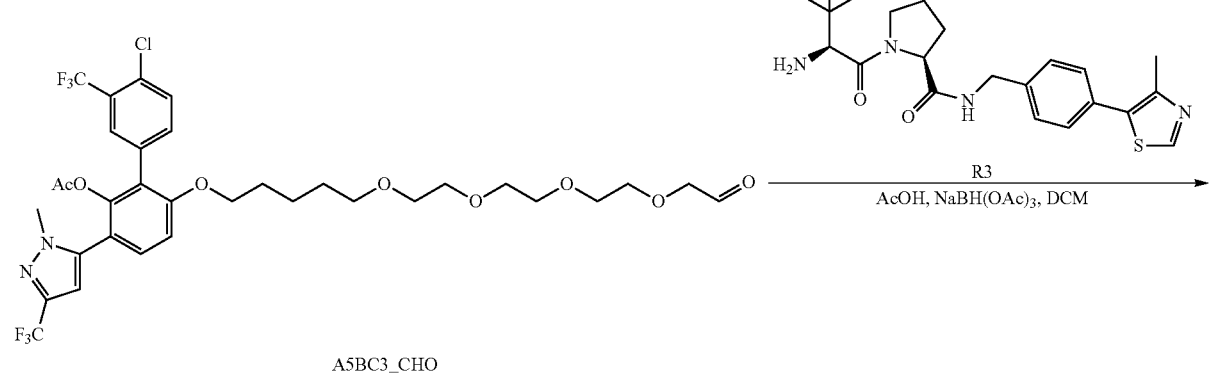

-continued

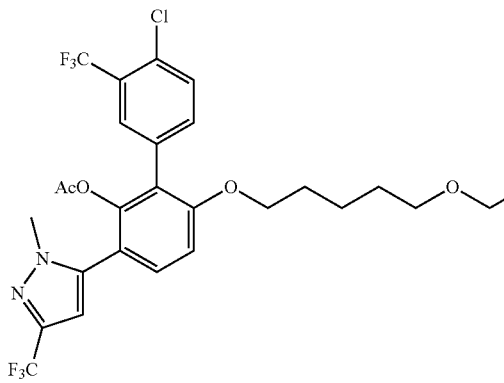
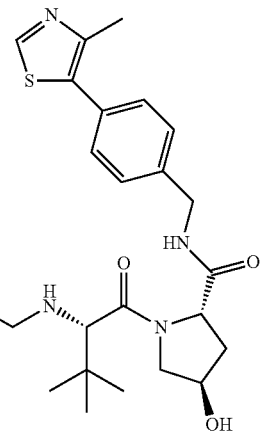

A5BC3R3_1

To a solution of A5BC3_CHO (40 mg, 54.12 umol) in dichloromethane (2 mL) was added R3 (46.60 mg, 108.24 umol), sodium triacetoxyborohydride (34.41 mg, 162.36 umol), and acetic acid (14.62 mg, 243.54 umol) at 0° C. The reaction was stirred at 20° C. for 0.5 h. Then the reaction mixture was treated with water (10 mL) and extracted with dichloromethane (3×10 mL). Then the organic phase was washed with brine (10 mL), dried over anhydrous sodium sulfate and filtered. The filtrate was concentrated under reduced pressure to give A5BC3R3_1 (40 mg, crude) as yellow solid. The product was used directly for the next step without further purification.

LCMS Method:
LCMS (ESI+): m/z=1153.7 (+H)+, RT: 1.188 min.
5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5um particles). Detection methods are diode array (DAD) and evaporative light scattering (ELSD) detection as well as positive electrospray ionization. MS range was 100-1000.

General Procedure for Preparation of Compound A5BC3R3

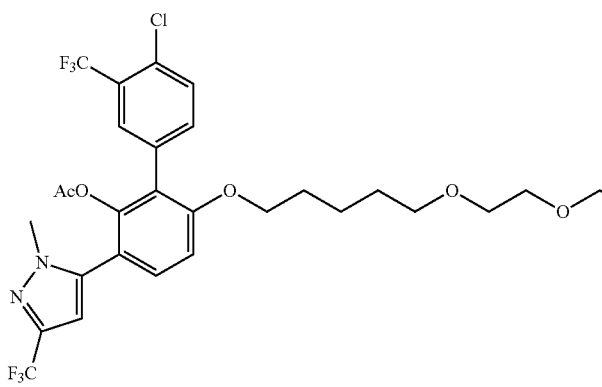
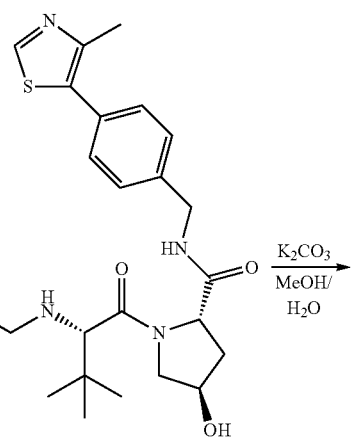

A5BC3R3_1

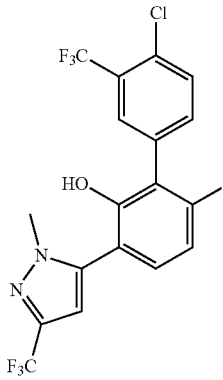

A5BC3R3

To a solution of A5BC3R3_1 (30 mg, 26.00 umol) in a mixture of methanol (1.5 mL) and water (1.5 mL) was added potassium carbonate (14.38 mg, 104.02 umol) at 20° C. The reaction was stirred at 20° C. for 1 h. Then the reaction mixture was treated with water (5 mL) and extracted with dichloromethane (3×5 mL). Then the organic phase was washed with brine (5 mL), dried over anhydrous sodium sulfate and filtered. The filtrate was concentrated under reduced pressure to give crude product. Then the crude product was purified by Prep-HPLC to give A5BC3R3 (20 mg, yield 68%) as white solid.

Method of Prep-HPLC:
Instrument: Shimadzu LC-8A preparative HPLC
Column: Nano-micro Kromasil C18 100*40 mm 10 um
Mobile phase: A for water (0.09% trifluoroacetic acid) and B for acetonitrile
Gradient: B from 35% to 75% in 20 min
Flow rate: 50 mL/min
Wavelength: 220&254 nm $^1$H NMR: ET32240-1217-P1Z (400 MHz, CDCl3-d)

δ 0.78-0.95 (m, 1H), 1.08 (s, 9H), 1.26 (s, 1H), 1.29-1.38 (m, 2H), 1.54 (quin, J=7.09 Hz, 2H), 1.62-1.72 (m, 2H), 2.52 (s, 5H), 3.11-3.21 (m, 1H), 3.30-3.37 (m, 1H), 3.41 (br t, J=6.60 Hz, 2H), 3.52 (br d, J=10.27 Hz, 1H), 3.55-3.59 (m, 2H), 3.60-3.70 (m, 10H), 3.70-3.75 (m, 1H), 3.84 (s, 3H), 3.87-3.93 (m, 1H), 3.94-4.02 (m, 3H), 4.32-4.42 (m, 2H), 4.49-4.59 (m, 2H), 4.81 (br t, J=8.31 Hz, 1H), 6.56 (s, 1H), 6.67 (d, J=8.80 Hz, 1H), 7.20 (d, J=8.31 Hz, 1H), 7.36 (s, 4H), 7.46-7.57 (m, 2H), 7.58-7.63 (m, 1H), 7.76 (d, J=1.47 Hz, 1H), 8.91 (s, 1H)

LCMS Method:
LCMS (ESI+): m/z=556.3 (M/2+H)+, RT: 3.582 min.
5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (Sum particles). Detection methods are diode array (DAD) and evaporative light scattering (ELSD) detection as well as positive electrospray ionization. MS range was 100-1000.

Example 4—Synthesis of NUCC-0226203 (A5BC2R4)

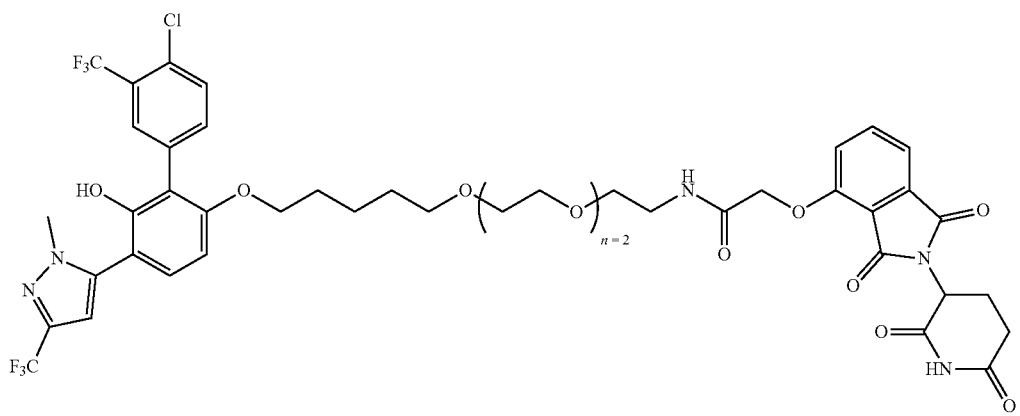

A5BC2R4

Synthetic Scheme: Synthesis of BC2_7_NPht
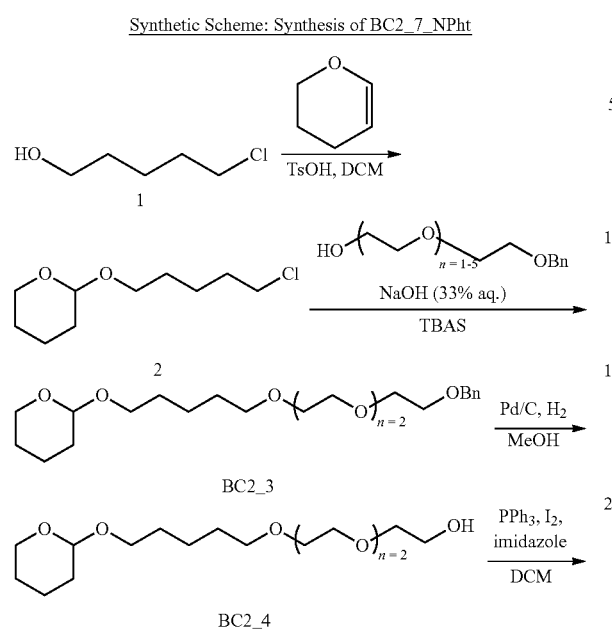
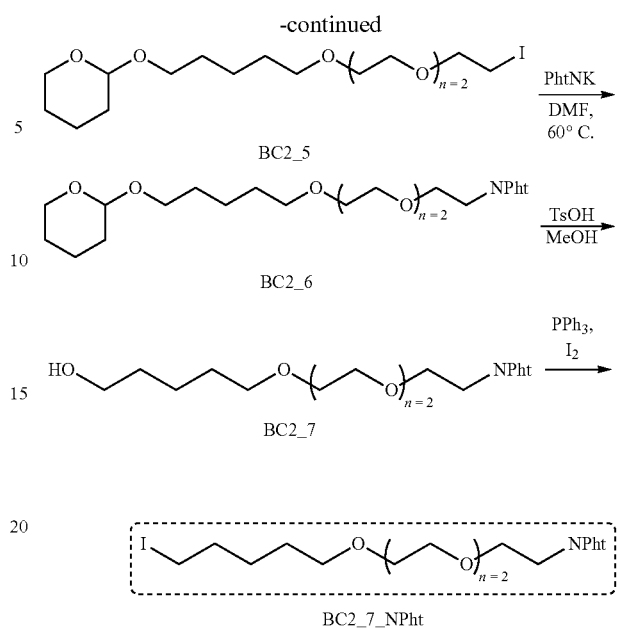
Scheme 2: Synthesis of A5BC2_NH2
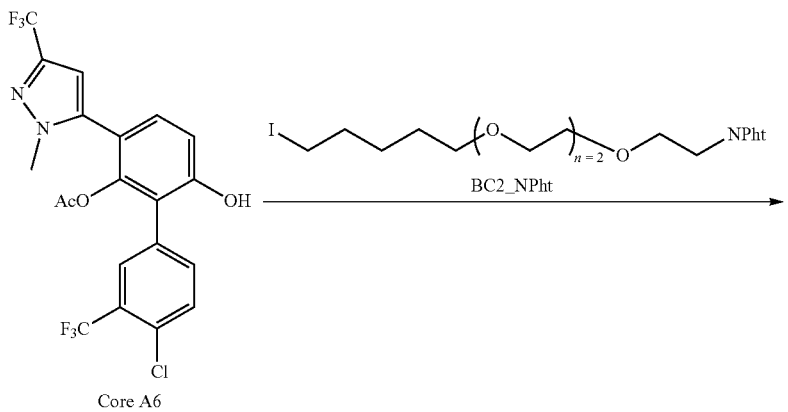
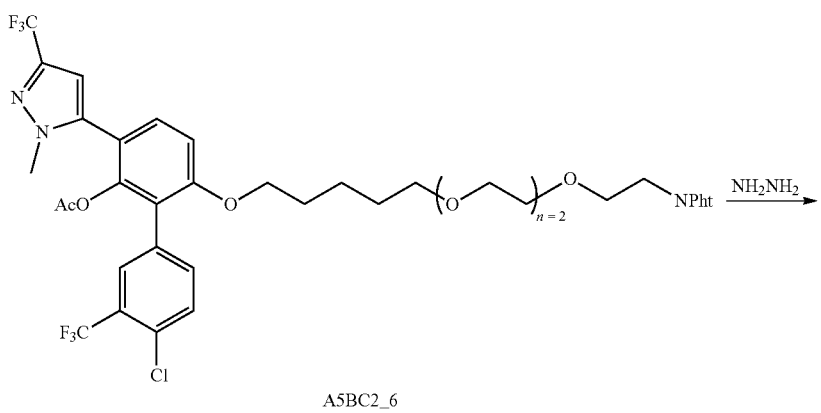

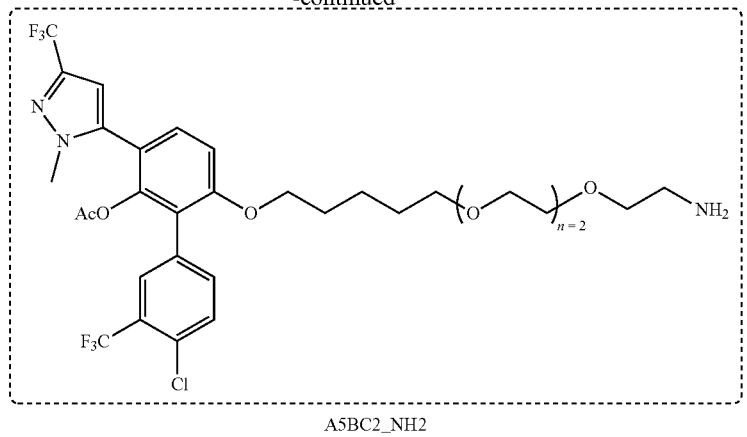
A5BC2_NH2
Scheme 3: Synthesis of A5BC2R4
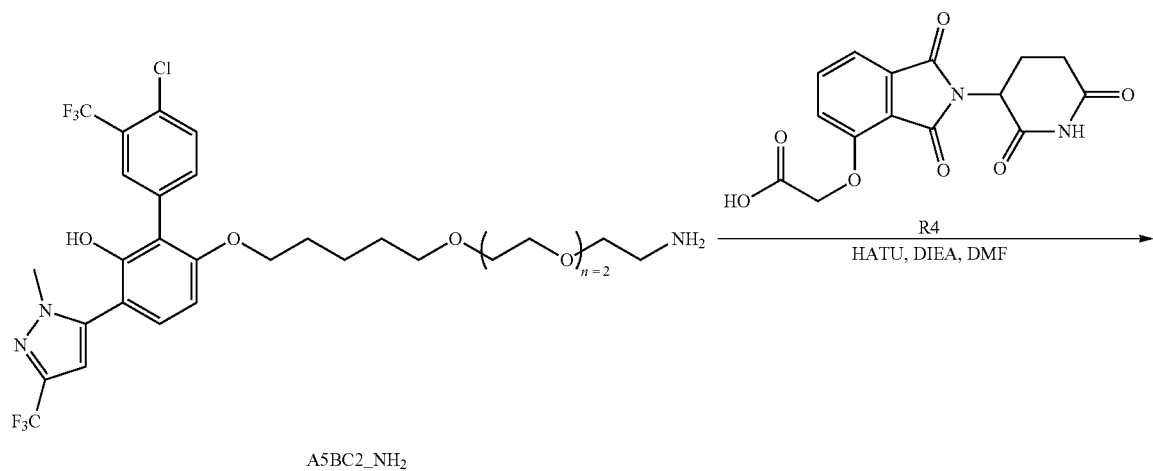
A5BC2_NH2
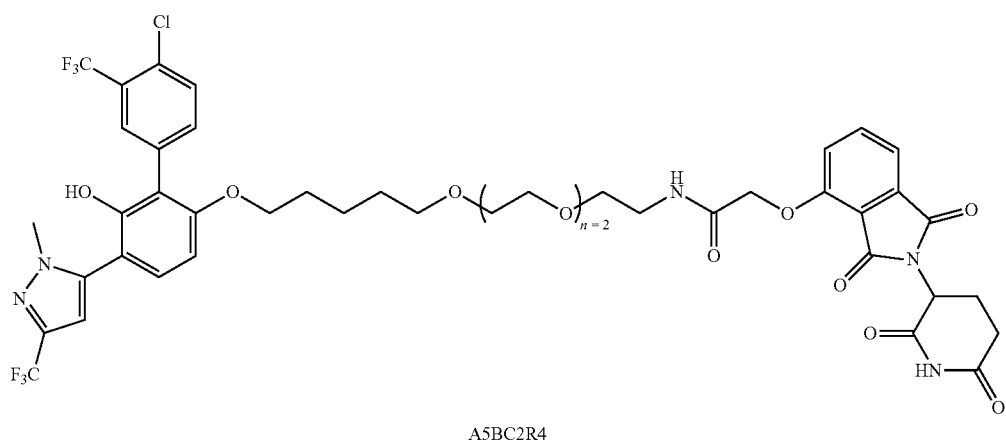
A5BC2R4

Experimental for Largest Scale Run:
General Procedure for Preparation of Compound 2

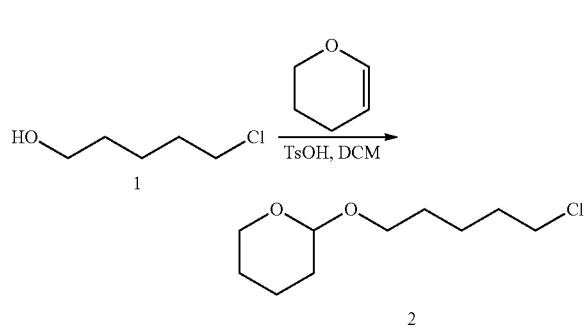

To a solution of Cpd 1 in DCM (500 mL) was added TsOH (7.02 g, 40.79 mmol, 0.1 eq) and then added 3,4-dihydro-2H-pyran (68.61 g, 815.71 mmol, 74.58 mL, 2 eq) dropwise. The mixture was stirred at 25° C. for 4 hrs. TLC showed all starting materials consumed and desired product. The reaction was quenched with $K_2CO_3$ (sat. 100 mL). The organic layer was concentrated to give crude product which was purified by chromatography on silica, eluted with PE:EA=10:1 to give Cpd 2 (60 g, 290.26 mmol, 71.17% yield) as colorless oil.

$^1$H NMR (400 MHz, CHLOROFORM-d) δ 1.47-1.90 (m, 13H), 3.32-3.46 (m, 1H), 3.47-3.61 (m, 3H), 3.71-3.81 (m, 1H), 3.87 (ddd, J=11.09, 7.45, 3.28 Hz, 1H), 4.49-4.65 (m, 1H).

General Procedure for Preparation of Compound BC2_3

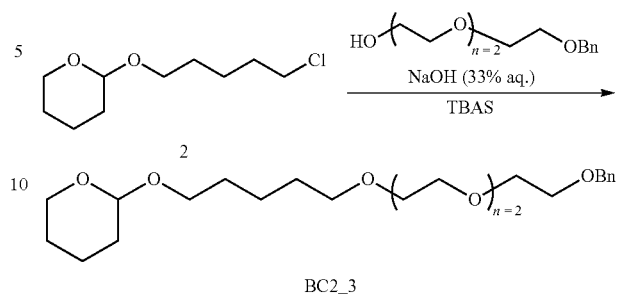

Tetrabutylammonium sulfate (2.81 g, 2.42 mmol, 2.78 mL, 50% purity, 0.1 eq) was added dropwise to a mixture of Cpd 2 (5 g, 24.19 mmol, 1 eq) and NaOH (58.63 g, 483.80 mmol, 33% purity, 20 eq) and 2-[2-(2-benzyloxyethoxy)ethoxy]ethanol (6.39 g, 26.61 mmol, 3.78 mL, 1.1 eq). The two-phase mixture was stirred vigorously and heated at 95° C. for 8 hrs. TLC showed all starting materials consumed and desired product. The reaction was quenched with water (100 mL) and then added ethyl acetate (300 mL). The organic layer was concentrated to give crude product which was purified by chromatography on silica, eluted with PE:EA=10:1 to give Cpd BC2_3 (5 g, 12.18 mmol, 50.35% yield) as colorless oil.

$^1$H NMR (400 MHz, CHLOROFORM-d) δ 1.27-1.82 (m, 14H), 3.24-3.70 (m, 18H), 3.74-3.85 (m, 1H), 4.44-4.53 (m, 3H), 7.15-7.30 (m, 5H).

General Procedure for Preparation of Compound BC2_4

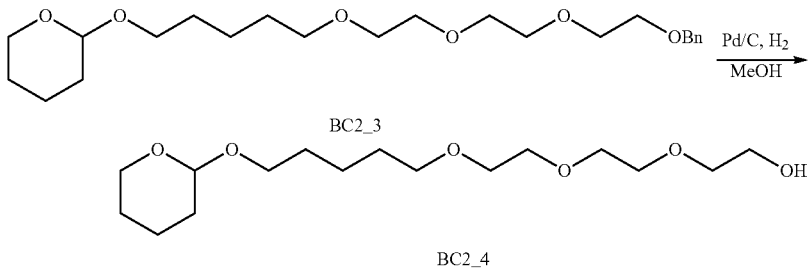

To a solution of Cpd BC2-3 (3 g, 7.31 mmol) in MeOH (50 mL) was added palladium hydroxide on carbon (2.23 g, 1.46 mmol, 10% w/w, 0.2 eq). The suspension was degassed under vacuum and purged with $H_2$ several times. The mixture was stirred under $H_2$ (15 psi) at 50° C. for 2 h. TLC showed the reaction was completed. The reaction mixture was filtered and the filtrate was concentrated to give Cpd BC2_4 (2 g, yield 85%) as colorless oil.

General Procedure for Preparation of Compound BC2_5

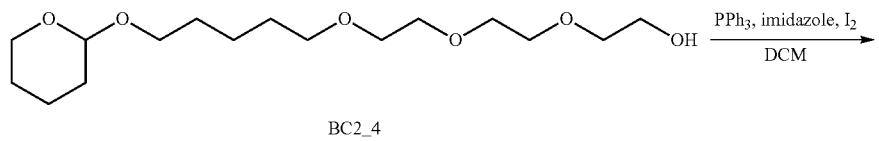

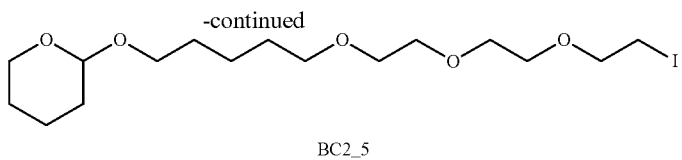

BC2_5

To a solution of imidazole (2 g, 18.73 mmol, 3 eq) and triphenylphosphine (1.96 g, 7.49 mmol, 1.2 eq) in dichloromethane (30 mL) was added iodine (1.90 g, 7.49 mmol, 1.2 eq) at 0° C. The reaction was stirred at 25° C. for 2 min. A solution of Cpd BC2_4 (2 g, 6.24 mmol, 1 eq) in dichloromethane (5 mL) was added to the mixture. The mixture was stirred at 25° C. for 8 hr. TLC showed the reaction was completed. The reaction was quenched with water (20 mL) and extracted with dichloromethane (3×20 mL). The organic layer was concentrated to give crude product. The crude product was purified by column chromatography on silica (SiO2, petroleum ether/ethyl acetate=100/1 to 10/1) to give Cpd BC2_5 (1.1 g, 41% yield) as colorless oil.

General Procedure for Preparation of Compound BC2_6.

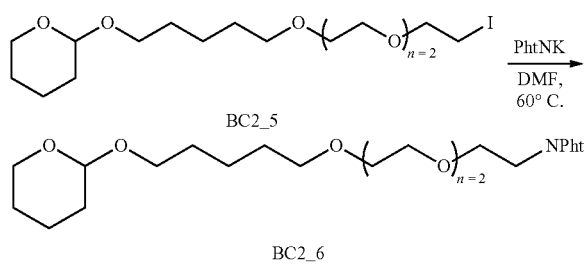

To a solution of Cpd BC2_5 (1.08 g, 2.51 mmol, 1 eq) in DMF (10 mL) was added (1,3-dioxoisoindolin-2-yl)potassium (557.89 mg, 3.01 mmol, 1.2 eq) and the mixture was stirred at 60° C. for 12 h. TLC showed the reaction was completed. The mixture was poured into water (50 mL) and EtOAc (20 mL). The two phases were separated and the aqueous phase was extracted with EtOAc (2×20 mL). The combined organic layers were dried over anhydrous Na2SO4, filtered and concentrated under reduced pressure to give a residue which was purified by column chromatography (SiO2, PE/EA=10/1 to 0/1) to give the product Cpd BC2_6 (0.95 g, 2.11 mmol, 84.19% yield) as colorless oil.

$^1$H NMR (400 MHz, CHLOROFORM-d)

δ 1.35-1.44 (m, 2H), 1.47-1.55 (m, 3H), 1.60 (br dd, J=6.68, 1.91 Hz, 3H), 1.69-1.72 (m, 1H), 1.82 (td, J=8.94, 5.96 Hz, 1H), 3.34-3.45 (m, 3H), 3.46-3.54 (m, 4H), 3.55-3.68 (m, 7H), 3.71-3.77 (m, 3H), 3.87-3.94 (m, 3H), 4.56 (br d, J=4.77 Hz, 1H), 7.69-7.75 (m, 2H), 7.81-7.87 (m, 2H)

General Procedure for Preparation of Compound BC2_7

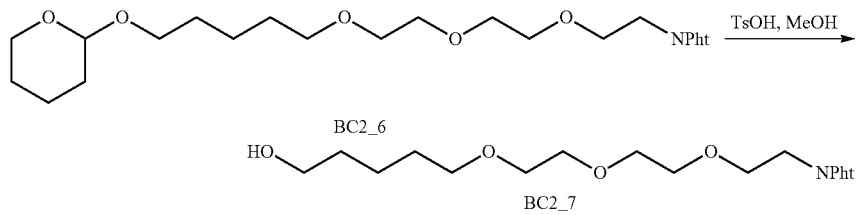

To a solution of BC2_6 (950 mg, 2.11 mmol) in methanol (20 mL) was added TsOH·H2O (401.98 mg, 2.11 mmol) at 20° C. The reaction was stirred at 20° C. for 2 h. Then the reaction mixture was quenched with potassium carbonate solution (30%, 100 mL) and extracted with ethyl acetate (3×100 mL). The organic phase was washed with brine (200 mL), dried over anhydrous sodium sulfate and filtered. The filtrate was concentrated under reduced pressure. Then the mixture was purified by flash column chromatography (eluting with petroleum ether:ethyl acetate=10:1 to 0:1) to give BC2_7 (360 mg, 46% yield) as a colorless oil.

$^1$H NMR: ET32240-1087-P1A (400 MHz, CDCl3-d)

δ 1.39-1.48 (m, 2H), 1.58-1.65 (m, 4H), 3.42-3.49 (m, 2H), 3.49-3.55 (m, 2H), 3.56-3.72 (m, 9H), 3.73-3.78 (m, 2H), 3.91 (br t, J=5.96 Hz, 2H), 7.69-7.79 (m, 2H), 7.82-7.91 (m, 2H)

General Procedure for Preparation of Compound BC2_NHPht

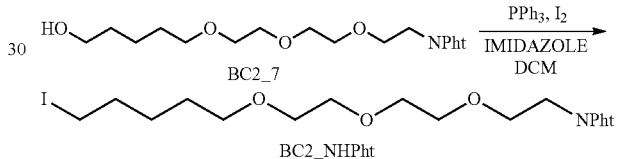

To a solution of triphenyl phosphate (310.08 mg, 1.18 mmol) and imidazole (201.20 mg, 2.96 mmol) in dichloromethane (10 mL) was added iodine (300.05 mg, 1.18 mmol) at 20° C. The mixture was stirred for 10 min at 25° C. Then a solution of BC2_7 (0.36 g, 985.17 umol) in dichloromethane (10 mL) was added. Then the mixture was stirred at 20° C. for 8 h. Then the reaction mixture was treated with water (20 mL) and extracted with dichloromethane (3×20 mL). Then the organic phase was washed with brine (20 mL), dried over anhydrous sodium sulfate and filtered. The filtrate was concentrated under reduced pressure. Then the mixture was purified by flash column chromatography (eluting with petroleum ether:ethyl acetate=10:1 to 0:1) to give BC2_NHPht (150 mg, 32% yield) as a colorless oil.

$^1$H NMR: ET32240-1102-P1A (400 MHz, CDCl3-d)

δ 1.40-1.50 (m, 2H), 1.57-1.63 (m, 2H), 1.84 (quin, J=7.28 Hz, 2H), 3.19 (t, J=7.06 Hz, 2H), 3.43 (t, J=6.50 Hz, 2H), 3.49-3.54 (m, 2H), 3.56-3.68 (m, 6H), 3.73-3.78 (m, 2H), 3.88-3.94 (m, 2H), 7.72 (dd, J=5.51, 3.09 Hz, 2H), 7.86 (dd, J=5.51, 3.09 Hz, 2H)

General Procedure for Preparation of Compound A5BC2_6

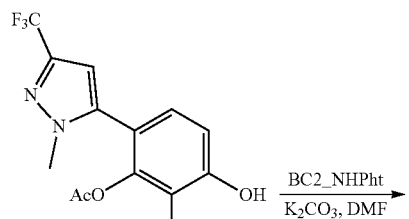

Core A6

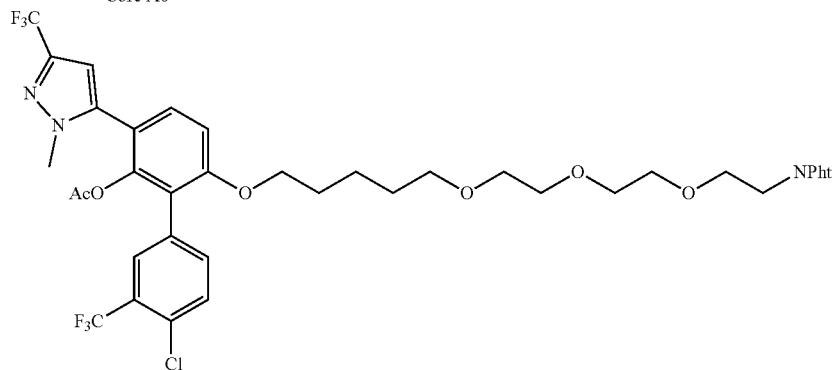

A5BC2_6

To a solution of BC2_NHPht (150 mg, 315.58 umol) in dimethyl formamide (2 mL) was added Core A6 (181.31 mg, 378.70 umol) and potassium carbonate (87.23 mg, 631.16 umol) at 20° C. The reaction was stirred at 40° C. for 4 h. Then the reaction mixture was treated with water (10 mL) and extracted with dichloromethane (3×10 mL). Then the organic phase was washed with brine (10 mL), dried over anhydrous sodium sulfate and filtered. The filtrate was concentrated under reduced pressure to give Cpd A5BC2_6 (0.28 g, crude). The product was used directly for the next step without further purification.

LCMS Method:
LCMS (ESI+): m/z=848.4 (M+23)+, RT: 0.975 min.
5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5um particles). Detection methods are diode array (DAD) and evaporative light scattering (ELSD) detection as well as positive electrospray ionization. MS range was 100-1000.

General Procedure for Preparation of Compound A5BC2_NH2

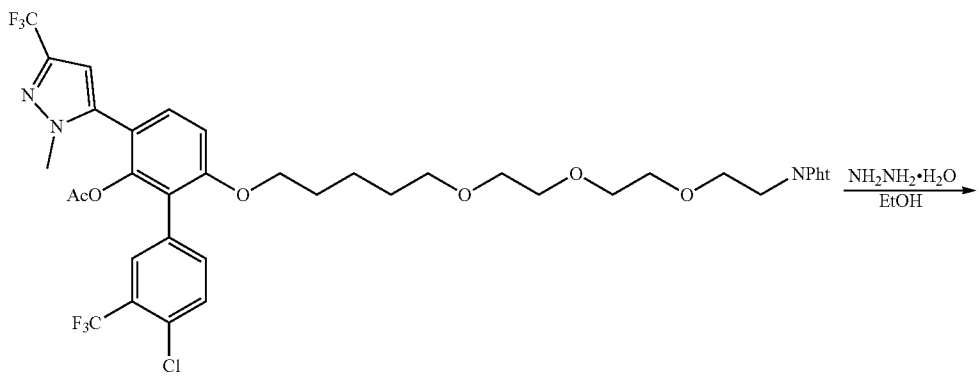

A5BC2_6

-continued

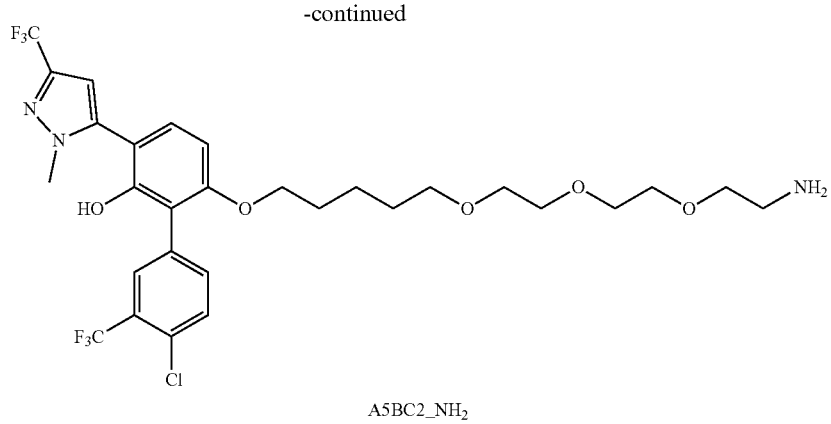

A5BC2_NH2

To a solution of A5BC2_6 (280 mg, 338.91 umol) in ethanol (2 mL) were added $N_2H_4·H_2O$ (39.92 mg, 677.82 umol) at 20° C. The reaction was stirred at 40° C. for 6 h. Then the reaction mixture was treated with water (10 mL) and extracted with dichloromethane (3×10 mL). Then the organic phase was washed with brine (10 mL), dried over anhydrous sodium sulfate and filtered. The filtrate was concentrated under reduced pressure to give crude product. Then the crude product was purified by Prep-HPLC to give A5BC2_NH2 (110 mg, 168.19 umol) as white solid.

LCMS Method:

LCMS (ESI+): m/z=654.1 (M+H)+, RT: 1.197 min.

5_95AB_6 min-220-254-ELSD: LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5um particles). Detection methods are diode array (DAD) and evaporative light scattering (ELSD) detection as well as positive electrospray ionization. MS range was 100-1000.

To a solution of A5BC2_NH2 (30 mg, 45.87 umol) in dimethyl formamide (2 mL) was added R4 (16.67 mg, 50.46 umol), DIEA (17.78 mg, 137.61 umol) and HATU (19.18 mg, 50.46 umol) at 20° C. The reaction was stirred at 25° C. for 12 h. Then the reaction mixture was treated with water (10 mL) and extracted with dichloromethane (3×10 mL). Then the organic phase was washed with brine (10 mL), dried over anhydrous sodium sulfate and filtered. The filtrate was concentrated under reduced pressure to give crude product. Then the crude product was purified by Prep-HPLC to give A5BC2R4 (11.9 mg, yield 26%) as white solid.

Method of Prep-HPLC:

Instrument: Shimadzu LC-8A preparative HPLC

Column: Nano-micro Kromasil C18 100*40 mm 10 um

Mobile phase: A for water (0.09% trifluoroacetic acid) and B for acetonitrile

Gradient: B from 35% to 75% in 20 min

Flow rate: 50 mL/min

Wavelength: 220&254 nm $^1$H NMR: ET32240-1142-P1G (400 MHz, CDCl3-d)

δ 1.35 (br s, 2H), 1.54 (br d, J=8.31 Hz, 2H), 1.66 (br d, J=7.34 Hz, 2H), 2.14 (br s, 1H), 2.66-2.95 (m, 4H), 3.43 (s, 2H), 3.56-3.61 (m, 4H), 3.63-3.69 (m, 8H), 3.85 (s, 3H), 3.98 (t, J=6.11 Hz, 2H), 4.67 (s, 2H), 4.91-4.97 (m, 1H), 6.57 (s, 1H), 6.67 (d, J=8.80 Hz, 1H), 7.20 (dd, J=8.56, 4.16 Hz, 2H), 7.52-7.58 (m, 2H), 7.61-7.65 (m, 1H), 7.72-7.78 (m, 3H), 8.60-8.68 (m, 1H)

LCMS Method:

LCMS (ESI+): m/z=968.2 (M+H)+, RT: 2.880 min.

LC/MS (The gradient was 5-95% B in 3.00 min 0.5% B in 0.01 min, 5-95% B (0.01-1.60 min), 95-100% B (1.60-2.50 min), 100-5% (2.50-2.52 min) with a hold at 5% B for 0.48 min. The flow rate was 0.8 mL/min. Mobile phase A was 0.037% trifluoroacetic acid in water, mobile phase B was 0.018% Trifluoroacetic Acid in acetonitrile. The column used for chromatography was a Halo-C18 3.0*30 mm column (2.7 um particles). Detection methods are diode array (DAD) and evaporative light scattering (ELSD) detection as well as positive electrospray ionization. MS range was 100-1500.)

Example 5—Additional Synthesized Molecules
NUCC-0226200b (A5BC2R1)
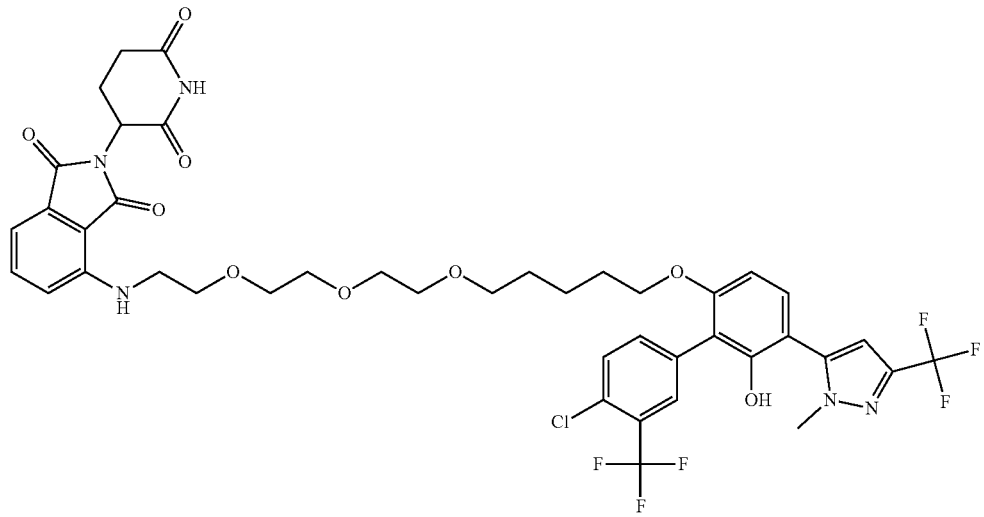 [SMILES: Cn1nc(C(F)(F)F)cc1-c1ccc(OCCCCCOCCOCCOCCNc2cccc3c2C(=O)N(C2CCC(=O)NC2=O)C3=O)c(-c2ccc(Cl)c(C(F)(F)F)c2)c1O]
m/z=910.2 (M+H)+
1H NMR (400 MHz, METHANOL-d$_4$) δ 1.27-1.38 (m, 2H), 1.44-1.53 (m, 2H), 1.57-1.68 (m, 1H), 1.59-1.69 (m, 1H), 2.02-2.12 (m, 1H), 2.63-2.77 (m, 2H), 2.78-2.90 (m, 1H), 3.35-3.40 (m, 1H), 3.48 (t, J=5.32 Hz, 2H), 3.51-3.55 (m, 2H), 3.61 (dd, J=5.99, 3.30 Hz, 2H), 3.64 (s, 4H), 3.71 (t, J=5.32 Hz, 2H), 3.79 (s, 3H), 3.96 (t, J=6.05 Hz, 2H), 4.99-5.09 (m, 1H), 5.03 (dd, J=12.53, 5.44 Hz, 1H), 6.58 (s, 1H), 6.73 (d, J=8.68 Hz, 1H), 7.05 (dd, J=16.02, 7.83 Hz, 2H), 7.21 (d, J=8.56 Hz, 1H), 7.52 (dd, J=8.50, 7.15 Hz, 1H), 7.55-7.60 (m, 1H), 7.62-7.67 (m, 1H), 7.73 (d, J=1.59 Hz, 1H)
NUCC-0226201 (A5BC2R2)
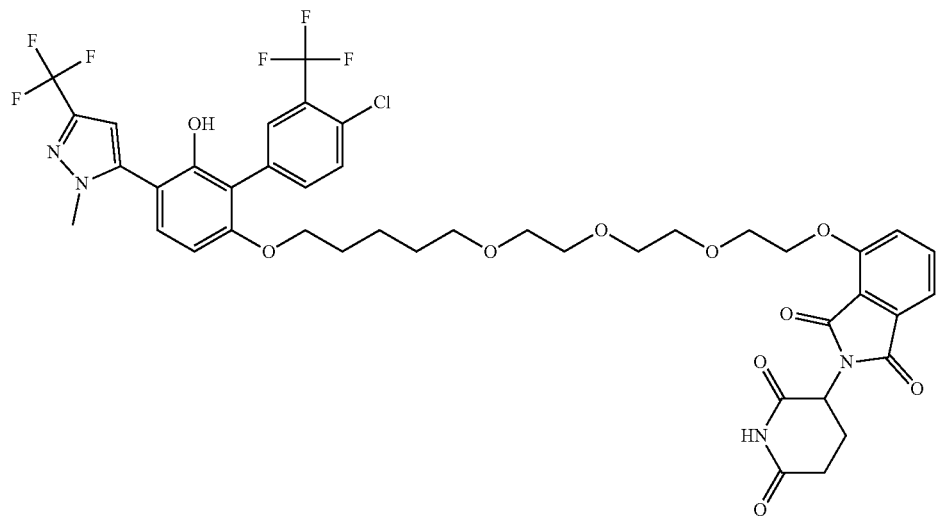 [SMILES: Cn1nc(C(F)(F)F)cc1-c1ccc(OCCCCCOCCOCCOCCOc2cccc3c2C(=O)N(C2CCC(=O)NC2=O)C3=O)c(-c2ccc(Cl)c(C(F)(F)F)c2)c1O]
m/z=911.2 (M+H)+
1H NMR (400 MHz, CHLOROFORM-d) δ 1.31-1.39 (m, 2H), 1.46-1.72 (m, 1H), 1.49-1.72 (m, 3H), 2.09-2.19 (m, 1H), 2.66-2.95 (m, 3H), 3.41 (t, J=6.66 Hz, 2H), 3.55-3.60 (m, 2H), 3.61-3.70 (m, 4H), 3.78 (dd, J=5.69, 3.61 Hz, 2H), 3.84 (s, 3H), 3.91-4.02 (m, 4H), 4.35 (t, J=4.71 Hz, 2H), 4.94 (dd, J=12.17, 5.32 Hz, 1H), 6.57 (s, 1H), 6.66 (d, J=8.68 Hz, 1H), 7.20 (d, J=8.56 Hz, 1H), 7.47 (d, J=7.21 Hz, 1H), 7.51-7.55 (m, 1H), 7.60-7.64 (m, 1H), 7.68 (dd, J=8.38, 7.40 Hz, 1H), 7.76 (d, J=1.83 Hz, 1H), 8.01 (s, 1H)

NUCC-0226202 (A5BC3R3)
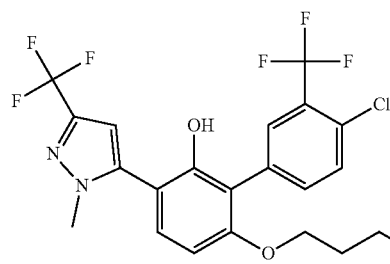
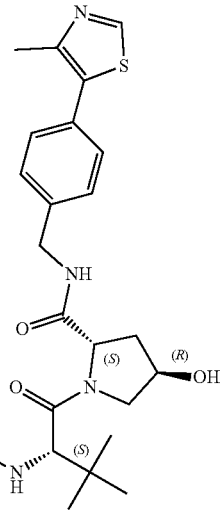
m/z=556.3 (M/2+H)+
1H NMR (400 MHz, CDCl3-d) δ 0.78-0.95 (m, 1H), 1.08 (s, 9H), 1.29-1.38 (m, 2H), 1.54 (quin, J=7.09 Hz, 2H), 1.62-1.72 (m, 2H), 2.52 (s, 3H), 3.11-3.21 (m, 1H), 3.30-3.37 (m, 1H), 3.41 (br t, J=6.60 Hz, 2H), 3.52 (br d, J=10.27 Hz, 1H), 3.55-3.59 (m, 2H), 3.60-3.70 (m, 10H), 3.70-3.75 (m, 1H), 3.84 (s, 3H), 3.87-3.93 (m, 1H), 3.94-4.02 (m, 3H), 4.32-4.42 (m, 2H), 4.49-4.59 (m, 2H), 4.81 (br t, J=8.31 Hz, 1H), 6.56 (s, 1H), 6.67 (d, J=8.80 Hz, 1H), 7.20 (d, J=8.31 Hz, 1H), 7.36 (s, 4H), 7.46-7.57 (m, 2H), 7.58-7.63 (m, 1H), 7.76 (d, J=1.47 Hz, 1H), 8.91 (s, 1H)
NUCC-0226203 (A5BC2R4)
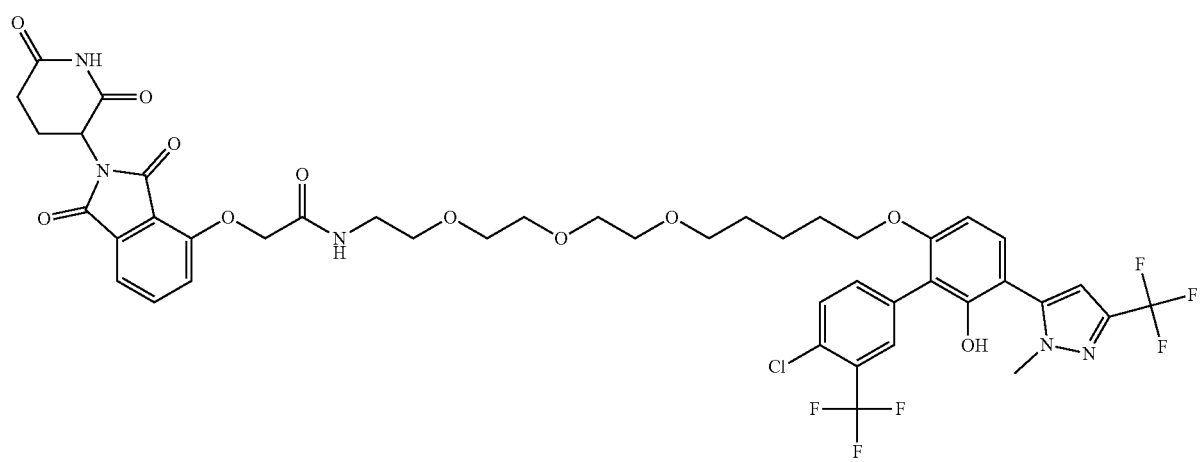 [SMILES: Cn1nc(C(F)(F)F)cc1-c1ccc(OCCCCCOCCOCCOCCNC(=O)COc2cccc3c2C(=O)N(C2CCC(=O)NC2=O)C3=O)c(-c2ccc(Cl)c(C(F)(F)F)c2)c1O]
m/z=968.2 (M+H)+
1H NMR: (400 MHz, CDCl3-d) δ 1.35 (br s, 2H), 1.54 (br d, J=8.31 Hz, 2H), 1.66 (br d, J=7.34 Hz, 2H), 2.14 (br s, 1H), 2.66-2.95 (m, 4H), 3.43 (s, 2H), 3.56-3.61 (m, 4H), 3.63-3.69 (m, 8H), 3.85 (s, 3H), 3.98 (t, J=6.11 Hz, 2H), 4.67 (s, 2H), 4.91-4.97 (m, 1H), 6.57 (s, 1H), 6.67 (d, J=8.80 Hz, 1H), 7.20 (dd, J=8.56, 4.16 Hz, 2H), 7.52-7.58 (m, 2H), 7.61-7.65 (m, 1H), 7.72-7.78 (m, 3H), 8.60-8.68 (m, 1H)

NUCC-0226204 (A5BCM1R1)
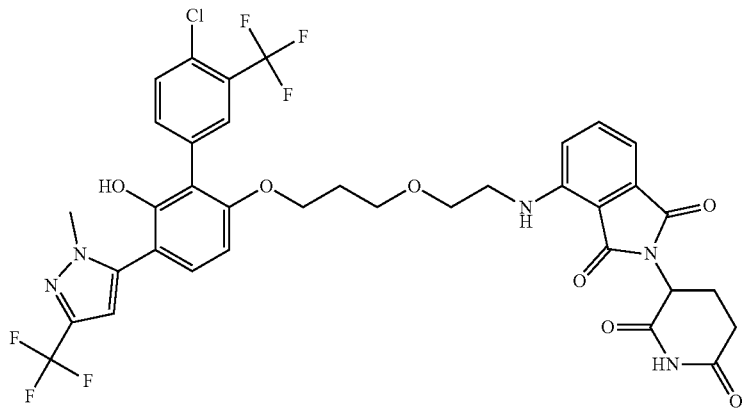 [SMILES: Cn1nc(C(F)(F)F)cc1-c1ccc(OCCCOCCNc2cccc3c2C(=O)N(C2CCC(=O)NC2=O)C3=O)c(-c2ccc(Cl)c(C(F)(F)F)c2)c1O]
m/z=794.2 (M+H)+
1H NMR (400 MHz, DMSO-d6) δ 1.45-1.48 (m, 1H), 1.73-1.88 (m, 2H), 1.93-2.09 (m, 1H), 2.79 (s, 1H), 3.51-3.60 (m, 4H), 3.70-3.79 (m, 3H), 3.97-4.09 (m, 2H), 4.99-5.14 (m, 1H), 6.54-6.65 (m, 1H), 6.65-6.94 (m, 2H), 6.70-6.81 (m, 2H), 7.06-7.15 (m, 1H), 7.19-7.28 (m, 1H), 7.44-7.68 (m, 1H), 7.49-7.60 (m, 1H), 7.71 (d, J=2.81 Hz, 2H), 8.82-9.10 (m, 1H), 11.06-11.20 (m, 1H)
NUCC-0226205 (A5BCM1R4)
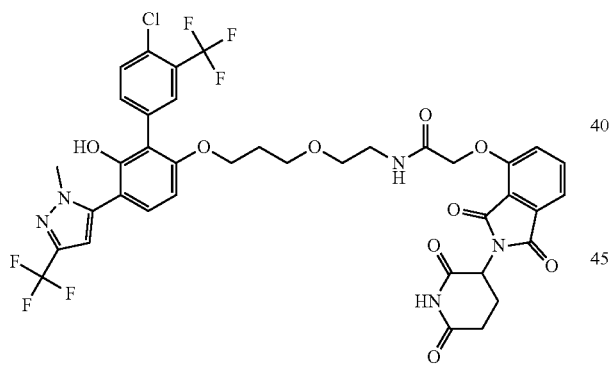
m/z=852.1 (M+H)+
1H NMR (400 MHz, DMSO-d6) δ 1.72-1.90 (m, 2H), 1.93-2.03 (m, 1H), 2.83-2.94 (m, 1H), 3.25-3.34 (m, 4H), 3.71-3.81 (m, 3H), 4.03 (br t, J=5.38 Hz, 2H), 4.71-4.81 (m, 2H), 5.06-5.17 (m, 1H), 6.67-6.78 (m, 2H), 7.14-7.27 (m, 1H), 7.33-7.45 (m, 1H), 7.47-7.53 (m, 1H), 7.64 (br d, J=8.44 Hz, 1H), 7.71-7.86 (m, 3H), 7.92-8.02 (m, 1H), 8.88-9.07 (m, 1H), 10.98-11.24 (m, 1H)
NUCC-0226206 (A5BC0R1)
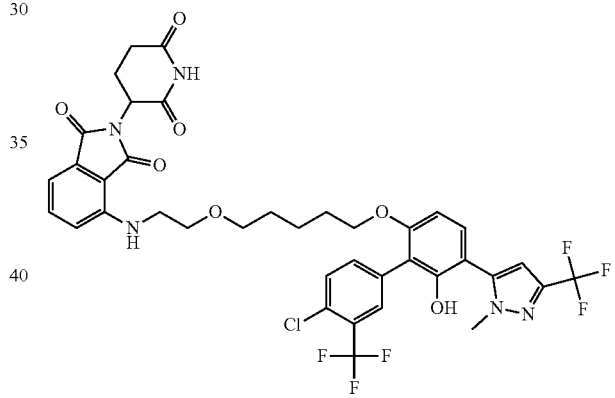
m/z=822.2 (M+H)+
1H NMR (400 MHz, DMSO-d6) δ 1.20-1.31 (m, 2H), 1.38-1.47 (m, 2H), 1.49-1.60 (m, 2H), 1.90-2.06 (m, 1H), 2.76-2.90 (m, 1H), 3.29-3.37 (m, 2H), 3.39-3.64 (m, 9H), 3.69-3.77 (m, 3H), 3.88-3.98 (m, 2H), 4.93-5.11 (m, 1H), 6.51-6.62 (m, 1H), 6.67-6.77 (m, 1H), 6.95-7.04 (m, 1H), 7.09-7.15 (m, 1H), 7.21-7.24 (m, 1H), 7.49-7.63 (m, 2H), 7.68-7.76 (m, 2H), 8.89-9.01 (m, 1H)

NUCC-0226207 (A5BC1R1)
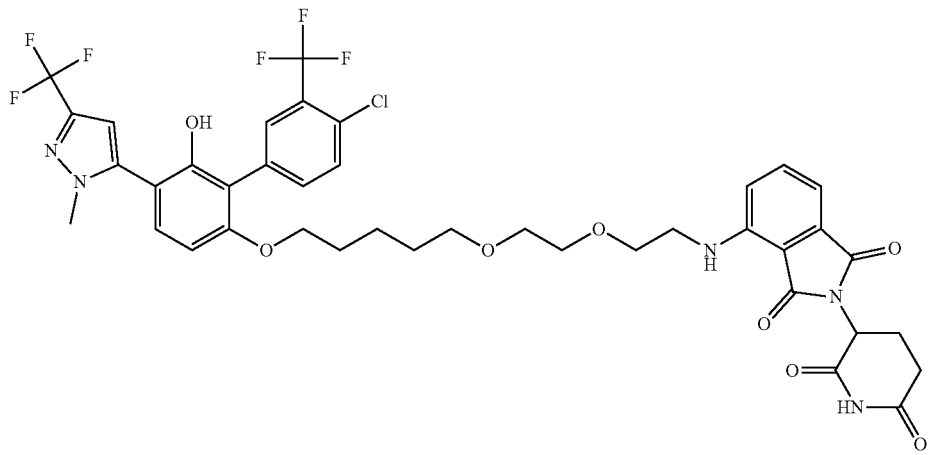 [SMILES: Cn1nc(C(F)(F)F)cc1-c1ccc(OCCCCCOCCOCCNc2cccc3c2C(=O)N(C2CCC(=O)NC2=O)C3=O)c(-c2ccc(Cl)c(C(F)(F)F)c2)c1O]
m/z=866.2 (M+H)+
1H NMR (400 MHz, METHANOL-d4) δ 1.27-1.39 (m, 2H), 1.29-1.38 (m, 1H), 1.49 (quin, J=7.00 Hz, 2H), 1.57-1.70 (m, 3H), 2.00-2.12 (m, 1H), 2.59-2.74 (m, 2H), 2.76-2.91 (m, 1H), 3.40 (t, J=6.39 Hz, 2H), 3.46-3.51 (m, 2H), 3.55-3.59 (m, 2H), 3.61-3.66 (m, 2H), 3.71 (t, J=5.18 Hz, 2H), 3.79 (s, 3H), 3.95 (t, J=6.06 Hz, 2H), 5.02 (dd, J=12.35, 5.51 Hz, 1H), 6.58 (s, 1H), 6.72 (d, J=8.60 Hz, 1H), 7.02 (d, J=7.06 Hz, 1H), 7.07 (d, J=8.38 Hz, 1H), 7.21 (d, J=8.60 Hz, 1H), 7.49-7.54 (m, 1H), 7.55-7.59 (m, 1H), 7.61-7.66 (m, 1H), 7.72 (s, 1H)
NUCC-0226208 (A5BC1R4)
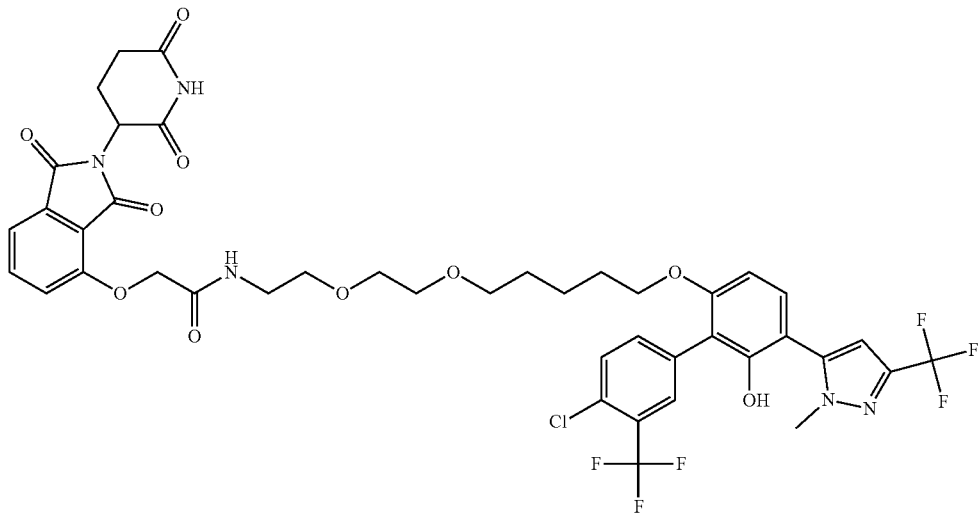 [SMILES: Cn1nc(C(F)(F)F)cc1-c1ccc(OCCCCCOCCOCCNC(=O)COc2cccc3c2C(=O)N(C2CCC(=O)NC2=O)C3=O)c(-c2ccc(Cl)c(C(F)(F)F)c2)c1O]
m/z=925.1 (M+H)+
1H NMR (400 MHz, METHANOL-d4) δ 1.27-1.37 (m, 2H), 1.42-1.52 (m, 2H), 1.57-1.67 (m, 2H), 2.13 (m, 1H), 2.66-2.78 (m, 2H), 2.79-2.91 (m, 1H), 3.38 (t, J=6.50 Hz, 2H), 3.47-3.52 (m, 2H), 3.56 (br d, J=5.73 Hz, 2H), 3.59-3.64 (m, 4H), 3.79 (s, 3H), 3.96 (t, J=5.95 Hz, 2H), 4.75 (s, 2H), 5.12 (dd, J=12.35, 5.29 Hz, 1H), 6.59 (s, 1H), 6.73 (d, J=8.82 Hz, 1H), 7.22 (d, J=8.38 Hz, 1H), 7.41 (d, J=8.16 Hz, 1H), 7.52 (d, J=7.28 Hz, 1H), 7.55-7.59 (m, 1H), 7.62-7.66 (m, 1H), 7.72 (s, 1H), 7.78 (t, J=7.94 Hz, 1H)

NUCC-0226209 (A5BC3R4)
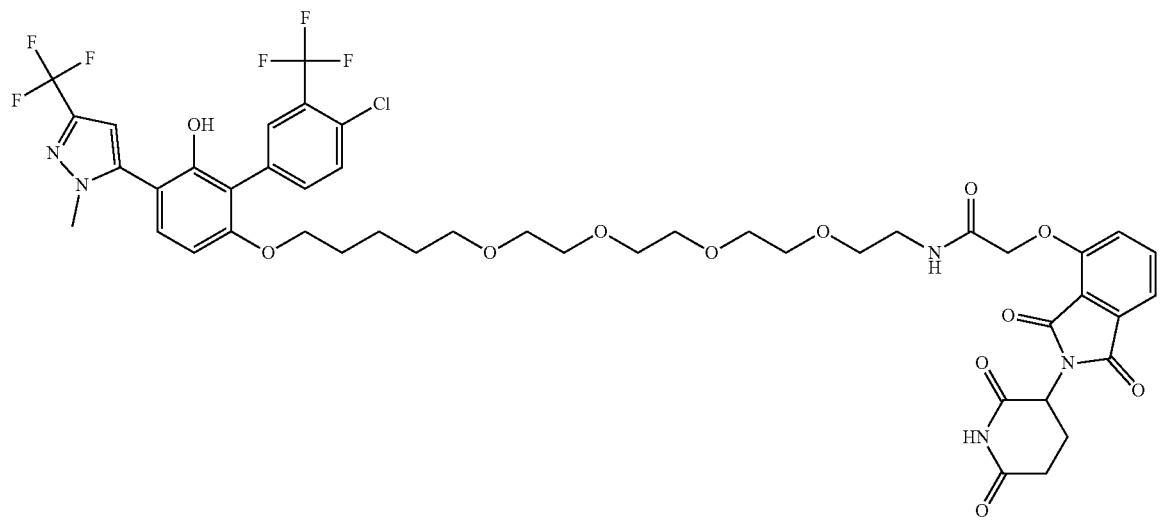 [SMILES: Cn1nc(C(F)(F)F)cc1-c1ccc(OCCCCCOCCOCCOCCOCCNC(=O)COc2cccc3c2C(=O)N(C2CCC(=O)NC2=O)C3=O)c(-c2ccc(Cl)c(C(F)(F)F)c2)c1O]
m/z=1012.0 (M+H)+
1H NMR (400 MHz, METHANOL-d4) δ 1.27-1.39 (m, 2H), 1.49 (quin, J=7.11 Hz, 2H), 1.58-1.70 (m, 2H), 2.13 (br d, J=5.29 Hz, 1H), 2.65-2.79 (m, 2H), 2.85 (br dd, J=14.55, 4.63 Hz, 1H), 3.38 (t, J=6.39 Hz, 2H), 3.47-3.55 (m, 4H), 3.55-3.66 (m, 12H), 3.79 (s, 3H), 3.98 (t, J=5.95 Hz, 2H), 4.76 (s, 2H), 5.12 (dd, J=12.35, 5.29 Hz, 1H), 6.58 (s, 1H), 6.75 (d, J=8.60 Hz, 1H), 7.22 (d, J=8.60 Hz, 1H), 7.42 (d, J=8.60 Hz, 1H), 7.52 (d, J=7.50 Hz, 1H), 7.56-7.62 (m, 1H), 7.63-7.68 (m, 1H), 7.73 (s, 1H), 7.79 (t, J=7.94 Hz, 1H)
NUCC-0226210 (A5BC3R1)
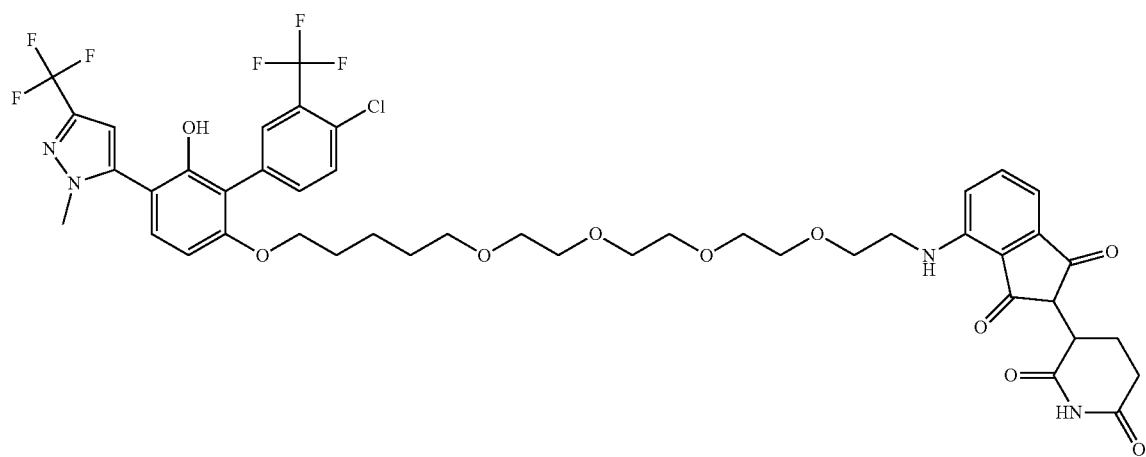 [SMILES: Cn1nc(C(F)(F)F)cc1-c1ccc(OCCCCCOCCOCCOCCOCCNc2cccc3c2C(=O)C(C2CCC(=O)NC2=O)C3=O)c(-c2ccc(Cl)c(C(F)(F)F)c2)c1O]
m/z=954.1 (M+H)+
1H NMR (400 MHz, METHANOL-d4) δ 1.33 (quin, J=7.64 Hz, 2H), 1.44-1.54 (m, 2H), 1.57-1.70 (m, 2H), 2.01-2.13 (m, 1H), 2.62-2.77 (m, 2H), 2.78-2.92 (m, 1H), 3.38 (t, J=6.42 Hz, 2H), 3.45-3.54 (m, 4H), 3.56-3.63 (m, 6H), 3.64 (s, 4H), 3.71 (t, J=5.26 Hz, 2H), 3.79 (s, 3H), 3.98 (t, J=6.05 Hz, 2H), 5.04 (dd, J=12.53, 5.44 Hz, 1H), 6.58 (s, 1H), 6.74 (d, J=8.56 Hz, 1H), 7.04 (d, J=7.09 Hz, 1H), 7.08 (d, J=8.56 Hz, 1H), 7.22 (d, J=8.56 Hz, 1H), 7.53 (dd, J=8.44, 7.21 Hz, 1H), 7.56-7.61 (m, 1H), 7.62-7.68 (m, 1H), 7.73 (d, J=1.47 Hz, 1H)

Example 6—Additional Examples of Contemplated Compounds
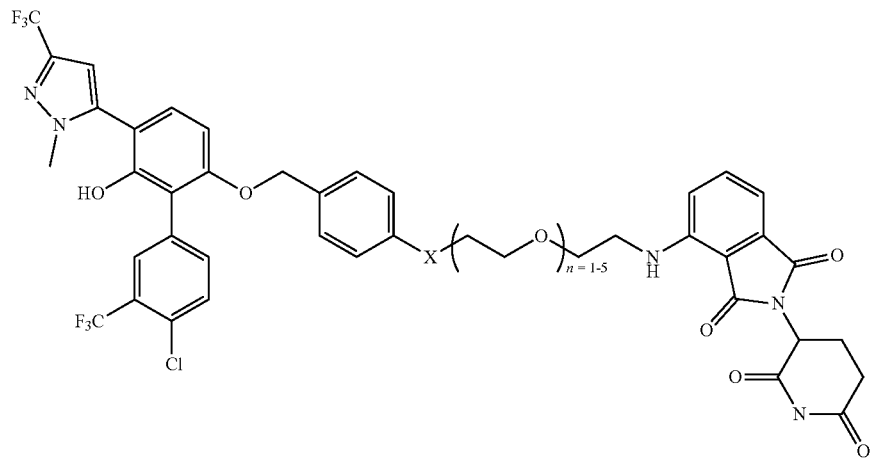
X = O, NH, NMe, CH2
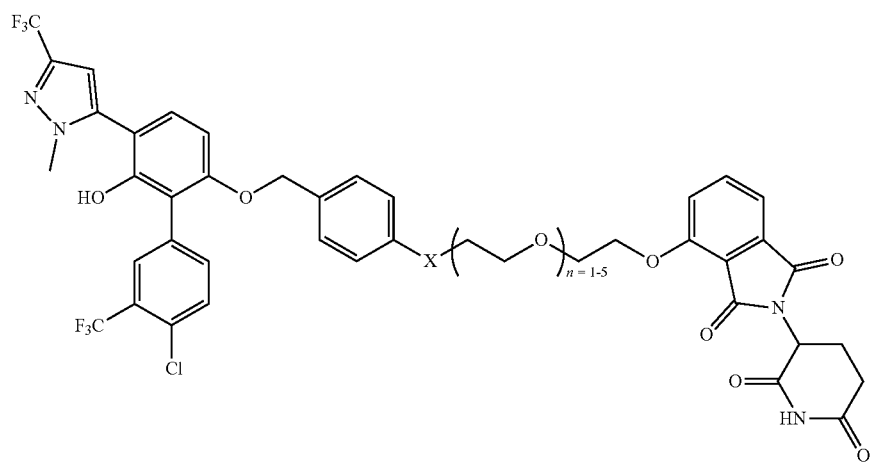
X = O, NH, NMe, CH2
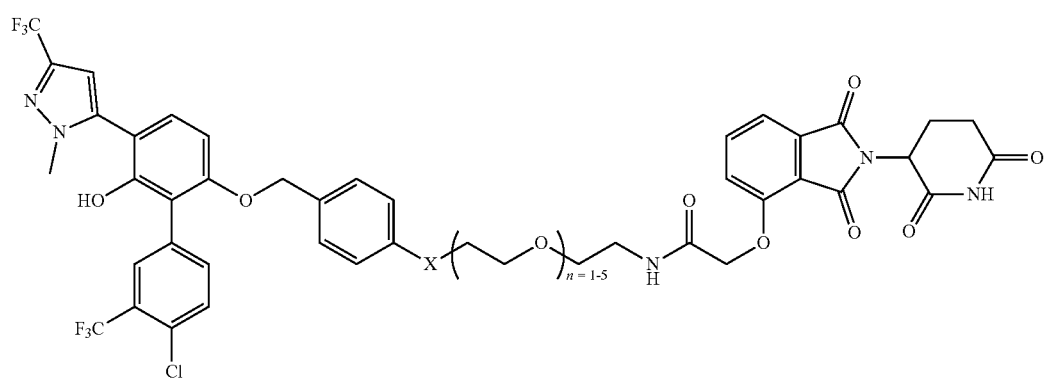
X = O, NH, NMe, CH2

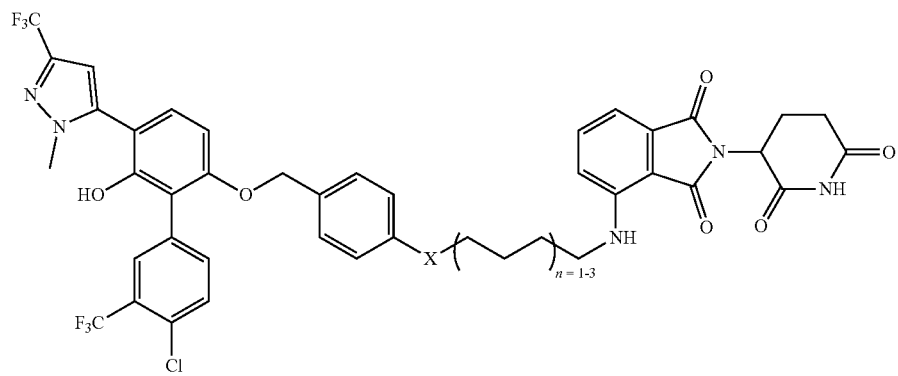
X = O, NH, NMe, CH2
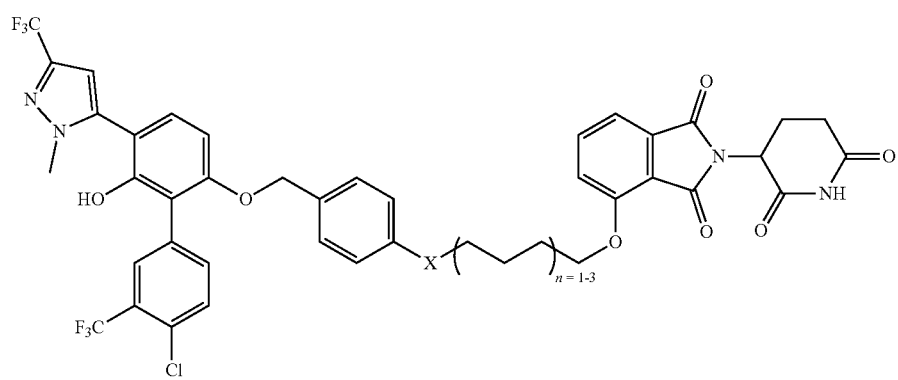
X = O, NH, NMe, CH2
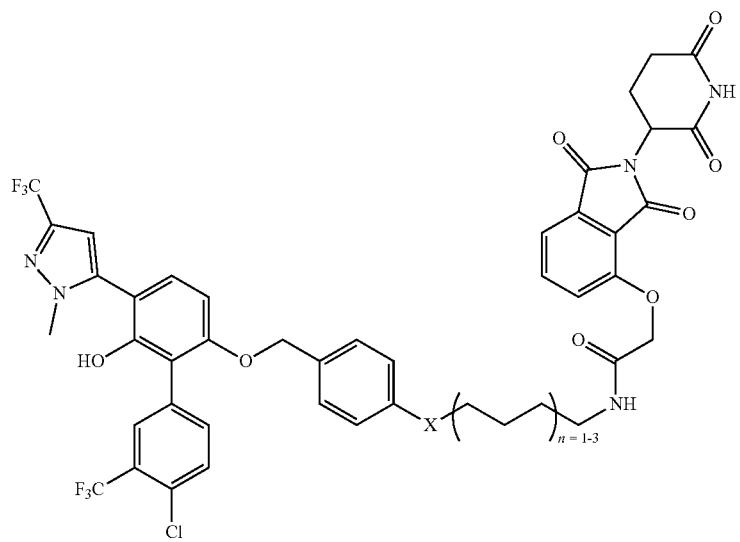
X = O, NH, NMe, CH2

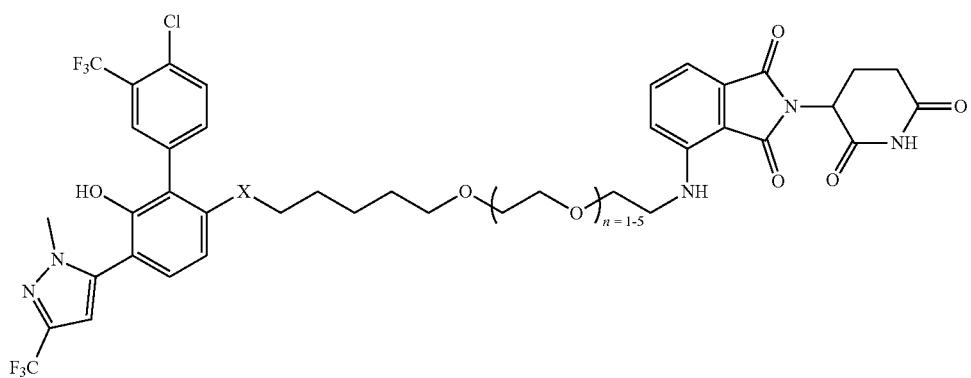
X = O, NH, NMe, CH2
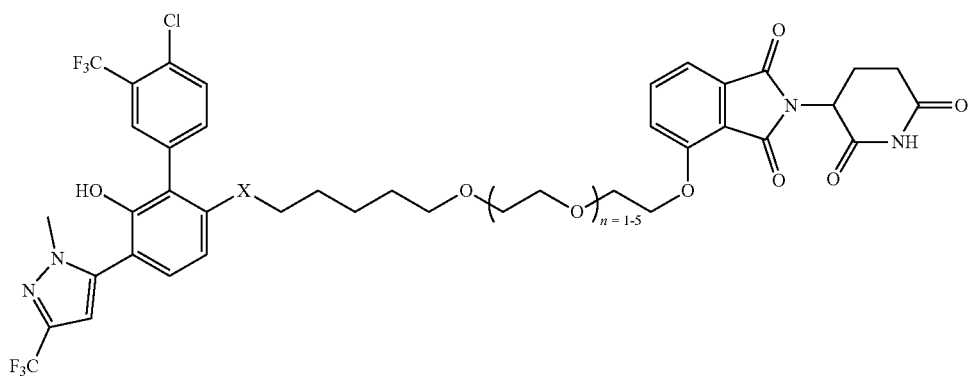
X = O, NH, NMe, CH2
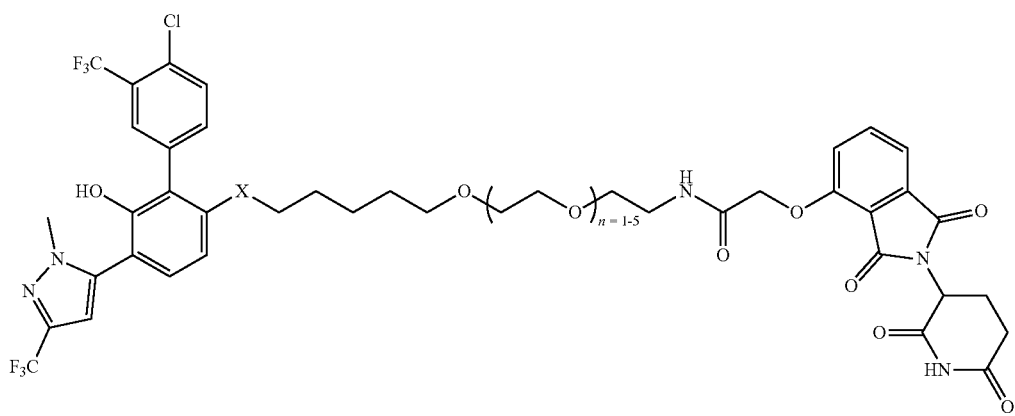
X = O, NH, NMe, CH2
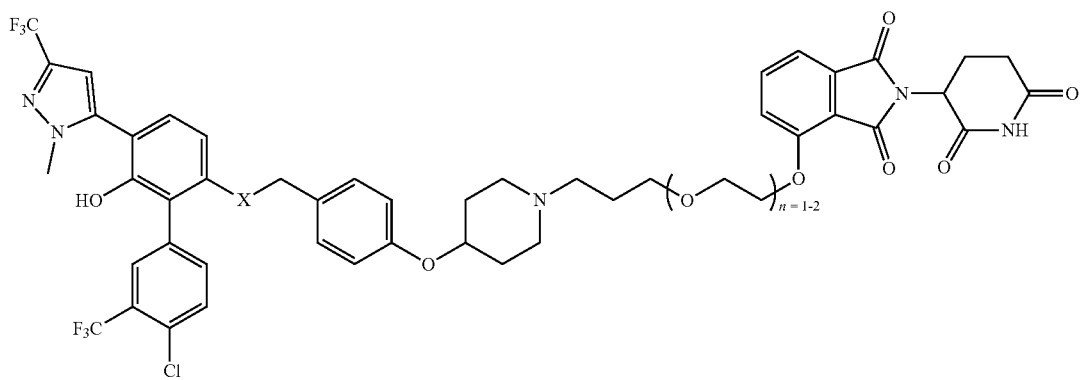
X = O, NH, NMe, CH2

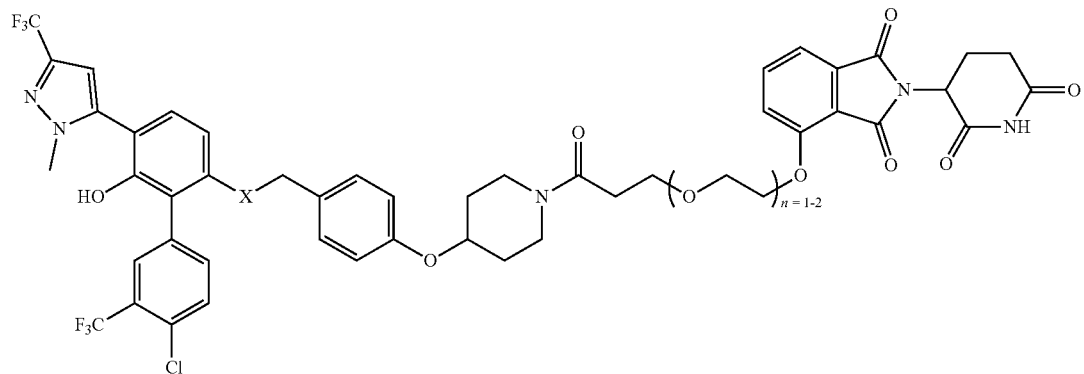
X = O, NH, NMe, CH2
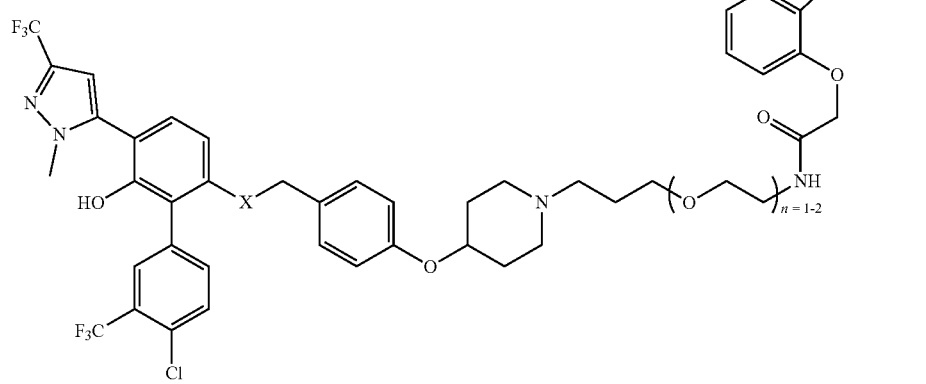
X = O, NH, NMe, CH2
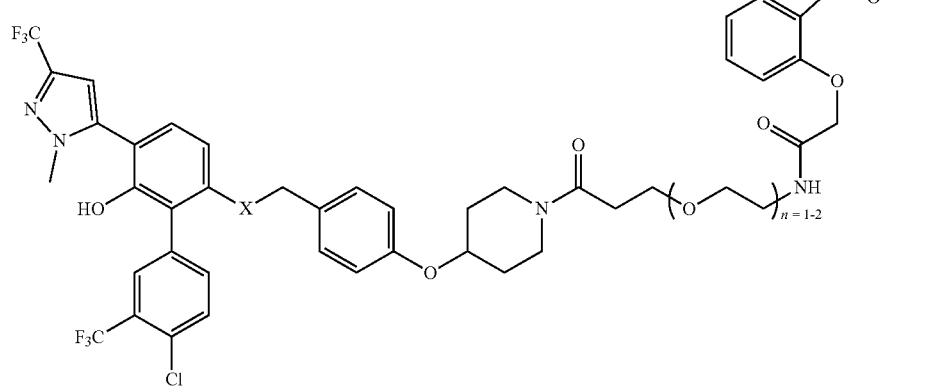
X = O, NH, NMe, CH2

-continued
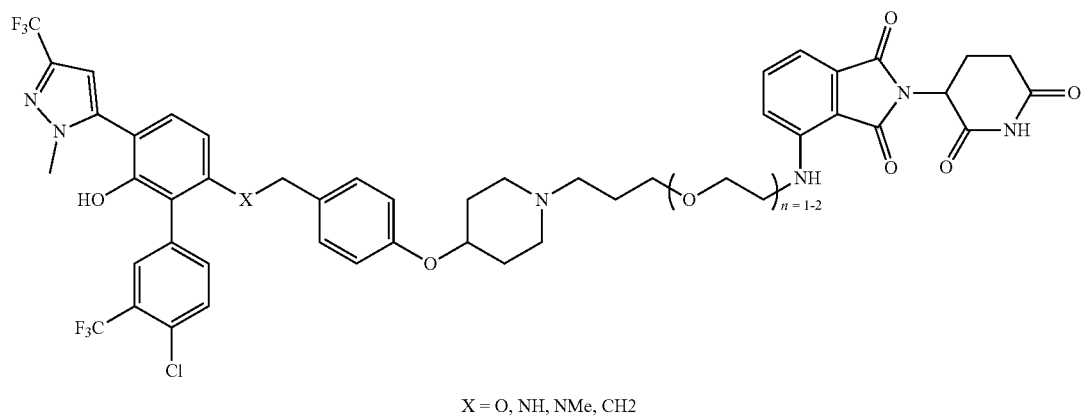
X = O, NH, NMe, CH2
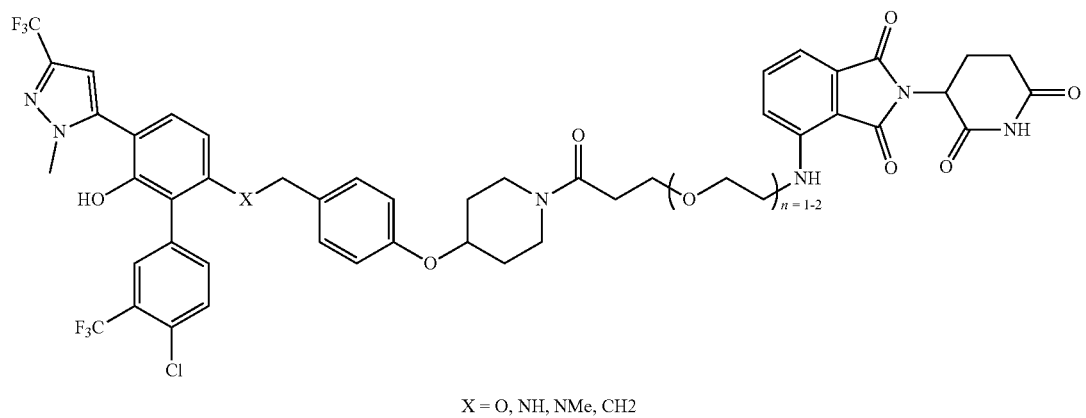
X = O, NH, NMe, CH2
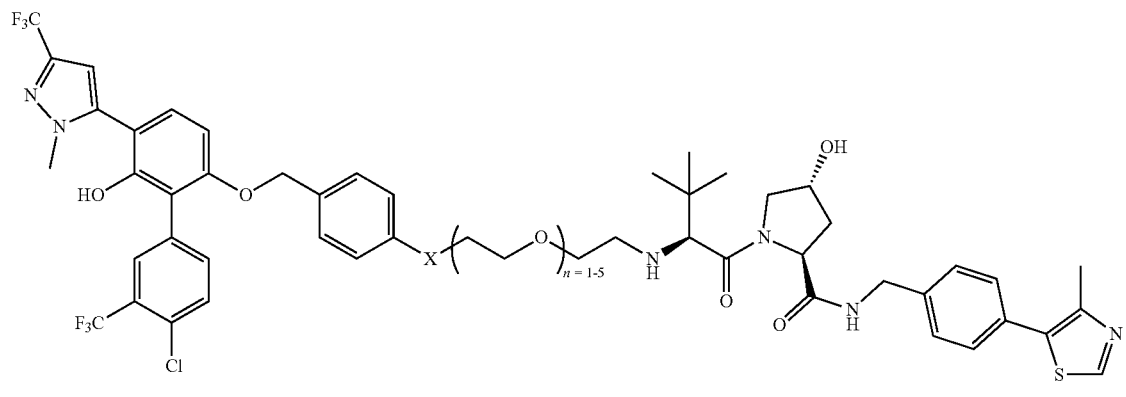
X = O, NH, NMe, CH2

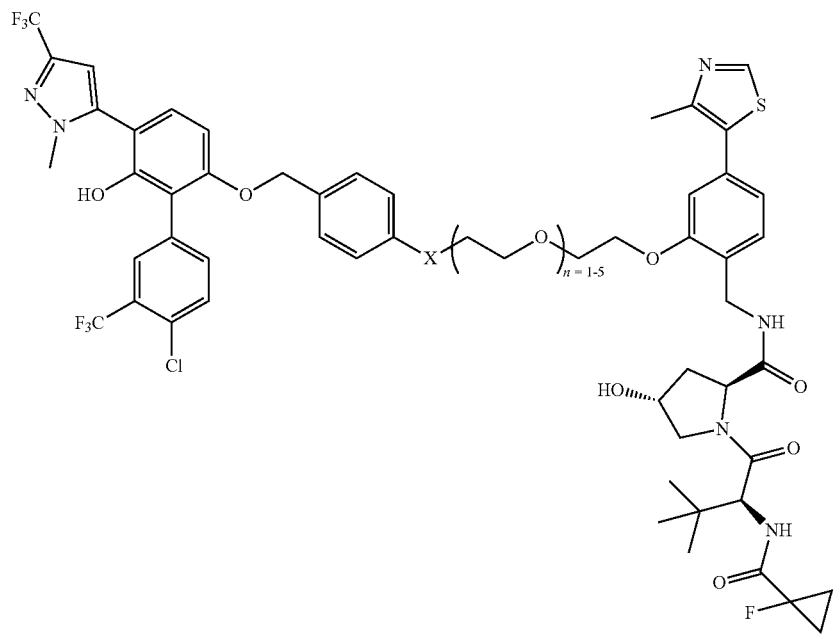
X = O, NH, NMe, CH2
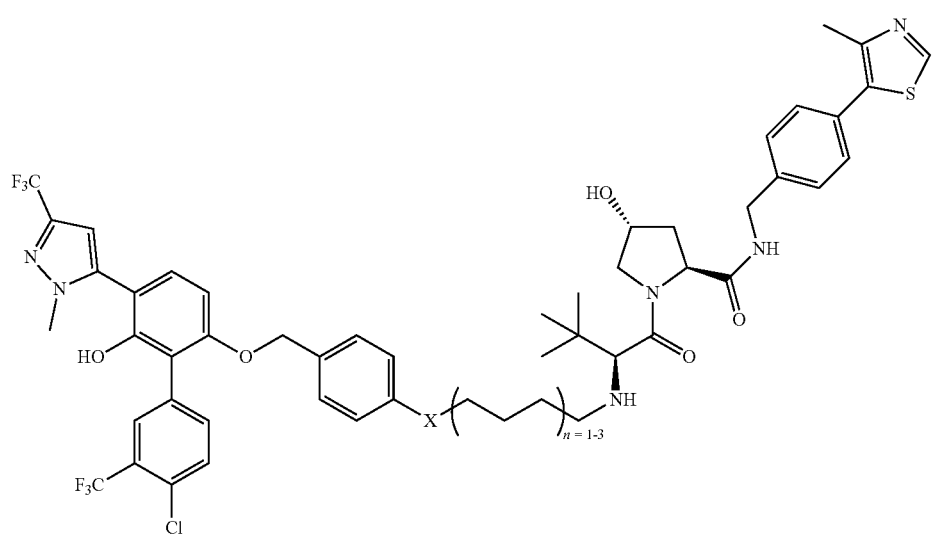
X = O, NH, NMe, CH2

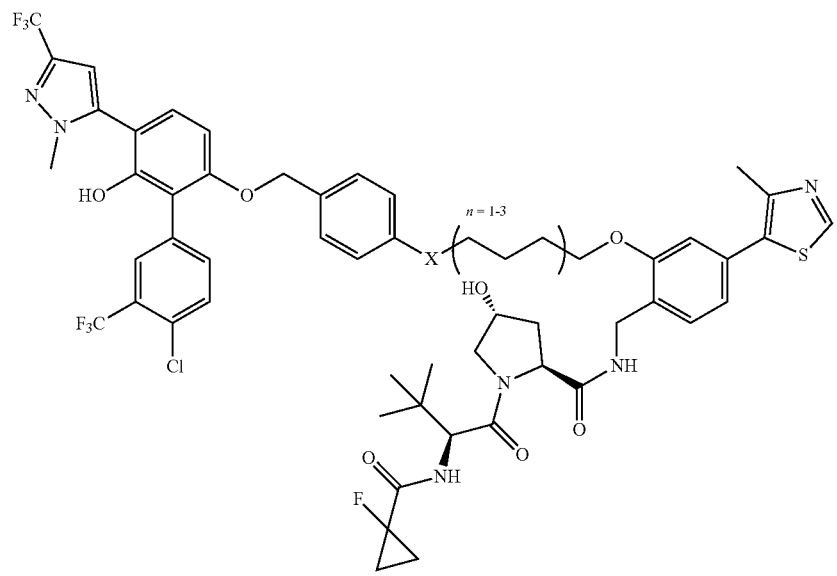
X = O, NH, NMe, CH2
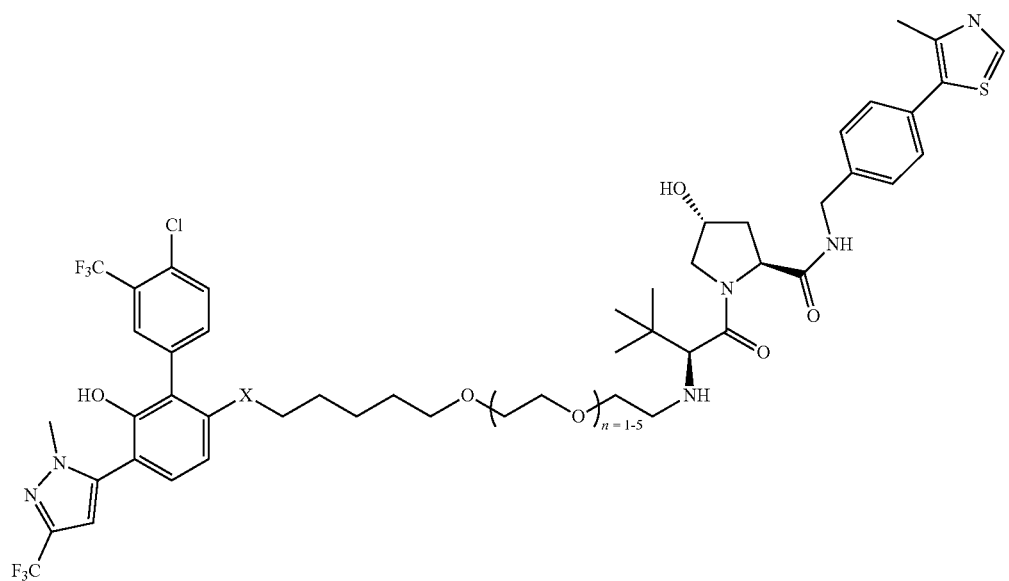
X = O, NH, NMe, CH2

-continued
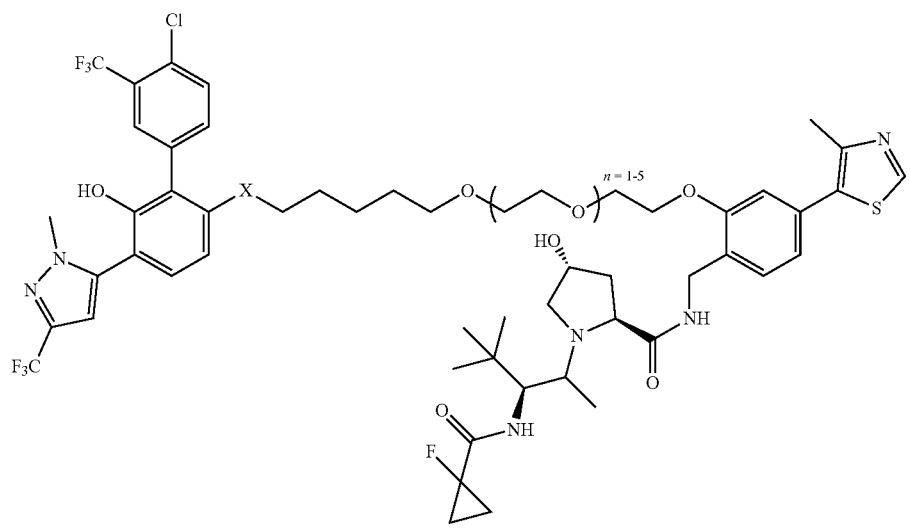
X = O, NH, NMe, CH2
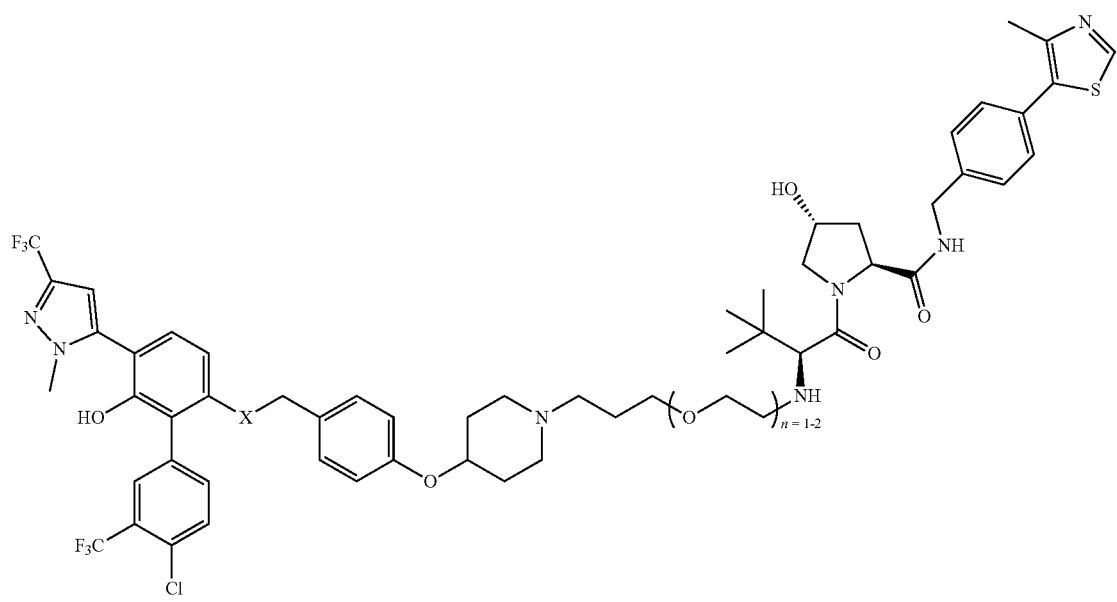
X = O, NH, NMe, CH2

-continued

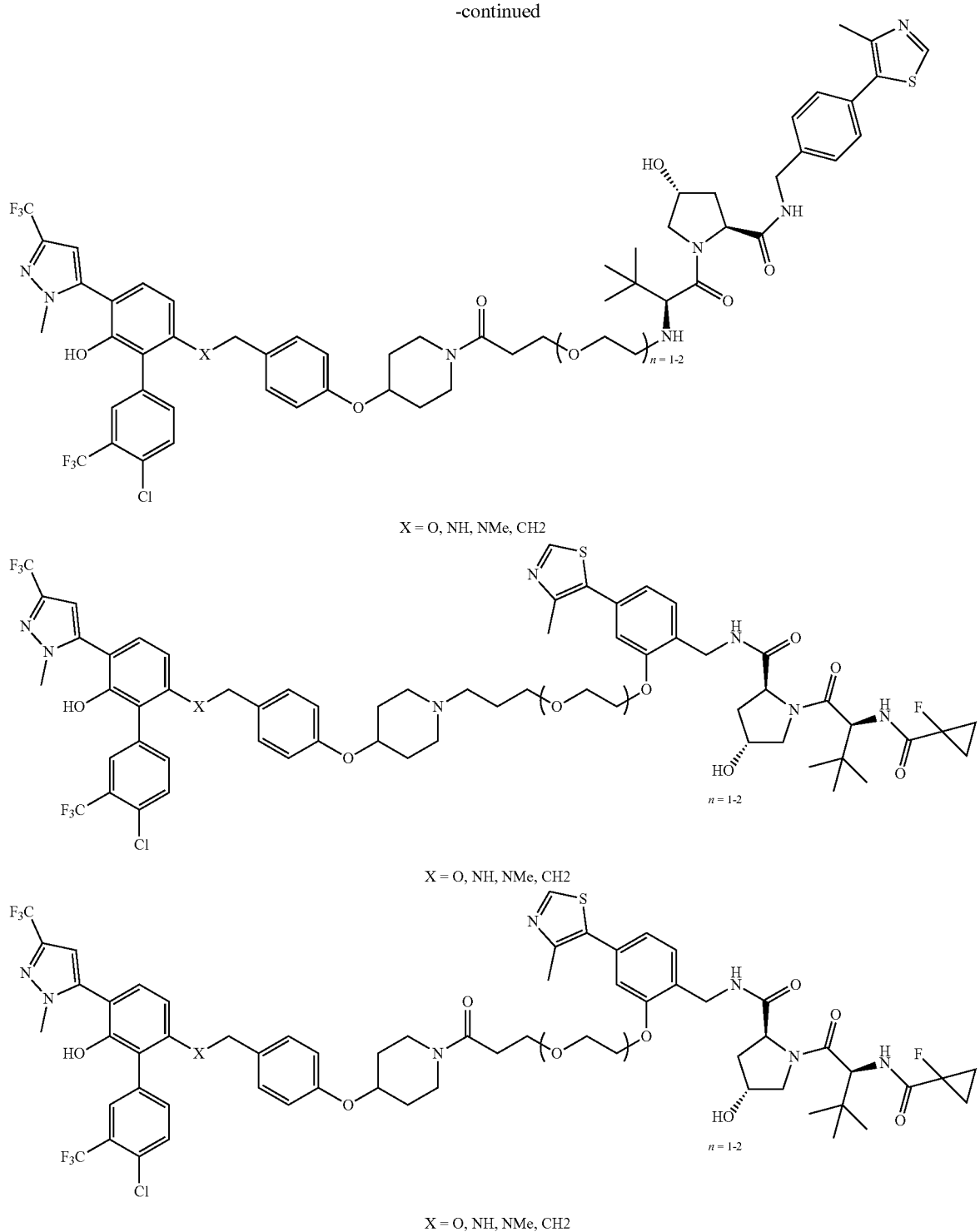

X = O, NH, NMe, CH2

X = O, NH, NMe, CH2

X = O, NH, NMe, CH2

Example 7. Western Blot (WB) Method for MYC Degradation Evaluation

Western Blot analysis. PC3 cells (2.5×10⁵/well) were plated into 6 well plate one day before the treatment. Compounds at 0.1, 1 and 10 μM were added next day. After 24 h treatment, cells were washed once with PBS and lysed in RIPA buffer (Sigma) supplemented with protease and phosphatase (Roche). Protein lysates were loaded with 4× Laemmli sample buffer (Bio-Rad) into 4-12% Bis-Tris Midi Protein Gels (Thermo), run with MES SDS running buffer (Thermo) at constant voltage (130V) for about 2 hours, and subsequently transferred to PVDF membranes (Bio-Rad) using Trans-Blot Turbo Transfer System (Bio-Rad). Membranes were blocked for 1 h at room temperature with 10% blotting-grade milk (Bio-Rad), followed by overnight 4° C. incubation with the appropriate primary antibodies and 1 h room temperature incubation with an anti-rabbit IgG (H+L)-

Figure 3:
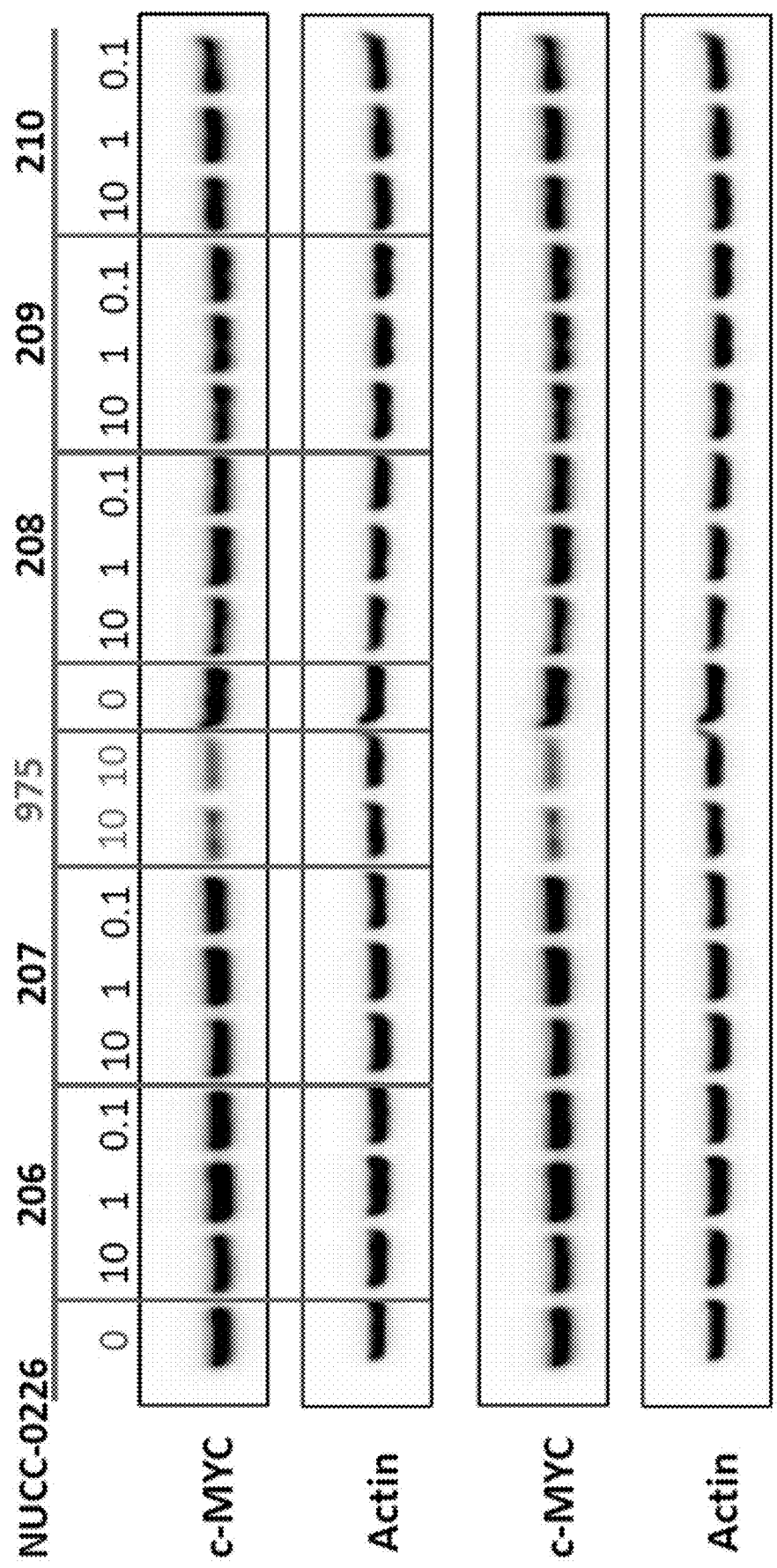
FIG. 3. MYC degradation screen in PC3 cells treated for 24 hours with the listed compounds (206-210) at the listed concentration (10, 1 or 0.1 µM).
Figure 4:
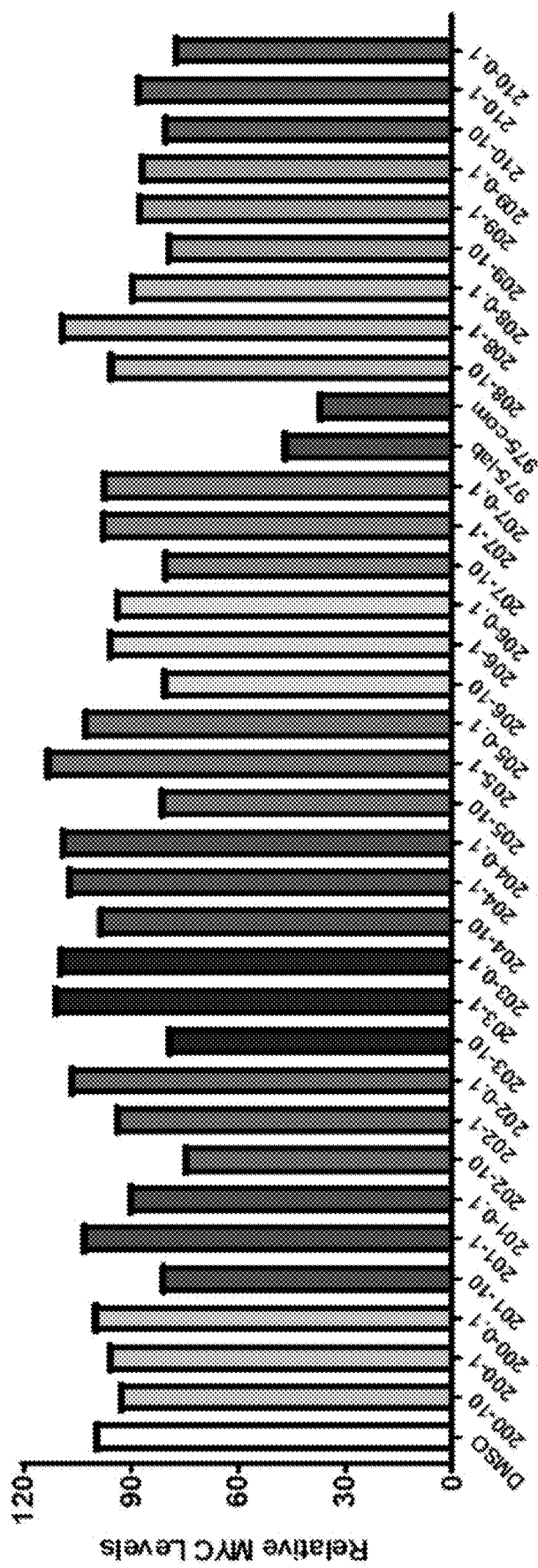
FIG. 4. Graphic illustration of relative MYC levels for the screens of FIG. 2 and FIG. 3.

HRP conjugate secondary antibody (Bio-Rad). Blots were imaged with ChemiDoc Imaging System (Bio-Rad). Primary antibodies MYC (Y69) (Abcam, ab32072) and β-actin (Cell Signaling, 5125S) were used in this study. Results are presented in FIGS. 1-4.
Example 8. Summary of Synthesis Schemes
The disclosed molecules may be synthesized using one or more of the following schemes.
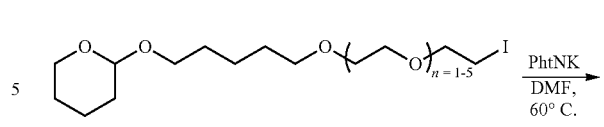
Scheme 1.
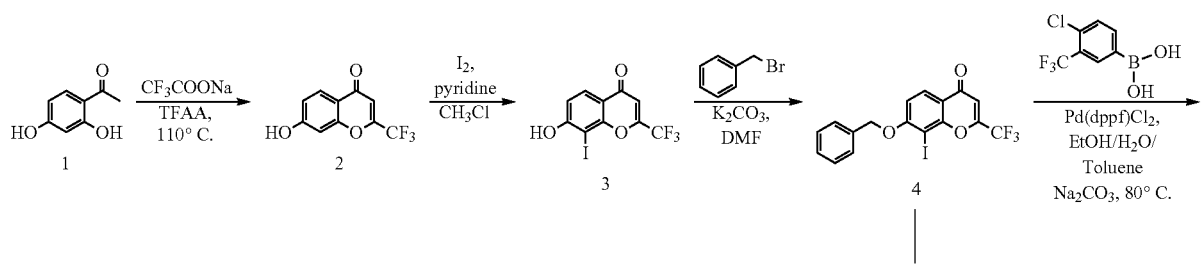
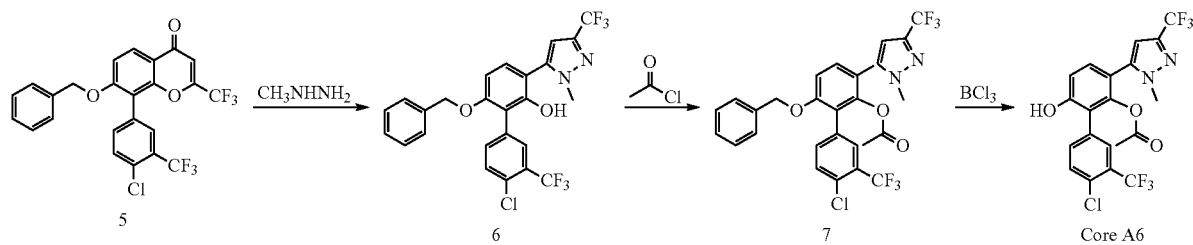
Scheme 2.
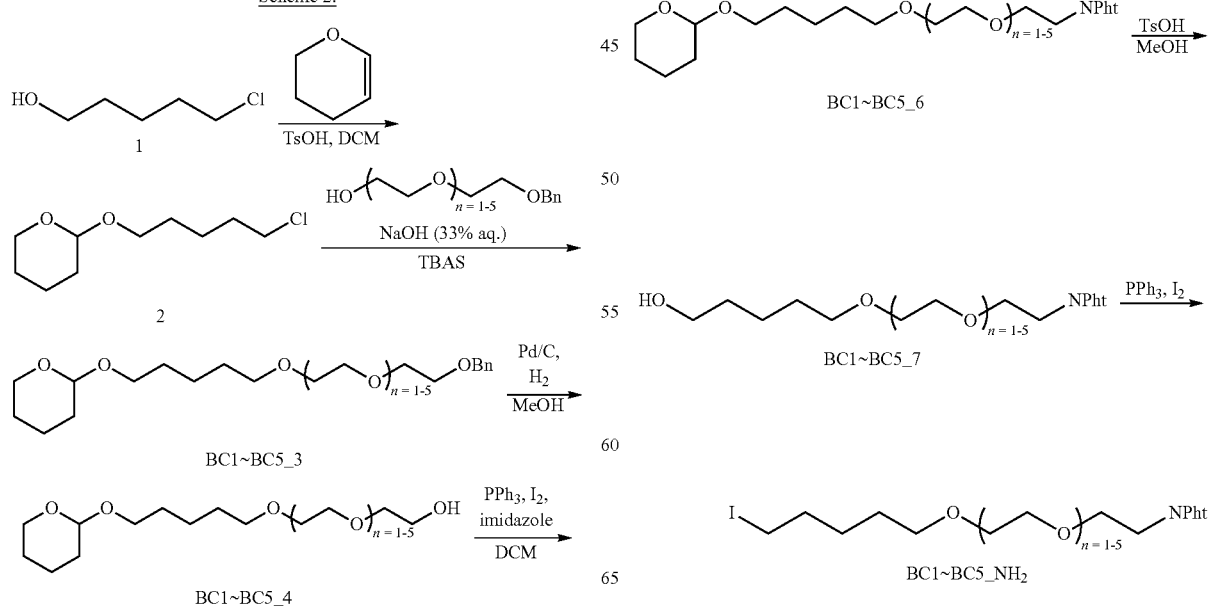

Scheme 3.
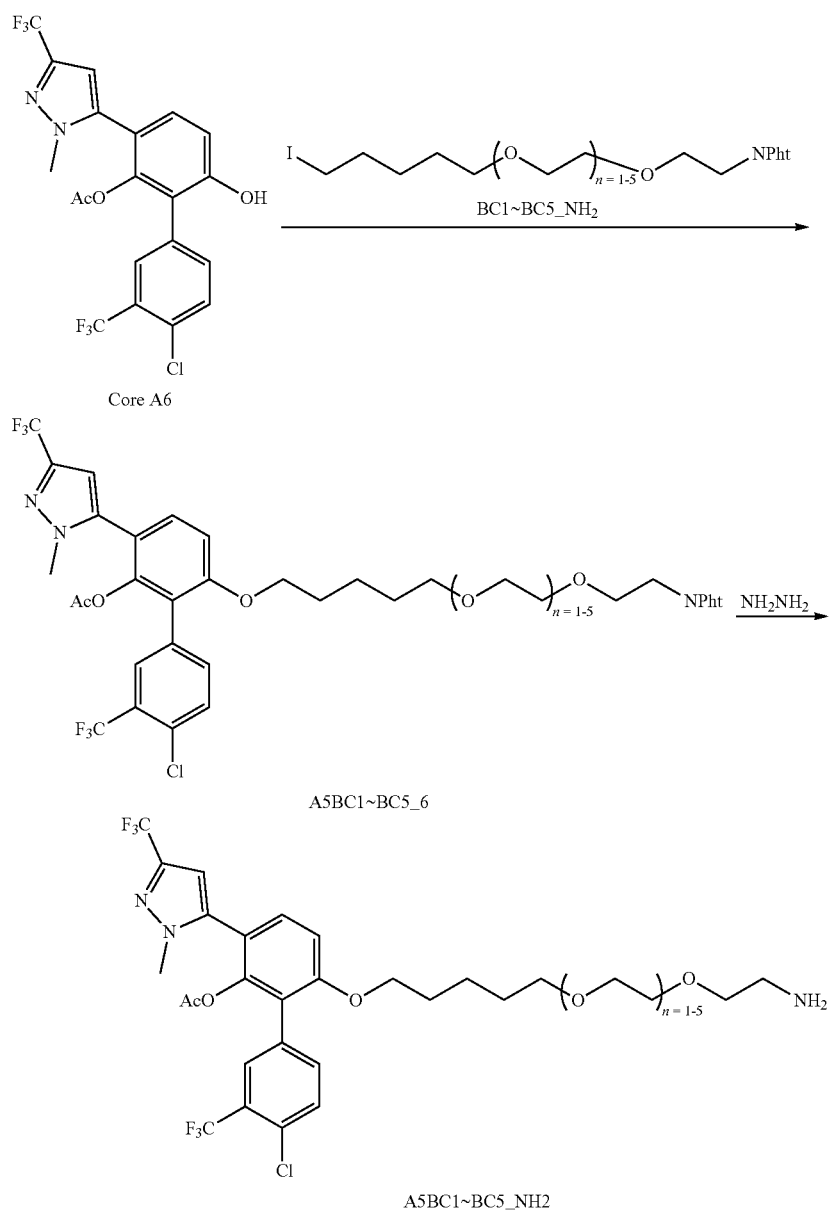
A5BC1~BC5_NH2
Scheme 4.
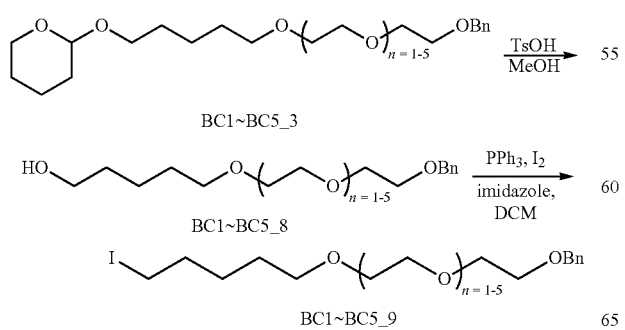

Scheme 5.
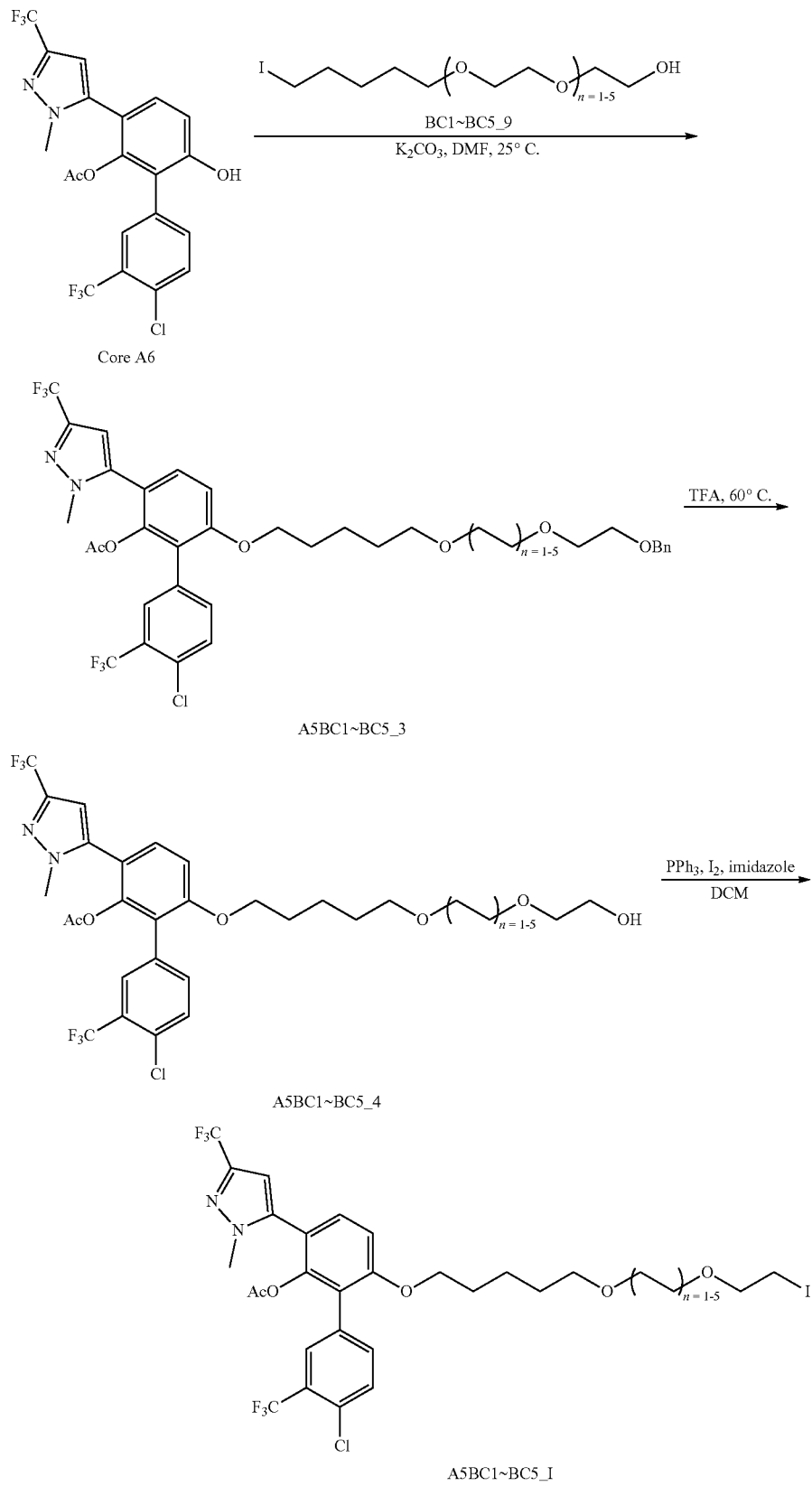

Scheme 6.
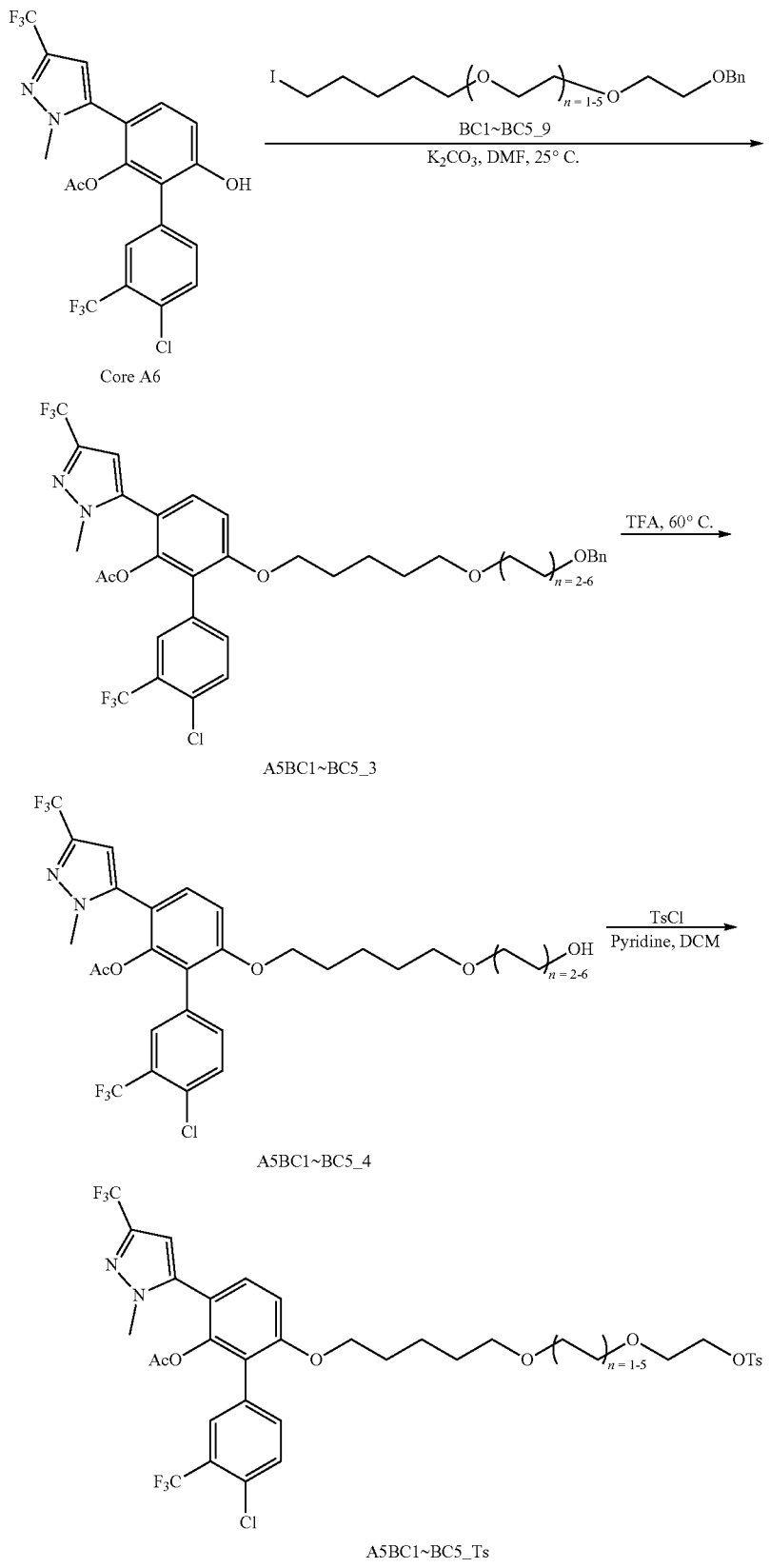

Scheme 7.
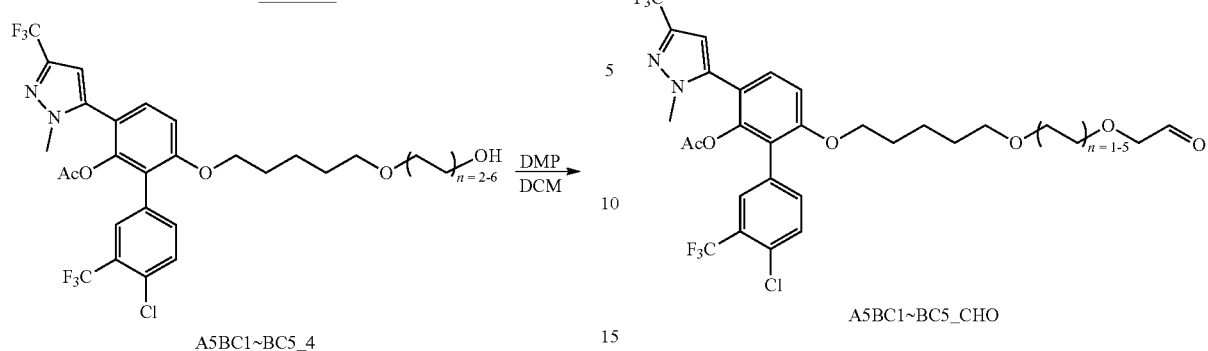
Scheme 8.
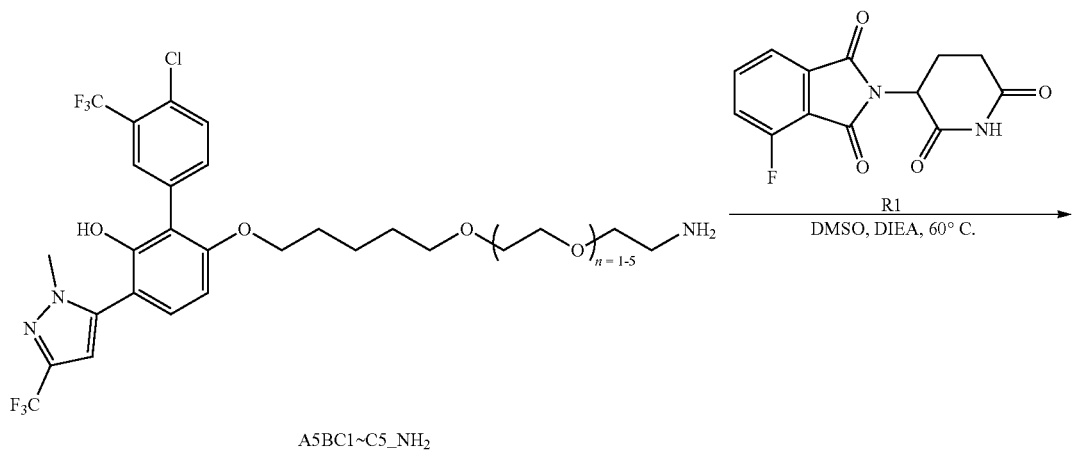
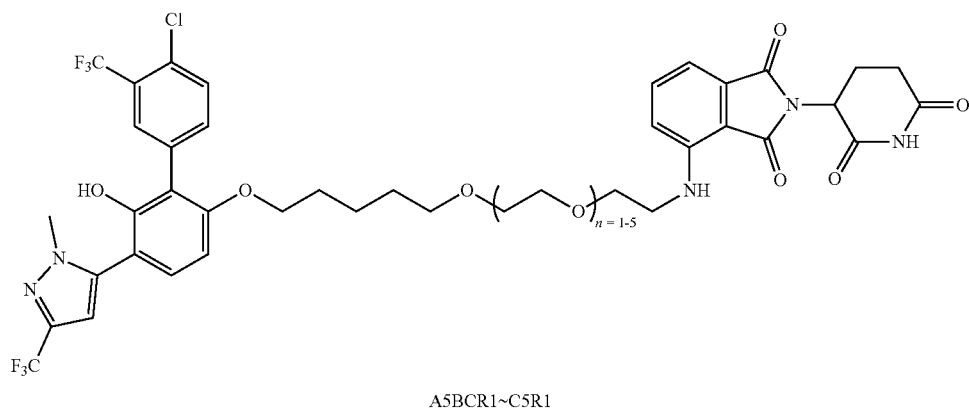

Scheme 9.
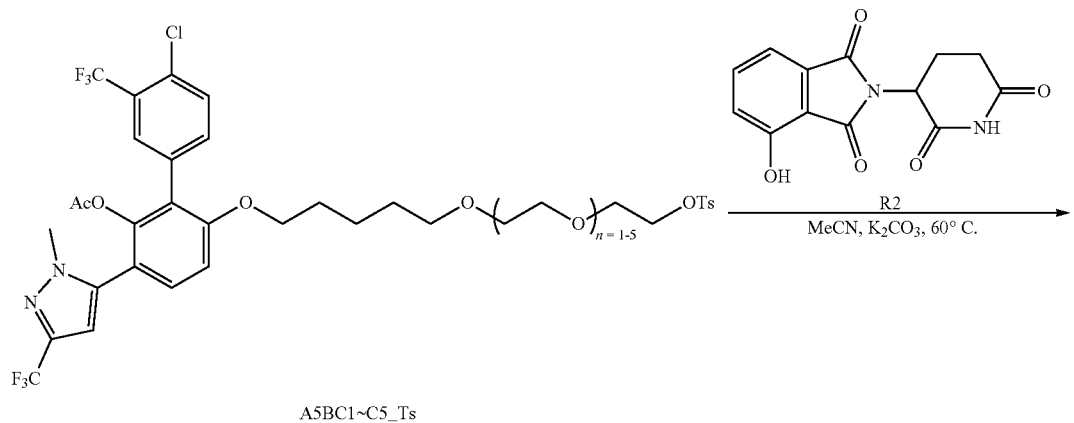
A5BC1~C5_Ts
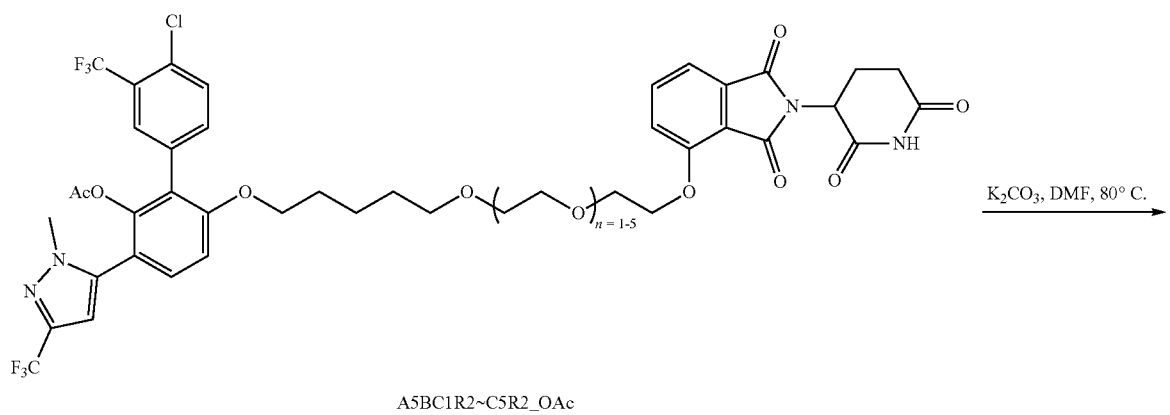
A5BC1R2~C5R2_OAc
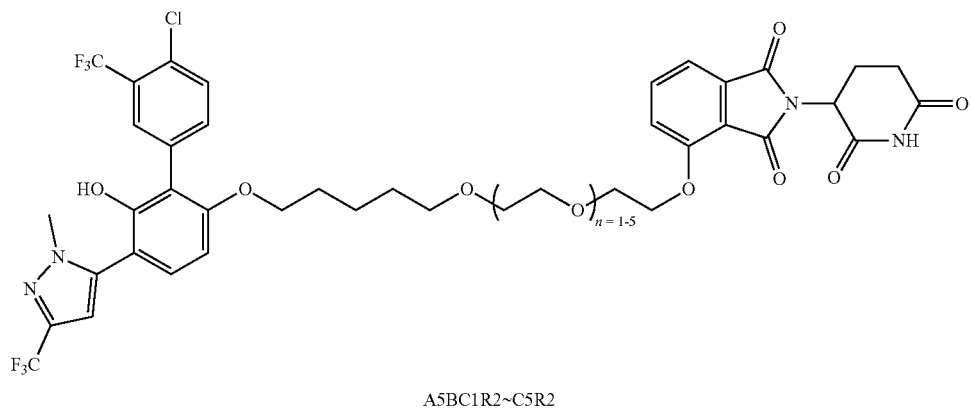
A5BC1R2~C5R2

Scheme 10.
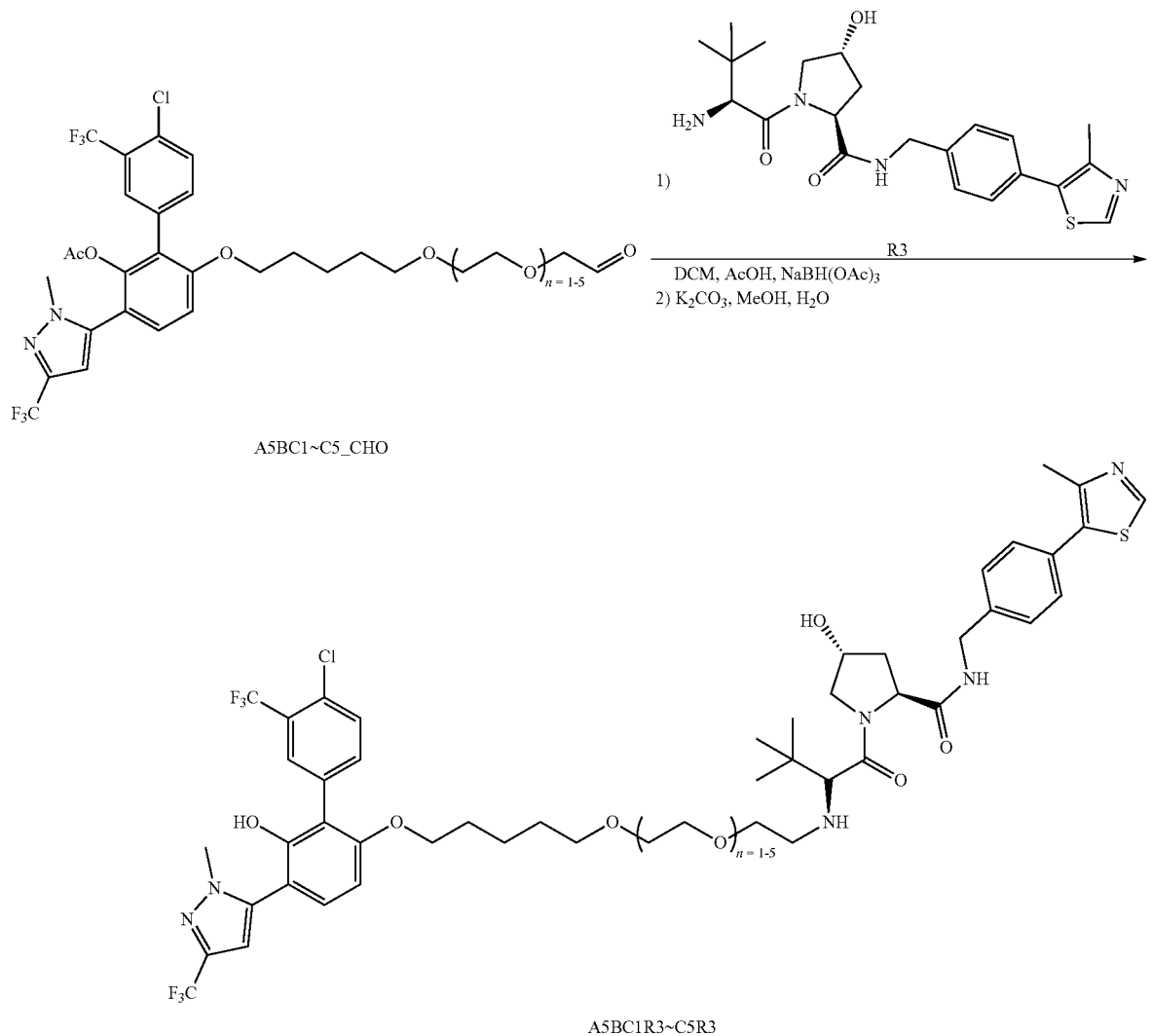
Scheme 11.
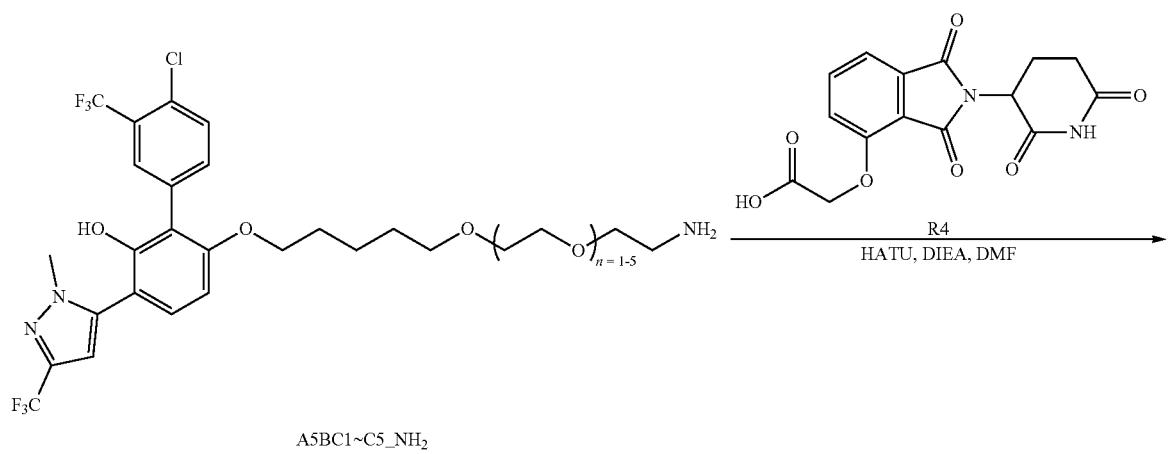

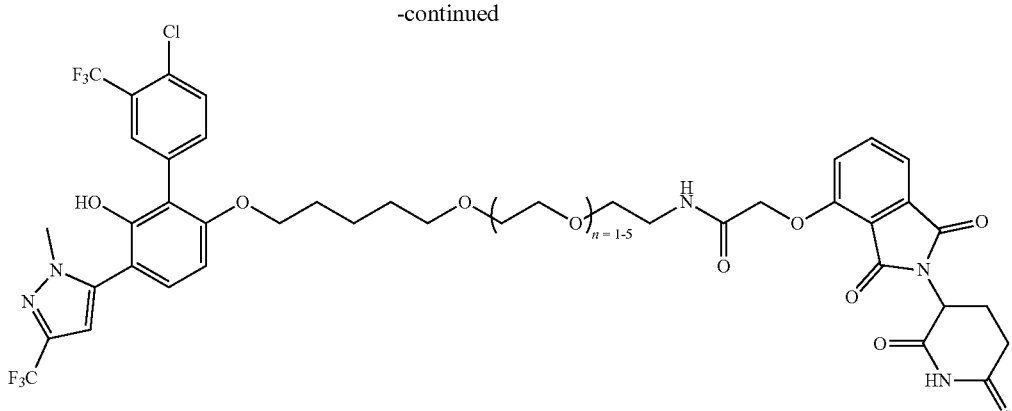
A5BC1R4~C5R4
Scheme 12.
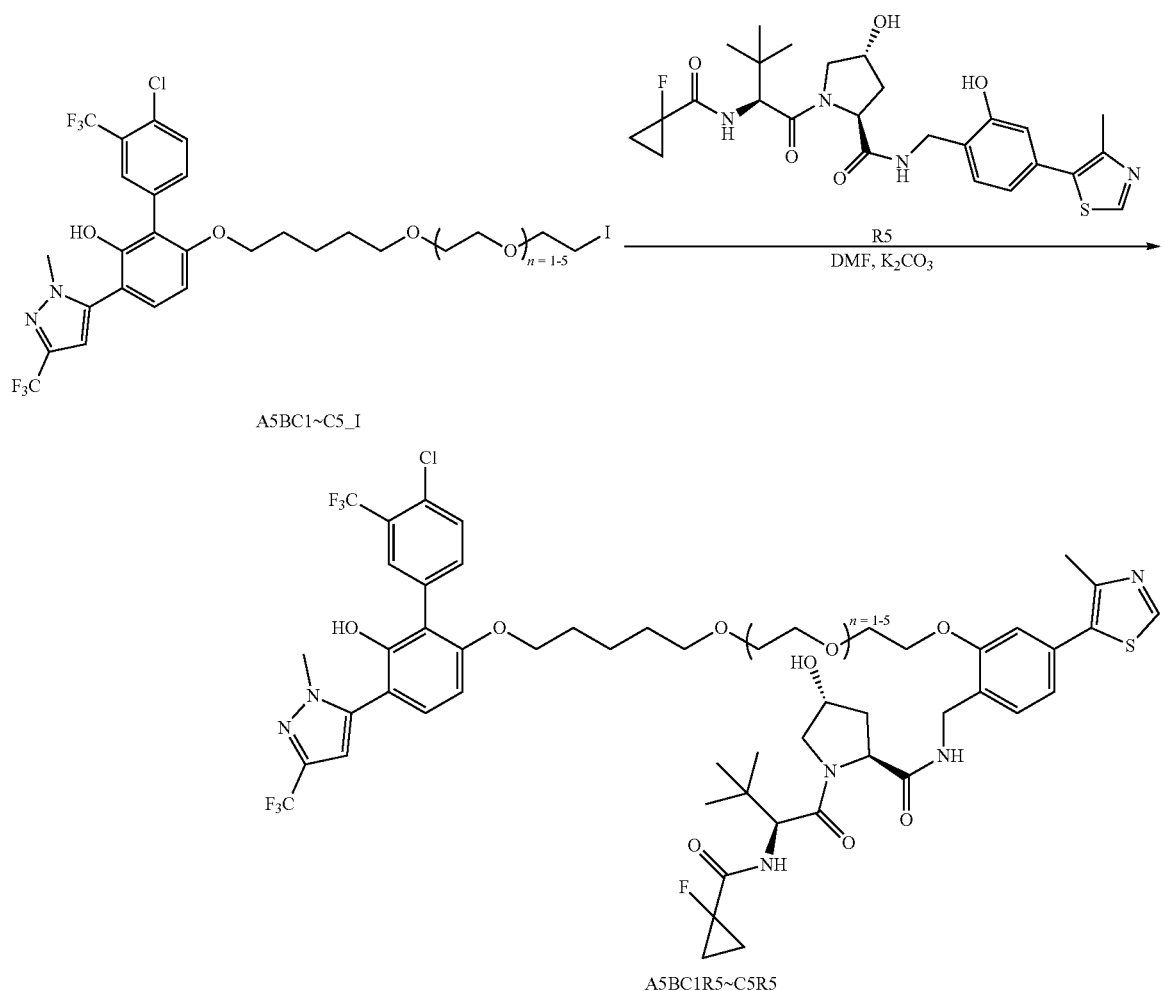
A5BC1~C5_I
A5BC1R5~C5R5

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A molecule selected from

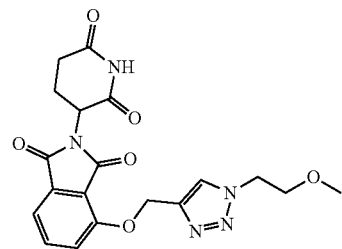

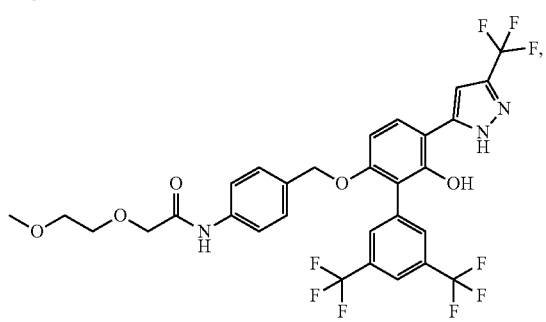

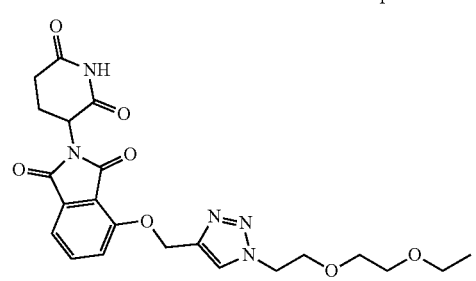

-continued

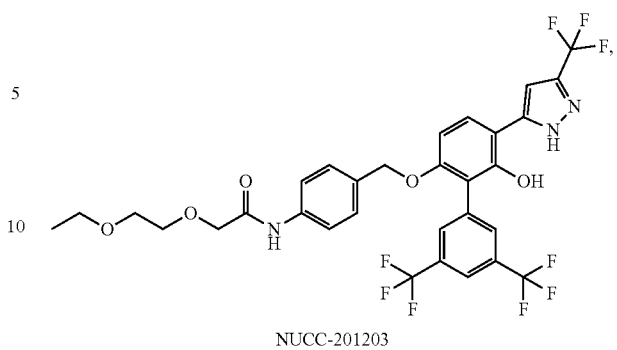

NUCC-201203

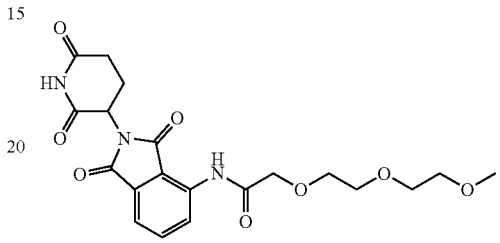

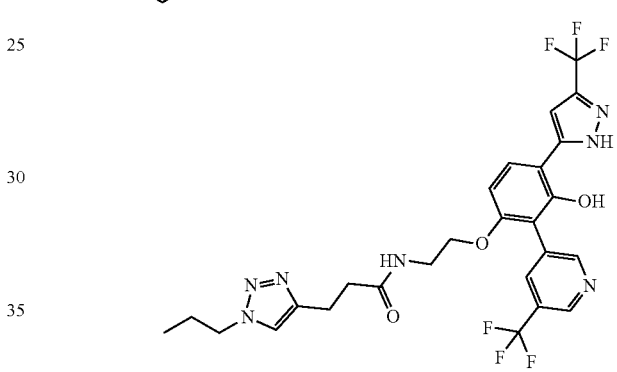

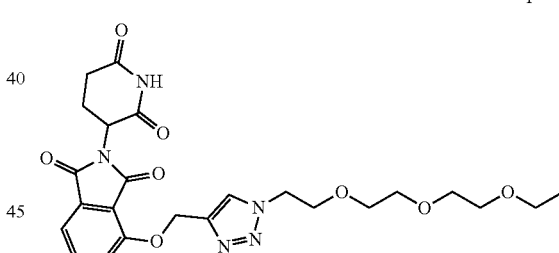

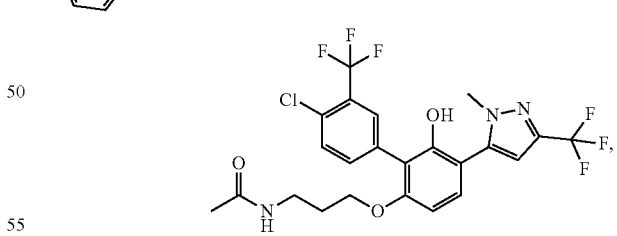

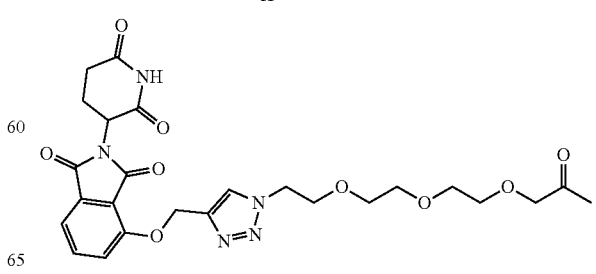

127
-continued
128
-continued
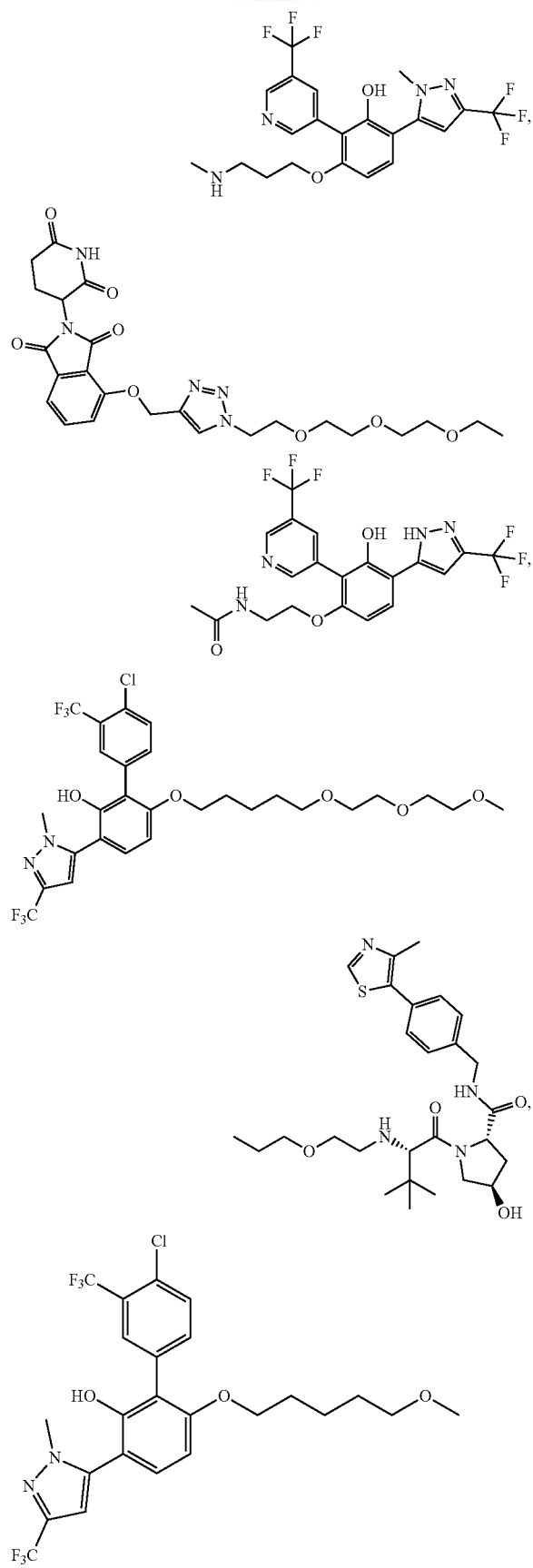
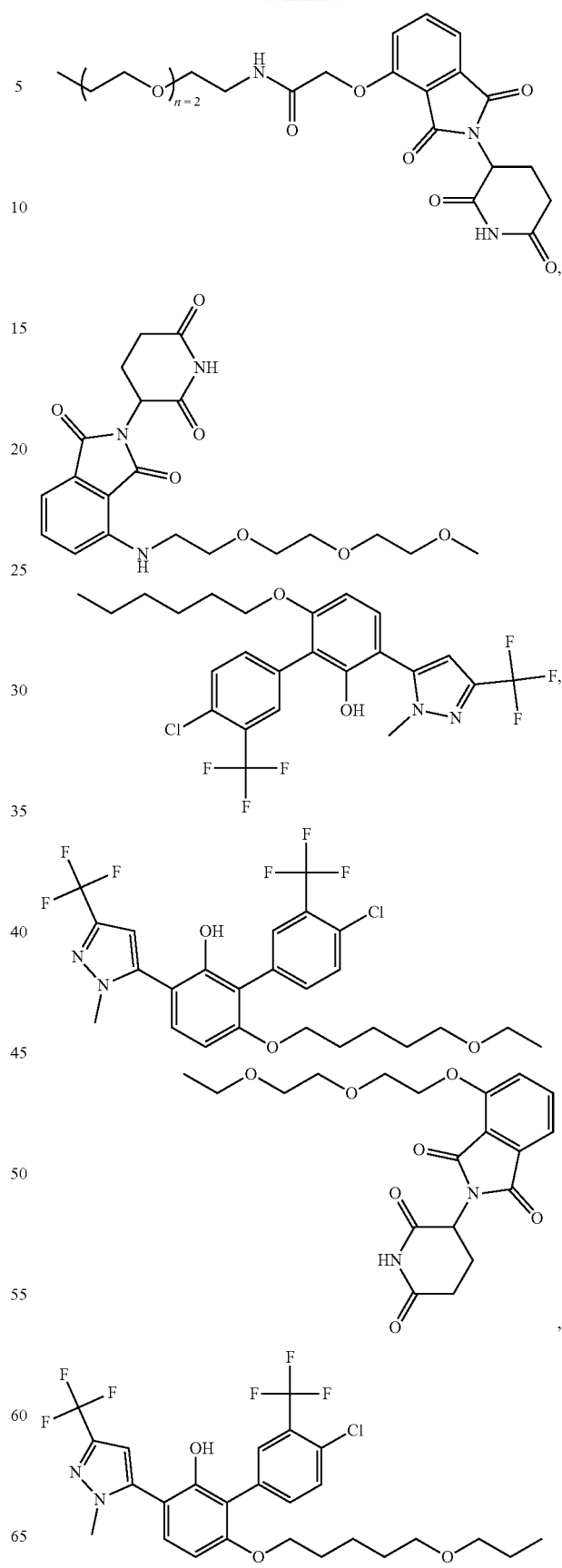

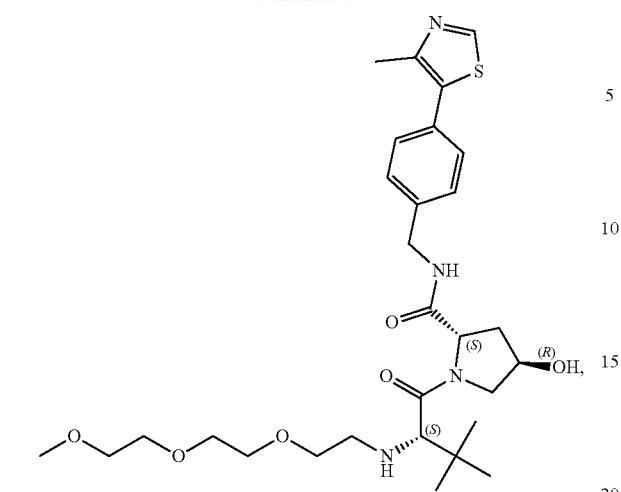
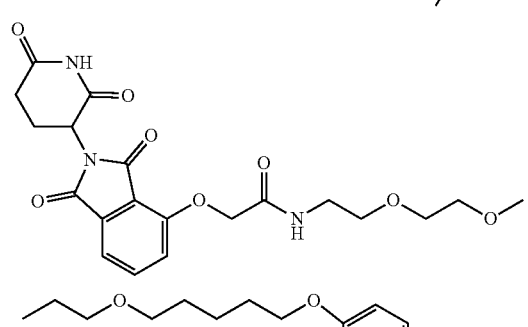
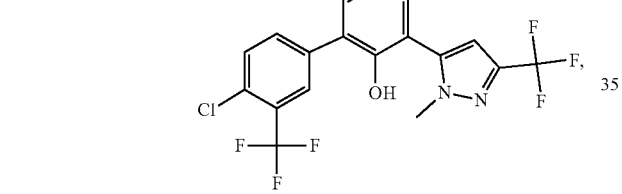
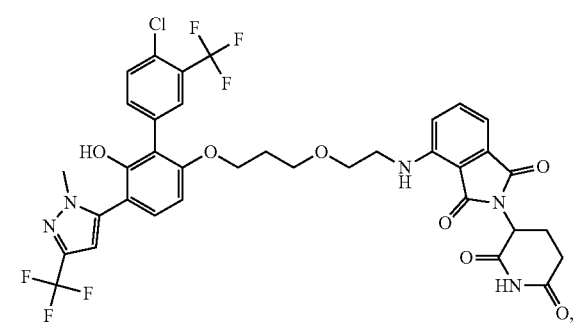
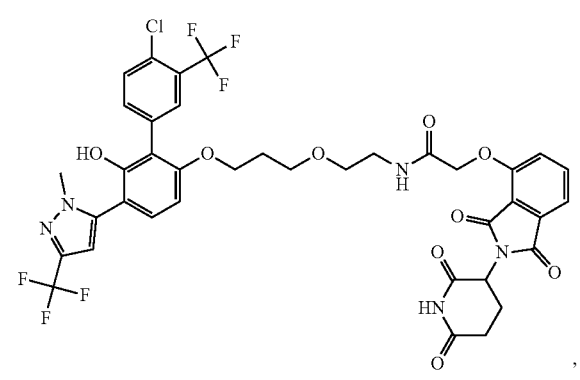
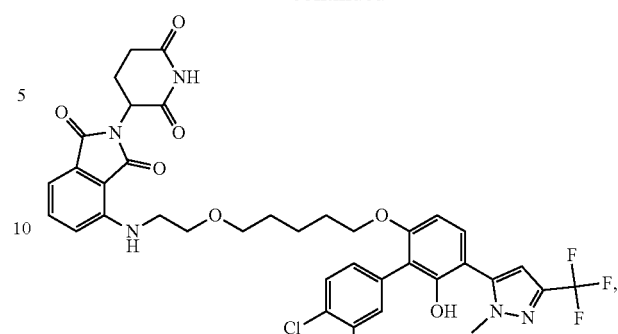
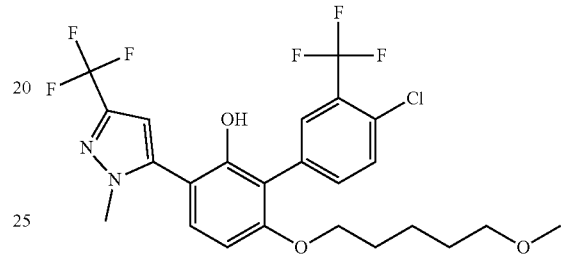
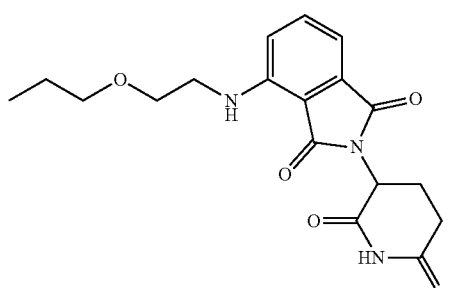
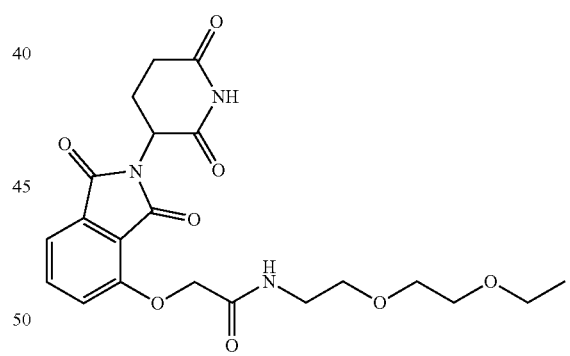
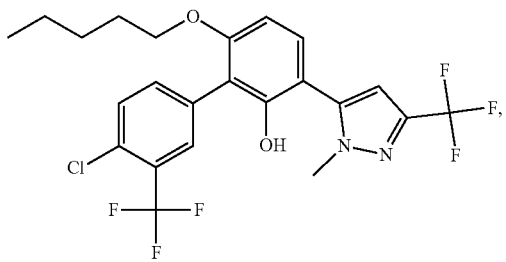

-continued

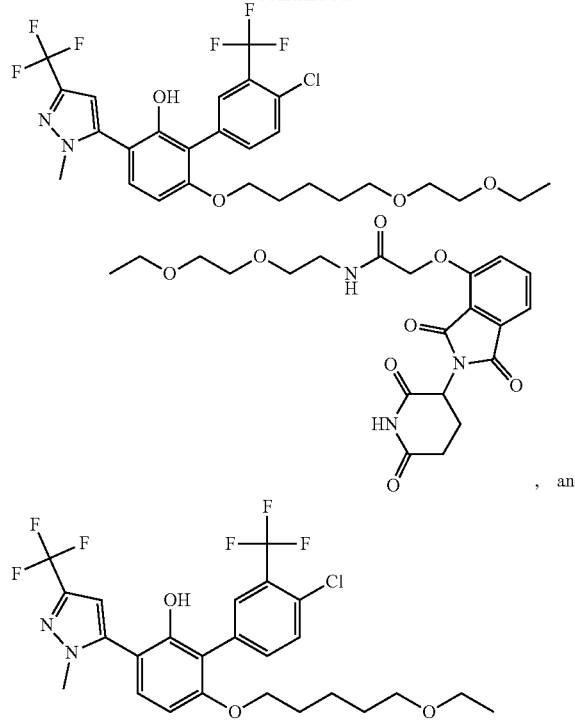

, and

-continued

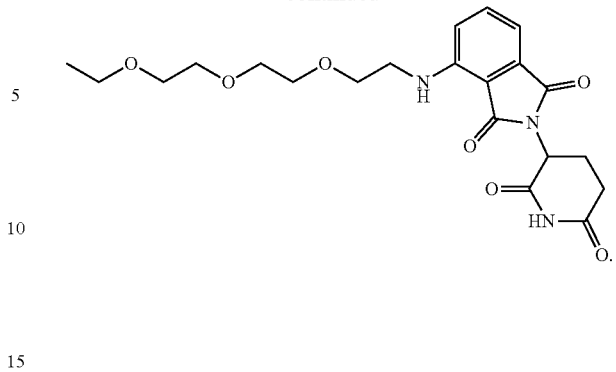

2. A pharmaceutical composition comprising a molecule of claim 1 and a suitable pharmaceutical carrier, excipient, or diluent.

3. A method of treating cancer, the method comprising administering the composition of claim 2 to a subject having the cancer.

4. The method of claim 3, wherein the cancer is selected from multiple myeloma, leukemia, non-small cell lung cancer, colon cancer, cancer of the central nervous system, melanoma, ovarian cancer, renal cancer, prostate cancer, and breast cancer.

* * * * *